United States Patent
Olivier et al.

(10) Patent No.: US 9,637,754 B2
(45) Date of Patent: *May 2, 2017

(54) DOMINANT NEGATIVE MUTANT KRP PROTEIN PROTECTION OF ACTIVE CYCLIN-CDK COMPLEX INHIBITION BY WILD-TYPE KRP

(71) Applicant: TARGETED GROWTH, INC., Seattle, WA (US)

(72) Inventors: Paul Olivier, Seattle, WA (US); Jay Derocher, Bothell, WA (US); James Roberts, Seattle, WA (US)

(73) Assignee: Targeted Growth, Inc., Burien, WA (US)

( * ) Notice: Subject to any disclaimer, the term of this patent is extended or adjusted under 35 U.S.C. 154(b) by 210 days.

This patent is subject to a terminal disclaimer.

(21) Appl. No.: 14/253,004

(22) Filed: Apr. 15, 2014

(65) Prior Publication Data

US 2014/0331362 A1    Nov. 6, 2014

Related U.S. Application Data

(63) Continuation of application No. 11/460,941, filed on Jul. 28, 2006, now Pat. No. 8,742,205.

(60) Provisional application No. 60/703,999, filed on Jul. 29, 2005.

(51) Int. Cl.
   *C12N 15/82*     (2006.01)
   *C07K 14/415*    (2006.01)
   *C12N 9/12*      (2006.01)

(52) U.S. Cl.
   CPC ........ *C12N 15/8261* (2013.01); *C07K 14/415* (2013.01); *C12N 9/1205* (2013.01)

(58) Field of Classification Search
   CPC .................................................. C12N 15/8261
   See application file for complete search history.

(56) References Cited

U.S. PATENT DOCUMENTS

| | | | |
|---|---|---|---|
| 5,958,769 A | 9/1999 | Roberts et al. | |
| 6,087,175 A | 7/2000 | John | |
| 6,114,608 A | 9/2000 | Mettler et al. | |
| 6,559,358 B1 | 5/2003 | Murray | |
| 6,710,227 B1 | 3/2004 | Inze et al. | |
| 7,122,658 B1 | 10/2006 | Lappegard et al. | |
| 7,329,799 B2 | 2/2008 | Savidge et al. | |
| 7,803,990 B2 | 9/2010 | Abbitt | |
| 8,431,775 B2 | 4/2013 | Hegstad et al. | |
| 8,742,205 B2 | 6/2014 | Olivier et al. | |
| 9,062,323 B2 | 6/2015 | Olivier et al. | |
| 2004/0019926 A1 | 1/2004 | Frankard et al. | |
| 2007/0044171 A1 | 2/2007 | Kovalic et al. | |
| 2007/0056058 A1 | 3/2007 | Olivier et al. | |
| 2008/0134355 A1 | 6/2008 | Van Camp | |
| 2008/0216193 A1 | 9/2008 | Savidge et al. | |
| 2008/0307546 A1 | 12/2008 | Veylder et al. | |
| 2009/0070894 A1 | 3/2009 | Frankard et al. | |
| 2009/0087878 A9 | 4/2009 | La Rosa et al. | |
| 2009/0144863 A1 | 6/2009 | Song et al. | |
| 2011/0135647 A1 | 6/2011 | Nakamura et al. | |
| 2012/0131698 A1 | 5/2012 | Olivier et al. | |
| 2012/0284813 A1 | 11/2012 | Olivier et al. | |
| 2014/0143900 A1 | 5/2014 | Olivier et al. | |
| 2016/0002656 A1 | 1/2016 | Olivier et al. | |

FOREIGN PATENT DOCUMENTS

| | | |
|---|---|---|
| WO | WO 99/64599 A | 12/1999 |
| WO | WO 00/60087 A2 | 10/2000 |
| WO | WO 02/81623 A2 | 10/2002 |
| WO | WO 2005/007829 A2 | 1/2005 |
| WO | WO 2005/024029 A2 | 3/2005 |
| WO | WO 2006/081029 A2 | 8/2006 |
| WO | WO 2007/016319 A2 | 2/2007 |
| WO | WO 2009/092009 A2 | 7/2009 |
| WO | WO 2010/099083 A1 | 9/2010 |
| WO | WO 2012/142116 A2 | 10/2012 |

OTHER PUBLICATIONS

De Veylder, Lieven, et al. "Functional analysis of cyclin-dependent kinase inhibitors of Arabidopsis." The Plant Cell 13.7 (2001): 1653-1668.*
Nakai, T., et al, 2006, "Arabidopsis KRPs have distinct inhibitory activity toward cyclin D2-associated kinases, including plant-specific B-type cyclin-dependent kinase." FEBS letters 580(1): 336-340.*
Cheng et al., "Downregulation of multiple CDK inhibitor ICK/KRP genes upregulates the E2F pathway and increases cell proliferation, and organ and seed sizes in Arabidopsis", The Plant Journal, 75: 642-655 (2013).
Coelho et al., "Cyclin-Dependent Kinase Inhibitors in Maize Endosperm and Their Potential Role in Endoreduplication", Plant Physiology, 138: 2323-2336 (2005).
Devos and Gale, "Genome Relationships: The Grass Model in Current Research", The Plant Cell, 12: 637-646 (2000).
European Patent Application No. 12771677.7, Extended European Search Report mailed Sep. 1, 2014.
European Patent Application No. 15161572.1, Partial European Search Report dated Aug. 24, 2015.
European Patent Application No. 15161572.1, Extended European Search Report dated Nov. 9, 2015.
Inzé and De Veylder, "Cell Cycle Regulation in Plant Development", Annual Review in Genetics, 40: 77-105 (2005).
Leenhardt et al. "Wheat lipoxygenase activity induces greater loss of carotenoids than vitamin E during breadmaking", J Agric Food Chem., 54(5):1710-1715 (2006).

(Continued)

*Primary Examiner* — Lee A Visone
*Assistant Examiner* — Fan Weihua

(57) ABSTRACT

Disclosed are mutant CDK inhibitor (CKI) polypeptides having dominant negative antagonist activity against wild-type CKI proteins, as well as related compositions, including nucleic acids and vectors encoding the mutant CKI polypeptides and transformed host cells and transgenic plants comprising such nucleic acids and vectors. Also disclosed are related methods for using the mutant proteins to modulate cell division in cells, particularly plant cells.

12 Claims, 4 Drawing Sheets

(56) References Cited

OTHER PUBLICATIONS

McKibbin et al., "Transcripts of Vp-1 homeologues are misspliced in modern wheat and ancestral species", PNAS, 99(15): 10203-10208 (2002).
Nakayama et al., "Mice lacking p27$^{Kip1}$ Display Increased Body Size, Multiple Organ Hyperplasia, Retinal Dysplasia, and Pituitary Tumors", Cell, 85:707-720 (1996).
NCBI Blast alignment of SEQ ID No. 11 and SEQ ID No. 7 obtained from http://blast.ncbi.nlm.nih.gov/Biast.cgi on Nov. 11, 2013.
PCT/US2011/060598, International Search Report and Written Opinion, mailed Mar. 22, 2013.
PCT/US2011/060598, International Preliminary Report on Patentability, dated May 14, 2013.
PCT/US2012/033047, International Search Report, mailed Jun. 28, 2012.
PCT/US2012/033047, Written Opinion by International Search Authority, mailed Jun. 28, 2012.
PCT/US2012/033047, International Preliminary Report on Patentability, dated Oct. 15, 2013.
PCT/US2012/033060, International Search Report, mailed Jul. 2, 2012.
PCT/US2012/033060, Written Opinion by International Search Authority, mailed Jul. 2, 2012.
PCT/US2012/033060, International Preliminary Report on Patentability, mailed Mar. 25, 2014.
Tranquilli and Dubcovsky, "Epistatic Interaction Between Vernalization Genes Vrn-Am1 and Vrn-Am2 in Diploid Wheat", The Journal of Heredity, 91(4): 304-306 (2000).
Yan et al., "Positional cloning of the wheat vernalization gene VRN1", PNAS, 100(10): 6263-6268 (2003).
Office Action in corresponding Chinese Patent Application No. 200680036207.8, mailed May 21, 2015 (with English translation), 6 pages.
Azzi et al., "Interaction Between the Cell-Cycle-Control Proteins p34$^{cdc2}$ and AD p9$^{CKShs2}$ Evidence for Two Cooperative Binding Domains in p9$^{CKShs2}$," Eur. J. Biochem, 203:353-360 (1992).
Coats et al., "Requirement of p27$^{Kip1}$ for Restriction Point Control of the Fibroblast Cell Cycle," Science 272:877-880 (1996).
De Veylder et al., "Functional Analysis of Cyclin-Dependent Kinase Inhibitors of Arabidopsis," Plant Cell13: 1653-1667 (2001).
Elmore et al., "Glyphosate-Resistant Soybean Cultivar Response to Glyphosate," Agron. J. 93:404-407 (2001).
Elmore et al., "Glyphosate-Resistant Soybean Cultivar Yields Compared with Sister Lines," Agron. J. 93:408-412 (2001).
Feig and Cooper, "Inhibition of Nlli 3T3 Cell Proliferation by a Mutant ras Protein with Preferential Affinity for GDP," Mol. Cell. Biol. 8:3235-3243 (1988).
Fernandez-Cornejo, Agriculture Information Bulletin No. (AIB786) 81 pp, Feb. 2004.
Fero et al., "A Syndrome of Multiorgan Hyperplasia with Features of Gigantism, Tumorigenesis, and Female Sterility in p27$^{Kip1}$-Deficient Mice," Cell 85:733-744 (1996).
Firpo et al., "Inactivation of a Cdk Inhibitor during Interleukin 2-Induced Proliferation of Human T Lymphocytes," Mol. Cell. Biol. 14:4889-4901 (1994).
Jackson et al., "Expression Profiling Reveals Off-target Gene Regulation by RNAi," Nature Biotech. 21:635-637 (2003).
Jasinski et al., "The CDK Inhibitor NtKIS1a is Involved in Plant Development, Endoreduplication and Restores Normal Development ofCyclin D3; 1-Overexpressing Plants," J. Cell Sci. 115:973-982 (2002).
Jasinski et al., "Comparative Molecular and Functional Analyses of the Tobacco Cyclin-Dependent Kinase Inhibitor NtKIS 1 a and its Spliced Variant NtKIS 1 b," Plant Physiol. 130:1871-1882 (2002).
Kiyokawa et al., "Enhanced Growth of Mice Lacking the Cyclin-Dependent Kinase Inhibitor Function of p27(Kip1)," Cell 85:721-732 (1996).
Korol eva, "CycD 1, a Putative G 1 Cyclin from Antirrhinum majus, Accelerates the Cell Cycle in Cultured Tobacco BY-2 Cells by Enhancing Both G1/S Entry and Progression Through S and G2 Phases," The Plant Cell 16:2364-2379 (2004).
Lui et al., "The Arabidopsis Cdc2a-Interacting Protein ICK2 is Structurally Related to ICK1 and is a Potent Inhibitor of Cyclin-Dependent Kinase Activity in vitro," Plant J. 21:379-385 (2000).
Moloney et al., "High Efficiency Transformation of Brassica napus Using Agrobacterium Vectors," Plant Cell Reports 8:238 (1989).
Nakagami et al., "Phosphorylation of Retinoblastoma-Related Protein by the Cyclin D/Cyclin-Dependent Kinase Complex is Activated at the G liS-Phase Transition in Tobacco," Plant Cell 14:1847-1857 (2002).
Polyak et al., "Cloning ofp27$^{Kip1}$' a Cyclin-Dependent Kinase Inhibitor and a Potential Mediator of Extracellular Antimitogenic Signals," Cell 78:59-66 (1994).
Russo et al., "Crystal Structure of the p27$^{Kip1}$ Cyclin-Dependent-Kinase Inhibitor Bound to the Cyclin A-Cdk2 Complex," Nature 382:325-331 (1996).
Schnittger et al., "Misexpression of the Cyclin-Dependent Kinase Inhibitor ICK1 IKRP 1 in Single-Celled Arabidopsis Trichomes Reduces Endoreduplication and Cell Size and Induces Cell Death," Plant Cell 15:303-315 (2003).
Van den Heuvel and Harlow, "Distinct Roles for Cyclin-Dependent Kinases in Cell Cycle Control," Science 262:2050-2054 (1993).
Vlach et al., "Phosphorylation-Dependent Degradation of the Cyclin-Dependent Kinase Inhibitor p27$^{KiP1}$"EMBO J. 16:5334-44 (1997).
Wang et al., "A Plant Cyclin-Dependent Kinase Inhibitor Gene," Nature 386:451-452 (1997).
Wang et al., "ICK1, a Cyclin-Dependent Protein Kinase Inhibitor From Arabidopsis thaliana Interacts With Both Cdc2a and CycD3, and its Expression is Induced by Abscisic Acid," Plant J. 15: 501-510 (1998).
Wang et al., "Expression of the Plant Cyclin-Dependent Kinase Inhibitor ICK1 Affects Cell Division, Plant Growth and Morphology," Plant J. 24:613-623 (2000).
Wang el al., "Genome-Wide Analysis of the Cyclin Family in Arabidopsis and Comparative Phylogenetic Analysis of Plant Cyclin-Like Proteins," Plant Physiol. 135:104-1099 (2004).
Zhou et al., "Plant CDK Inhibitors: Studies of Interactions With Cell Cycle Regulators in the Yeast Two-Hybrid System and Functional Comparisons in Transgenic Arabidopsis Plants," Plant Cell Rep. 20:967-975 (2002).
Zhou et al., "The Plant Cyclin-Dependent Kinase Inhibitor ICK1 has Distinct Functional Domains for in vivo Kinase Inhibition, Protein Instability and Nuclear Localization." Plant J. 35:476-489 (2003).
Zhou Y. et al. The plant cyclin-dependent kinase inhibitor ICK1 has distinct functional domains for in vivo kinase inhibition, protein instability and nuclear localization. Plant J. Aug. 2003;35(4):476-89.
Kwon T.K. et al. Identification of cdk2 binding sites on the p27Kip1 cyclin-dependent kinase inhibitor. Oncogene. Feb. 12, 1998; 16(6):755-62.
Vlach J. et al. Phosphorylation-dependent degradation of the cyclin-dependent kinase inhibitor p27. EMBO J. Sep. 1, 1997;16(17):5334-44.
International Search Report for International Application No. PCT/US2006/029349, mailed Apr. 20, 2007.
Written Opinion of the International Searching Authority for PCT/US2006/029349, mailed Apr. 20, 2007.
International Preliminary Report on Patentability for PCT/US2006/029349, mailed Jan. 29, 2008.
Search Report in corresponding European Patent Application No. 06788753, mailed Apr. 15, 2009.
Examination Report in corresponding New Zealand Patent Application No. 566040, mailed Jan. 14, 2010.
An English translation of Office Action in corresponding Israeli Patent Application No. 189051, mailed May 23, 2010.
An English translation of Office Action in corresponding Russian Patent Application No. 2008107302, mailed Mar. 19, 2010.
An English translation of Office Action in corresponding Vietnamese Patent Application No. 1-2008-00384, mailed Jan. 18, 2010.

(56) References Cited

OTHER PUBLICATIONS

Office Action in corresponding Australian Patent Application No. 2006275753, mailed Feb. 15, 2011.
An English translation of Office Action in corresponding Chinese Patent Application No. 200680036207.8, mailed Nov. 9, 2010.
An English translation of Office Action in corresponding Israeli Patent Application No. 189051, mailed Jun. 23, 2011.
Office Action in corresponding New Zealand Patent Application No. 566040, mailed Jun. 17, 2011.
An English translation of Office Action in corresponding Ukrainian Patent Application No. a 200802670, mailed Jul. 11, 2011.
Office Action in corresponding Chinese Patent Application No. 200680036207.8, mailed Dec. 23, 2011.
An English translation of the Office Action in corresponding Chinese Patent Application No. 200680036207.8, mailed Dec. 23, 2011.
Office Action in corresponding Japanese Patent Application No. 2008-524180, mailed Jan. 4, 2012.
An English translation of the Office Action in corresponding Japanese Patent Application No. 2008-524180, mailed Jan. 4, 2012.
Office Action in corresponding Canadian Patent Application No. 2,619,383, mailed Nov. 2, 2012.
European Patent Application No. 11186399.9, Extended European Search Report dated Mar. 21, 2012, 8 pages.
U.S. Appl. No. 14/111,292, Advisory Action mailed Jul. 15, 2016, 5 pages.
European Patent Application No. 11839924.5, Extended European Search Report mailed Feb. 26, 2014.
U.S. Appl. No. 13/295,809, Office Action mailed Nov. 25, 2015, 16 pages.
U.S. Appl. No. 13/295,809, Office Action mailed Apr. 23, 2015, 14 pages.
U.S. Appl. No. 13/295,809, Office Action mailed Jun. 3, 2014, 16 pages.
U.S. Appl. No. 13/295,809, Office Action mailed Nov. 21, 2013, 32 pages.
U.S. Appl. No. 13/295,809, Office Action mailed Apr. 8, 2016, 17 pages.
U.S. Appl. No. 14/111,292, Final Rejection mailed Mar. 4, 2016, 16 pages.

* cited by examiner

FIG. 1A

```
BnKrp1   118 ----KSATEQPPTAVEIEDFFVEAEK---QLHDNFKKKYNFDFEKEKPLEG-RYEWVKL-
AtKRP1   140 ----AKLMTEMPTESEIEDFFVEAEK---QLKEKLKKKYNFDFEKEKPLEG-RYEWVKLE
AtKRP2   150 -RRLRKSLHETVKEAEIEDFFQVAEKDLRNKLLECSMKYNFDFEKDEPLGGGRYEWVKIN
BnKrp3   139 ----TPARDSTVPTIGEIEEFFAYAEQ---QQRLFMEKYNFDIVNDVPLPG-GYEWVQVS
AtKRP3   167 -EYTREQDNVIPTTSEMEEFFAYAEQ---QQRLFMEKYNFDIVNDIPLSG-RYEWVQVK
BnKrp4   192 EDSFSGSHRHLPTTPEIDEFFSAAEE---EQQKQFIEKYNFDPVNEQPLPG-RIEWKKVD
AtKRP4   233 EDSLSRSHRRRPTTPEMIEFFSGAEE---EQQKQFIEKYNFDPVNEQPLPG-RIEWTKVD
BnKrp5   144 -RRDSEEATQSVPSHEIEEFFAFAEQ---QQRFFTEKYNFDIVSENPLPG-RYEWTKVV
AtKRP5   137 -----SMISDSKSIQSDIEIFFASAEQ---QQRFFIQKYNFDIVSDNPLPG-RYEWVKVM
BnKrp6   136 -----SPEVSKSPTPGEIDEFLSELES---KDQRRFMBKYNFDIVNDKPLQG-RYKWDRVK
AtKRP6   144 -----QPGVRKTPTAAEIIDLFSELESPD-DKKQFIEKYNFDIVNDEPLEG-RYKWDRI-
AtKRP7   140 -TEKKKKMEKSPTQAEIDEFFSAAER---YEQKRITEKYNMDIVNDTPLEG-RYQWVSLK
p27       31 ---------NLFGPVDHEELTRDLEKHCRDMDEASQRKWNFDFQNHKPLEG-KYEWQEVE
                           Cyclin Binding              CDK Binding BnKrp1       ------------------------
AtKRP1   192 ------------------------
AtKRP2   209 P-----------------------
BnKrp3   192 P-----------------------
AtKRP3   222 P-----------------------
BnKrp4   248 D-----------------------
AtKRP4   289 D-----------------------
BnKrp5   199 P-----------------------
AtKRP5   189 P-----------------------
BnKrp6   188 PLK---------------------
AtKRP6       ------------------------
AtKRP7   195 P-----------------------
p27       81 KGSLPEFYYRPPRPPKGACK
```

FIG. 1B

```
Bn Krp1         124  PPTAVEEEDFTVEAEKQLHDNFKKKYNFDFEKEKPLEG-RYEWVKL----
Bn Krp3         146  VPTIGETEEFFAYAEQQQQLFMEKYNFDIVNDVPLPG-GYEWVQVSP-
Bn Krp4         202  LPTTPEMDEFFSAAEEEQKQFIEKYNFDPVNEQPLPG-REEWKKVDD-
Bn Krp5         154  VPS-HETEEFFAEAEQQQQRFFTKYNFDIVSENPIPG-RYEWEKVVP-
Bn Krp6         142  SPTPGETEEFLSELESKDQKRFMDKYNFDIVNDKPLQG-RYKMDRVKPL
Gm AAS13377     122  VPTESELEEFFAAAEKDIQKRFTKYNFDFVKDMPLEG-RYEWVQL---
Gm AAS13374     159  VPTELEIEEFFAASEKDIQKRFQDRYNMDIVKDVPLPG-RYEWVQLKP-
Gm AAS13375     152  MPTELEKEEFFVAAEKDIQKRFQEKYNMDIVKDVPLPG-RYEWVQLKP-
Gm AAS13376     136  MPTELEEEEFFAAAEKDIRKRFSEKYNYDIVSGVSLEG-RYEWVKL---
Gm CO980060*         -PPKAEIEEFFAMAEKYEQKKFTEKYNFDIVRDLPLEG-RYQWVRL---
Gm CO981606*         LPISREVDEFFAETEEAQQKKFIDKYNFDPVNEKPLSG-RYEWEKLKP

Zm AI737717*     68  VPPAQETQEFFAAAEAAHAKRFASKYNFDFVEGVPLDAGREEWTPGVSI
Zm AW267370*     41  IPESTEVNEYFAAEQRQQQAFIEKYNFDPVNDCPLPG-REEWVKLD--
Zm CD963560*     17  VPSSREMNEYFAAEQRQQQDFIDKYNFDPANDCPLPG-REEWVKLD---
Zm CB329626*    144  IPSSLEMEEFFSAAEQQEQENFREKYNFCPVNDCPLPG-RYEWARIDC-
Os CV727532*         IPASAELEAFFAAEEQRQRQAFIKYNFDPVNDCPLPG-REEWVKL--
Os CR293278*         VPESLEMEEFFAAAEQQQHQAFREKYNFCPVNDCPLPG-RYEWTRL--
Os BI306406*         -PPEEEVEAFLAAAESSVARRFAAKYNDIVKDAPEDG-RYEWVRVRP
Ta BG908519     145  IPCSAEMNEFFSAAEQPQQQAFIEKYNFDPVNDCPLPG-RYEWVKLDZ
Ta AI820225*         VPSSLEMDEFFAAAEQQQHQTRKKYNFCPASERPLPG-RYEWTVLDC
Pt CK096447*         IPTTCEMDEFFASVEQQQQLFIEKYNFDIVNDLPLSG-RYEWVRV-
Pt BU862176*         IPTTREMLEFFGPAEEEQLEQFTKYNFDPVSDKPLPG-RYEWEKL
Pt BU892281*         TDEEIEKFFGEIQNNIPQCFKKYNFDFDKDEPLEG-RYEWARL
Nt KIS1         117  KPSEKEIEEFFAARQKAILKRFRKKYNFDFEKEEPLEG-RYEWVREGS-
St BQ505644*         --SEAEIEEFFAAAEKDLHKTFAEKYNFDFAKEEPLEG-RYEWVR----
Gh AI728644*         IPSXAEIDEFFSVAEKYEQXEFAEKYXDIVXDVPLDG-RY--------
```

Bn= Brassica napus (canola)
Gm= Glycine max (soy)
Os= Oryza sativa (rice)
St= Solanum tuberosum (potato)
Gh= Gossypium hirsutum (cotton)
Ta= Triticum aestivum (wheat)
Pt= Populus tremula (poplar)
Nt= Nicotiana tabacum (tobacco)

FIG. 2

> Krp1 F151A; F153A codon optimized for expression in Maize

Atggtccggaagtgccggaagacgaaaggcaccgtgggggctagtagcacctatatgcaacttaggtcaagaaggatc
gtctaccgtagcgagaaggctagttcctctagttcgtcatgctgtgcttcaaataacaacggcgtgatcgaccttgaggagg
agcgggatggagagacagagacctcttcgtgcaggcgctccagcaaacgtaaactcttcgagaatcttagggagaagga
gagtatggaaaattctcagcaaatcgtagccggatttgattcggcggtgaaagagtctagcgactgctgctgttccagaagg
acgagtctgtctactaccgaggagaaggggaaaagcgccaccgagcaaccgccgacggctgtcgagattgaggatttctt
tgtcgaggcggagaaacagctccacgacaattttaagaagaaatataacgctgacgctgaaaaggagaagccactggag
ggcaggtacgagtgggttaaattgtccgagtga > Krp1 Y149A;F151A;F153A codon optimized for expression in Maize Atggtccggaagtgccggaagacgaaaggcaccgtgggggctagtagcacctatatgcaacttaggtcaagaaggatc
gtctaccgtagcgagaaggctagttcctctagttcgtcatgctgtgcttcaaataacaacggcgtgatcgaccttgaggagg
agcgggatggagagacagagacctcttcgtgcaggcgctccagcaaacgtaaactcttcgagaatcttagggagaagga
gagtatggaaaattctcagcaaatcgtagccggatttgattcggcggtgaaagagtctagcgactgctgctgttccagaagg
acgagtctgtctactaccgaggagaaggggaaaagcgccaccgagcaaccgccgacggctgtcgagattgaggatttctt
tgtcgaggcggagaaacagctccacgacaattttaagaagaaagcgaacgctgacgctgaaaaggagaagccactgga
gggcaggtacgagtgggttaaattgtccgagtga

FIG. 3

DOMINANT NEGATIVE MUTANT KRP PROTEIN PROTECTION OF ACTIVE CYCLIN-CDK COMPLEX INHIBITION BY WILD-TYPE KRP

RELATED APPLICATIONS

This application is a Continuation of U.S. patent application Ser. No. 11/460,941, filed Jul. 28, 2006, which claims priority to U.S. Provisional Patent Application No. 60/703,999, filed Jul. 29, 2005, each of which is incorporated herein by reference in its entirety.

BACKGROUND OF THE INVENTION

Plants have the same basic cell cycle as eukaryotes. Not surprising, they also have in common with eukaryotes kinases called cyclin dependent kinases (CDK) that regulate the transitions between different phases of the cell cycle. *Arabidopsis*, a model plant system used to study the cell cycle have several CDK sub-groups. CDKA is most similar to the cdc2 (CDK1) of mammals and contains the highly conserved Pro Ser Thr Ala Ile Arg Glu (PSTAIR) amino acid sequence (SEQ ID NO:1) in a region that mediates the interaction with their cyclin partner. *Arabidopsis* also has a plant-specific group of CDK called CDKB that is not conserved in higher animals. Plants do however lack the mammalian counterpart to the $G_1$ CDKs-CDK4 and CDK6. CDKA has been proposed to be the $G_1$ CDK (that is activated by the plant D-type cyclins), while CDKB has been demonstrated to be predominantly expressed in S-phase and later and, therefore, likely identified as the $G_2$/M specific CDK.

Activation/inactivation of these CDKs drives cells through the cell cycle and also dictates when cells are to exit the cell cycle. *Arabidopsis* contains up to 49 cyclins grouped into 10 subclasses (see Wang et al., *Plant Physiol.* 135:1084-1099, 2004). Only the A, B and D-classes appear to play a role in the cell cycle and activate CDKs (Wang et al., *Plant Physiol.* 135:1084-1099, 2004). CDKA is activated by the D-type cyclins, while CDKB is activated by A- and B-type cyclins.

In animals CDKs are negatively regulated by two families of CDK inhibitors (CKIs). One class, called inhibitor of CDK4 (INK4) is comprised of 4 members (p15, p16, p18 and p19) that bind to and inhibit the $G_1$ CDKs, namely CDK4 and CDK6, from binding the cyclin. The other group of inhibitors is called Kinase Inhibitor Proteins (KIPs) or CIP (CDK Interacting Protein) proteins and they are highly conserved in all animals. The CIP/KIP family predominantly inhibit the cyclin A- and E-CDK2 kinase activity. In plants, putative CKIs have been identified (Wang et al., *Nature* 386:451-452, 1997; Wang et al., *Plant J.* 15:501-510, 1998; De Veylder et al., *Plant Cell* 13:1653-1667, 2001; Jasinski et al., *Plant Physiol.* 130:1871-1882, 2002) and shown to inhibit purified cyclin/CDK kinase activity in vitro (Wang et al., 1997, supra; Wang et al., *Plant J.* 24:613-623, 2000; Lui et al., *Plant J.* 21:379-385, 2000). Expression of plant CKIs showed reduced growth with smaller organs containing larger cells (see Wang et al., 2000, supra; Jasinski et al., *J. Cell Sci.* 115:973-982, 2001; De Veylder et al., supra; Zhou et al., *Plant Cell Rep.* 20:967-975, 2002; Zhou et al., *Plant J.* 35:476-489, 2003; Schnittger et al., *Plant Cell* 15:303-315, 2003). In *Arabidopsis*, these CKIs, are called Inhibitors of CDK (ICKs) or KIP related proteins (KRPs). Seven ICK family members have been identified that most closely resemble the CIP/KIP family of CKIs. Each of these ICK/KRP family members has high amino acid sequence identity to $p27^{KIP1}$ but the identity is limited to the most C-terminal 30 amino acids. To date, no INK related CKIs have been identified in any plant.

Over expression of cyclins or knockouts of CKI illustrate that the well balanced cell cycle engine can easily be perturbed in mammals. This imbalance can ultimately lead to accelerated cell cycles, increased animal size and/or tumor development. Reducing or completely eliminating CKI "activity" results in increased cyclin/CDK kinase activity. This increased activity results in phosphorylation of downstream targets necessary for cell cycle progression and animals ultimately yields cell hyper-proliferation (Coats et al., *Science* 272:877-880, 1996). Deletion of the $p27^{KIP1}$ gene in mice results in larger mice due to excessive cyclin/cdk activity that leads to excessive cell proliferation (Fero et al., *Cell* 85:733-744, 1996; Kiyokawa et al., *Cell* 85:721-732, 1996; Nakayama et al., *Cell* 85:707-720, 1996).

Mechanisms exist to suppress expression of various members of the KRP family. Post-transcriptional gene silencing (PTGS) in plants is an RNA-degradation mechanism similar to RNA interference (RNAi) in animals. RNAi results in the specific degradation of double-stranded RNA (dsRNA) into short 21-23 bp dsRNA fragments which ultimately play a role in the degradation of a population of homologous RNAs. In plants, PTGS uses an inverted repeats (IR) strategy to suppress gene expression in many plants species including crop plants such as corn, soy and Canola to name a few. However, IR technology has several drawbacks such as the efficiency of IR sequence, off target gene regulation (Jackson et al., *Nature Biotech.* 21:635-637, 2003), transient silencing, overall IR stability, and the like. These drawbacks are compounded in the present case by the need to silence more than one gene at a time.

Conventional plant breeding has been the principle driving force for increased crop yields over the past 75 years (J. Fernandez-Cornejo, *Agriculture Information Bulletin No.* (*AIB*786) 81 pp, February 2004). More recently, transgenic crops have become available that for example have resistance to insect pests and herbicides. However, these transgenic crops do come with a yield penalty (Elmore et al., *Agron. J.* 93:408-412, 2001; Elmore et al., *Agron. J.* 93:404-407, 2001). To date, no known transgenic crop is commercially available that has an increase in seed size or an increase in crop yield.

There is a need in the art for improved methods of modifying characteristics of certain commercially valuable crops, including for example, but not limitation, increasing crop yields, increasing seed size, increasing the rate of germination, increasing root mass, and the like. The present invention as described herein meets these and other needs.

BRIEF SUMMARY OF THE INVENTION

The present invention provides a variant plant cyclin dependent kinase inhibitor (CKI) polypeptide having at least one modification relative to a wild-type CKI polypeptide. In certain embodiments, the modification(s) are within the CDK binding region so as to confer, relative to the wild-type CKI protein, modified binding affinity for CDK protein, while substantially maintaining binding affinity for a cyclin protein. The variant CKI polypeptides of the present invention have dominant negative antagonist activity against wild-type CKI function. When the variant is expressed within a cell expressing the corresponding wild-type CKI protein, or a cell expressing a wild-type CKI heterologous to the corresponding wild-type protein but having substantially equivalent wild-type function with respect to, inter alia, cyclin and CDK binding, the wild-type CKI biological activity is inhibited, leading to accelerated progression through the cell cycle and increased cell proliferation.

In other aspects, the present invention provides a recombinant nucleic acid encoding a variant CKI polypeptide, or a vector comprising the recombinant nucleic acid. The variant CKI-encoding nucleic acid or vector can be introduced into a host cell for amplification or expression of the nucleic acid. The host cells can be used, for example, in methods of the invention for producing the variant CKI polypeptides. Further, expression of the variant CKI polypeptide in a cell can be used in methods of the invention for modulating cell division. For example, expression of variant CKI polypeptide in a cell can lead to accelerated progression through the cell cycle and increased cell proliferation.

In still other aspects, a transgenic plant comprising a transgene encoding the variant CKI polypeptide is provided. Expression of the variant CKI polypeptide in transgenic plants can be used in methods of the invention for, e.g., increasing plant vigor, increasing root mass, increasing plant size, or increasing early germination, and the like.

DEFINITIONS

Unless defined otherwise, all technical and scientific terms used herein have the same meaning as commonly understood by one of ordinary skill in the art to which this invention belongs. Although any methods and materials similar to those described herein can be used in the practice or testing of the present invention, only exemplary methods and materials are described. For purposes of the present invention, the following terms are defined below.

The terms "a," "an," and "the" as used herein include plural referents, unless the context clearly indicates otherwise.

As used herein, the term "cyclin dependent kinase inhibitor" (also referred to herein as "CDK inhibitor" or "CKI") refers to a class of proteins that negatively regulate cyclin dependent kinases (CDKs). CKIs amenable to the present invention are those having separate polypeptide regions capable of independently binding a cyclin and a CDK. Such CKIs include, for example, identified families of plant CKIs (the seven identified *Arabidopsis* CKIs), having homology to Kinase Inhibitor Proteins (KIPs) in animals, referred to as KIP-related proteins (KRPs) (also known as Inhibitors of "CDKs," or "ICKs").

The terms "polypeptide" and "protein" are used interchangeably herein to refer to a polymer of amino acid residues.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions). Specifically, degenerate codon substitutions can be achieved by generating sequences in which the third position of one or more selected (or all) codons is substituted with mixed-base and/or deoxyinosine residues (see, e.g., Batzer et al., *Nucleic Acid Res.* 19:5081, 1991; Ohtsuka et al., *J. Biol. Chem.* 260:2605-2608, 1985; Rossolini et al., *Mol. Cell. Probes* 8:91-98, 1994). The term nucleic acid is used interchangeably with gene, cDNA, and mRNA encoded by a gene.

The term "naturally occurring," in the context of CKI polypeptides and nucleic acids, means a polypeptide or nucleic acid having an amino acid or nucleotide sequence that is found in nature, i.e., an amino acid or nucleotide sequence that can be isolated from a source in nature (an organism) and which has not been intentionally modified by human intervention. As used herein, laboratory strains of plants which may have been selectively bred according to classical genetics are considered naturally-occurring plants.

As used herein, "wild-type CKI gene" or "wild-type CKI nucleic acid" refers to a sequence of nucleic acid, corresponding to a CKI genetic locus in the genome of an organism, that encodes a gene product performing the normal function of the CKI protein encoded by a naturally-occurring nucleotide sequence corresponding to the genetic locus. A genetic locus can have more than one sequence or allele in a population of individuals, and the term "wild-type" encompasses all such naturally-occurring alleles that encode a gene product performing the normal function. "Wild-type" also encompasses gene sequences that are not necessarily naturally occurring, but that still encode a gene product with normal function (e.g., genes having silent mutations or encoding proteins with conservative substitutions).

The term "wild-type CKI polypeptide" or "wild-type CKI protein" refers to a CKI polypeptide encoded by a wild-type gene. A genetic locus can have more than one sequence or allele in a population of individuals, and the term "wild-type" encompasses all such naturally-occurring alleles that encode a gene product performing the normal function.

The term "mutant" or "variant," in the context of CKI polypeptides and nucleic acids of the present invention, means a polypeptide or nucleic acid that is modified relative to a corresponding wild-type polypeptide or nucleic acid.

The term "reference CKI polypeptide" is a term used herein for purposes of defining a mutant or variant CKI polypeptide: the term refers to a CKI polypeptide to which a mutant CKI polypeptide is compared for purposes of defining modifications in amino acid sequence. Thus, a mutant CKI polypeptide "comprising a CKI amino acid sequence having at least one modification relative to a reference CKI polypeptide" means that, except for the one or more amino acid modification(s), the mutant CKI polypeptide otherwise comprises the amino acid sequence of the reference polypeptide. In carrying out the present invention as described herein, reference CKI polypeptides are predetermined. A reference CKI polypeptide can be, for example, a wild-type and/or a naturally occurring CKI polypeptide, or a CKI polypeptide that has been intentionally modified.

The term "modified binding" or "altered binding" refers to a mutant CKI polypeptide encoded by a wild-type gene whose reference CKI polypeptide binds a cyclin/CDK complex. By the term "modified binding" or "altered binding" herein refers to the binding of the mutant CKI to the cyclin/CDK kinase complex. The term "modified binding" or "altered binding" refers to the relative binding of the mutant CKI polypeptide compared to the reference CKI polypeptide. "Modified binding" or "altered binding" can refer to a mutant CKI polypeptide that has equal binding, reduced binding, or equivalent binding to the cyclin/CDK complex compared to the reference CKI polypeptide.

"Recombinant" as used herein refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated mutant or variant CKI nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above. A recombinant protein is distinguished from naturally occurring protein by at least one or more characteristics.

With respect to amino acids, a "non-conservative" modification means a modification in which the wild type residue and the mutant residue differ significantly in one or more physical properties, including hydrophobicity, charge, size, and shape. For example, modifications from a polar residue to a nonpolar residue or vice-versa, modifications from positively charged residues to negatively charged residues or vice versa, and modifications from large residues to small residues or vice versa are nonconservative modifications. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g. glutamyl or aspartyl; or (d) a residue having a bulky side chain, e.g., phenylalanine, is substituted for (or by) one not having a side chain, e.g., glycine.

Conservative modifications are generally those shown below, however, as is known in the art, other substitutions may be considered conservative.

Ala: Ser
Arg: Lys
Asn: Gln, His
Asp: Glu
Cys: Ser
Gln: Asn
Glu: Asp
Gly: Pro
His: Asn, Gln
Ile: Leu, Val
Leu: Ile, Val
Lys: Arg, Gln, Glu
Met: Leu, Ile
Phe: Met, Leu, Tyr
Ser: Thr
Thr: Ser
Trp: Tyr
Tyr: Trp, Phe
Val: Ile, Len

The term "dominant negative," in the context of protein mechanism of action or gene phenotype, refers to a mutant or variant protein, or the gene encoding the mutant or variant protein, that substantially prevents a corresponding protein having wild-type function from performing the wild-type function.

The phrase "antagonist of a wild-type CKI" as used herein means that a mutant CKI polypeptide significantly decreases (inhibits) the ability of a wild-type CKI polypeptide to inhibit kinase activity of CDK/cyclin complexes as compared to kinase activity inhibition by the wild-type CKI polypeptide in the absence of the antagonist.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "plant" includes whole plants, plant organs (e.g., leaves, stems, flowers, roots, and the like), seeds, and plant cells (including tissue culture cells) and progeny thereof. The class of plants which can be used in the methods of the invention is generally as broad as the class of higher plants amenable to transformation techniques, including gymnosperms and angiosperms, both monocotyledonous and dicotyledonous plants, as well as certain lower plants such as algae. It includes plants of a variety of ploidy levels, including polyploid, diploid and haploid. Examples of monocotyledonous angiosperms include, e.g., asparagus, field and sweetcorn, barley, wheat, rice, sorghum, sugar cane, onion, millet, rye and oats and other cereal grains. Examples of dicotyledonous angiosperms include, but are not limited to, tomato, tobacco, cotton, rapeseed (Canola), camelina, field beans, soybeans, peppers, lettuce, and the like. Examples of woody species include poplar, pine, cedar, oak, fir, and the like.

A "heterologous sequence" is one that originates from a different species, or, if from the same species, is substantially modified from its original form. For example, a heterologous promoter operably linked to a structural gene is from a species different from that from which the structural gene was derived, or, if from the same species, is substantially modified from its original form.

The term "vector" refers to a piece of DNA, typically double-stranded, which may have inserted into it a piece of foreign DNA. The vector or replicon may be for example, of plasmid or viral origin. Vectors contain "replicon" polynucleotide sequences that facilitate the autonomous replication of the vector in a host cell. The term "replicon" in the context of this disclosure also includes polynucleotide sequence regions that target or otherwise facilitate the recombination of vector sequences into a host chromosome. In addition, while the foreign DNA may be inserted initially into, for example, a DNA virus vector, transformation of the viral vector DNA into a host cell may result in conversion of the viral DNA into a viral RNA vector molecule. Foreign DNA is defined as heterologous DNA, which is DNA not naturally found in the host cell, which, for example, replicates the vector molecule, encodes a selectable or screenable marker or transgene. The vector is used to transport the foreign or heterologous DNA into a suitable host cell. Once in the host cell, the vector can replicate independently of or coincidental with the host chromosomal DNA, and several copies of the vector and its inserted DNA can be generated. Alternatively, the vector can target insertion of the foreign or heterologous DNA into a host chromosome. In addition, the vector can also contain the necessary elements that permit transcription of the inserted DNA into a mRNA molecule or otherwise cause replication of the inserted DNA into multiple copies of RNA. Some expression vectors additionally contain sequence elements adjacent to the inserted DNA that allow translation of the mRNA into a protein molecule. Many molecules of mRNA and polypeptide encoded by the inserted DNA can thus be rapidly synthesized.

The term "transgene vector" refers to a vector that contains an inserted segment of DNA, the "transgene," that is transcribed into mRNA or replicated as a RNA within a host cell. The term "transgene" refers not only to that portion of inserted DNA that is converted into RNA, but also those portions of the vector that are necessary for the transcription or replication of the RNA. In addition, a transgene need not necessarily comprise a polynucleotide sequence that contains an open reading frame capable of producing a protein.

The terms "transformed host cell," "transformed," and "transformation" refer to the introduction of DNA into a cell. The cell is termed a "host cell," and it may be a prokaryotic or a eukaryotic cell. Typical prokaryotic host cells include various strains of E. coli. Typical eukaryotic host cells are plant cells (e.g., canola, soy, rice, or maize cells and the like), yeast cells, insect cells, or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In the context of CKI polypeptides and nucleic acids, "correspondence" to another sequence (e.g., regions, fragments, nucleotide or amino acid positions, or the like) is based on the convention of numbering according to nucleotide or amino acid position number, and then aligning the sequences in a manner that maximizes the number of nucleotides or amino acids that match at each position, i.e., in a manner that maximizes the percentage of sequence identity. Because not all positions with a given "corresponding region" need be identical, non-matching positions within a corresponding region may be regarded as "corresponding positions." Accordingly, as used herein, referral to an "amino acid position corresponding to amino acid position X" of a specified CKI polypeptide represents referral to a collection of equivalent positions in other recognized CKI polypeptides and structural homologues and families.

In a typical embodiment of the present invention relating to the KRP superfamily of CKI polypeptides and nucleic acids, "correspondence" of amino acid or nucleotide positions are typically determined with respect to amino acids within the CDK binding region, or nucleotides encoding the CDK binding region. Generally, as compared to other regions of KRP polypeptides, CDK binding regions of KRP CKIs share substantial sequence identity or similarity. Thus, one suitable technique for determining the CDK binding region of a KRP CKI polypeptide is to identify an amino acid region sharing substantial sequence identity or similarity to a known CDK binding region of a second KRP CKI (for example, from about amino acid positions 145-168 of Brassica napus Krp1 (Bn Krp1)). (See, e.g., FIG. 1A and FIG. 1B, showing an amino acid sequence alignment of several CKI family members with BnKrp1.) Once a sequence corresponding to a CDK binding region has been determined by sequence alignment, corresponding amino acid or nucleotide positions can be determined accordingly.

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, or 95% identity over a specified region), when compared and aligned for maximum correspondence over a comparison window, or a designated region, as measured using one of the following sequence comparison algorithms, or by manual alignment and visual inspection. Sequences are "substantially identical" to each other if they are at least about 25%, at least 30%, at least 35%, at least 40%, at least 45%, at least 50%, or at least 55% identical. These definitions also refer to the complement of a test sequence. Optionally, the identity exists over a polypeptide region that is at least about 6 amino acids residues in length, at least about 15 amino acid residues in length, at least about 25 amino acid residues in length, at least about 35 amino acid residues in length, at least about 50 amino acid residues in length, or at least about 100 or more amino acids in length, or over a nucleic acid region encoding such a polypeptide region. In certain preferred aspects of the present invention, a designated region for comparison is a CDK binding region of a CKI polypeptide, a polypeptide region comprising a portion of such a CDK binding region, or a polypeptide region comprising such a CDK binding region.

The terms "similarity" or "percent similarity," in the context of two or more polypeptide sequences, refer to two or more sequences or subsequences that have a specified percentage of amino acid residues that are either the same or similar as defined by a conservative amino acid substitution (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarity exists over a region that is at least about 6 amino acid residues in length, at least about 15 amino acid residues in length, at least about 25 amino acid residues in length, at least about 35 amino acid residues in length, at least about 50 amino acid residues in length, or at least about 100 or more amino acids in length.

In certain aspects of the present invention, for determination of sequence identity or similarity, a designated region for comparison is the CDK binding region of a CKI polypeptide, a polypeptide region comprising a portion of such a CDK binding region, or a polypeptide region comprising such a CDK binding region.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities or similarities for the test sequences relative to the reference sequence, based on the program parameters.

A "comparison window," as used herein, includes reference to a segment of contiguous amino acid or nucleotide positions in which a sequence may be compared to a reference sequence of the same number of contiguous positions after the two sequences are optimally aligned. With respect to comparison of CKI polypeptides in accordance with the present invention, a comparison window is typically from about 6 to about 200 or more contiguous amino acids, typically about 6 to about 50, about 6 to about 25, about 15 to about 100, about 15 to about 50, about 15 to about 30, about 20 to about 50, or about 25 to about 50 contiguous amino acids. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (*J. Mol. Evol.* 35:351-360, 1987). The method used is similar to the method described by Higgins and Sharp (CABIOS 5:151-153, 1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package (e.g., version 7.0 (Devereaux et al., *Nucl. Acids Res.* 12:387-395, 1984).

Another example of an algorithm that is suitable for determining percent sequence identity and sequence similarity are the BLAST and BLAST 2.0 algorithms, which are described in Altschul et al. (*Nucl. Acids Res.* 25:3389-3402, 1977), and Altschul et al. (*J. Mol. Biol.* 215:403-410, 1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad Sci. USA* 89:10915-10919, 1992) alignments (B) of 50, expectation (E) of 10, M=5, N=-4, and a comparison of both strands.

The BLAST algorithm also performs a statistical analysis of the similarity between two sequences (see, e.g., Karlin and Altschul, *Proc. Natl. Acad. Sci. USA* 90:5873-5887, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

Gene homologs and orthologs can also be identified using the HomoloGene resource of the National Center for Biotechnology Information (NCBI). A homolog or ortholog of a first gene can encode a gene product that has the same or a similar function as the gene product encoded by the first gene. Another indication that two nucleic acid sequences or polypeptides are orthologs is that the heterologous gene can complement (e.g., rescue) a null allele of the endogenous gene in a eukaryotic cell expression system.

BRIEF DESCRIPTION OF THE DRAWINGS

FIG. 1A and FIG. 1B show an amino acid sequence alignment of *Arabidopsis* KRP family members with *Brassica* Krp family members. The sequences of the *Arabidopsis* KRPs were obtained from the public database: AtKrp1 (Genbank # U94772) (SEQ ID NO:2); AtKrp2 (Genbank#CAB76424) (SEQ ID NO:3); AtKrp3 (Genbank # CAC41617) (SEQ ID NO:4); AtKrp4 (Genbank # CAC41618) (SEQ ID NO:5); AtKrp5 (Genbank # CAC41619) (SEQ ID NO:6); AtKrp6 (Genbank # CAC41620) (SEQ ID NO:7); and AtKrp7 (Genbank # CAC41621) (SEQ ID NO:8). The sequences for the *Brassica* KRPs (BnKrp1 (SEQ ID NO:68), BnKrp3 (SEQ ID NO:69), BnKrp4 (SEQ ID NO:70), BnKrp5 (SEQ ID NO:71), and BnKrp6 (SEQ ID NO:72)) were obtained as described in Example 1, infra. Also shown is the amino acid sequence for p27 (SEQ ID NO:73).

FIG. 2 shows an amino acid sequence alignment of corn (SEQ ID NO:9, SEQ ID NO: 76 through SEQ ID NO: 78), cotton (SEQ ID NO: 10), canola (SEQ ID NO:68 through SEQ ID NO:72), soy (SEQ ID NO:11, SEQ ID NO:79 through SEQ ID NO:83), poplar (SEQ ID NO:12, SEQ ID NO:84 and SEQ ID NO:85), tobacco (SEQ ID NO:13), wheat (SEQ ID NO:14 and SEQ ID NO:15), rice (SEQ ID NO:16, SEQ ID NO:86 and SEQ ID NO:87), and potato (SEQ ID NO:17) cyclin and CDK binding domains, illustrating the high degree of sequence identity within the CDK binding domain.

FIG. 3 shows mutant BnKrp1 nucleic acid sequences that have been codon optimized for expression in Maize, coding for either BnKrp1 F151A; 153A (SEQ ID NO:74) or BnKrp1 Y149A;F151A;F153A (SEQ ID NO:75).

DETAILED DESCRIPTION OF THE INVENTION

The present invention comprises compositions and methods for modulating plant cell division. In particular, provided are polypeptides that antagonize wild-type CKI protein function via a dominant negative mechanism, as well as related polynucleotides, host cells, transgenic plants, and methods for use thereof. A wide variety of transgenic vectors, containing a polynucleotide encoding a variant, dominant negative CKI polypeptide, can be used to practice the present invention. When the CKI transgenes of the present invention are introduced into plants and expressed, plant cell division is modulated. The modulation of cell division may occur throughout the plant or in a tissue or organ specific manner depending upon the type of promoter sequence operably linked to the variant CKI transgene. In particular, the compositions and methods provided herein can be used to accelerate progression of plant cells through the cell cycle, with a concomitant increase in cellular proliferation. Using the compositions and methods in this manner allows, e.g., for the generation of increased crop yields and/or seed size in any of a wide variety of plants. An increase in crop yield can include, for example, increased leaf tissue, increased fruit, increased flower production, increased root mass, and the like.

In particular embodiments of the invention, the variant CKI polypeptide is a KRP family member. This aspect of the present invention is based, at least in part, on the discovery that the CDK binding region of KRP family members is primarily responsible for inhibition of cyclin-CDK complexes. Thus, targeting the CDK binding region in KRP family members (as opposed to the cyclin binding region) allows for the generation of mutant proteins that are particularly efficacious dominant negative antagonists of wild-type CKI function.

Mutant CKI Polypeptides, Nucleic Acids, and Vectors

The CKI polypeptides of the present invention are mutant or variant proteins distinguishable from naturally occurring or wild-type CKIs. The variant CKI polypeptides comprise at least one modification, relative to a reference CKI polypeptide (e.g., a wild-type CKI protein), in the CDK or cyclin binding region of the protein. Typical modifications include amino acid substitutions, insertions, and/or deletions as compared to the corresponding wild-type sequence. Particularly suitable modifications are amino acid substitutions. In certain embodiments, the variant CKI polypeptide comprises at least one non-conservative modification (e.g., a substitution).

The mutant CKI polypeptides of the present invention are dominant negative proteins. The dominant negative approach is particularly amenable to CKI polypeptides having two polypeptide regions separately involved in CDK and cyclin binding. The general approach for creating the dominant negative mutants of the present invention include modifying one of the individual CDK and cyclin binding regions so as to modify "wild-type" CDK or cyclin binding. This modified CDK or cyclin binding region can result in either equivalent, reduced or eliminated binding to the cyclin or CDK compared to the wild-type polypeptide. In either case, the mutation would reduce or eliminate the CKI's kinase inhibitory activity. In order to design a dominant negative CKI polypeptide that can interfere with the wild type function, the mutant polypeptide must (1) substantially bind to cyclin/CDK complexes; (2) not substantially inhibit the cyclin CDK complex even at high concentrations; and (3) compete with a wild-type CKI polypeptide for binding to the cyclin/CDK complex. In vivo, mutant CKI polypeptides that fulfill all of these requirements result in elevated cyclin/CDK kinase activity in the cell, which in turn leads to increased cell proliferation and a higher mitotic index that ultimately leads to plants with increased yield, larger seeds, and/or some other characteristic associated with an elevated cyclin/CDK kinase activity in one or more regions of the plant.

In the particular case of KRP polypeptides, the CDK binding region, which is primarily responsible for cyclin/CDK kinase inhibition in this family of CKI polypeptides, is targeted for modification.

Particularly suitable modifications include amino acid substitutions, insertions, or deletions. For example, amino acid substitutions can be generated as modifications in the CDK or the cyclin-binding region that reduce or eliminate binding. Similarly, amino acid substitutions can be generated as modifications in the CDK or the cyclin-binding region that reduces or eliminates the CKI inhibitory activity. In typical embodiments, at least one non-conservative amino acid substitution, insertion, or deletion in the CDK or the cyclin binding region is made to disrupt or modify binding of the CKI polypeptide to a CDK or cyclin protein.

Substitutional CKI polypeptide mutants are those that have at least one amino acid residue in a reference CKI protein sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the CKI protein molecules of the present invention can be obtained by substituting an amino acid with another whose side chain is significantly different in charge and/or structure from that of the native amino acid, an amino acid with an opposite charge from that of the native amino acid, or an amino acid with the opposite hydrophilicity from that of the native amino acid, and the like. These types of substitutions would be expected to affect the structure of the polypeptide backbone and/or the charge or hydrophobicity of the molecule in the area of the substitution. In certain, exemplary embodiments of the present invention, a substitutional CKI mutant includes substitution of a non-alanine residue with alanine. In other variations, the substitutional CKI includes substitution of an amino acid residue with, for example, an oppositely charged amino acid, an amino acid residue with a larger side chain, an amino acid with the opposite hydrophilicity, a small non-polar amino acid (e.g., Cys, Thr, Ser, Ala, or Gly), or a polar amino acid (e.g., Pro, Glu, Asp, Asn, or Gln).

Insertional CKI polypeptide mutants are those with one or more amino acids inserted immediately adjacent to an amino acid at a particular position in the reference CKI protein molecule. Immediately adjacent to an amino acid means connected to either the α-carboxy or α-amino functional group of the amino acid. The insertion can be one or more amino acids. The insertion can consist, e.g., of one or two conservative amino acids. Amino acids similar in charge and/or structure to the amino acids adjacent to the site of insertion are defined as conservative. Alternatively, mutant CKI include the insertion of an amino acid with a charge and/or structure that is substantially different from the amino acids adjacent to the site of insertion.

Deletional CKI polypeptide mutants are those where one or more amino acids in the reference CKI protein molecules have been removed. In some embodiments, deletional mutants will have one, two or more amino acids deleted in a particular region of the CKI protein molecule. Deletional mutants can include, e.g., mutants having a truncation of the amino- or carboxy-terminus.

The methods of the present invention can be applied to any recognized member of the CKI family of proteins in which individual regions are involved in binding of CDK and cyclin proteins to inhibit CDK function. In one embodiment, the mutant CKI proteins are mutations or variants of proteins belonging to the KRP family of CKIs. As noted above, the CDK binding region of KRP family members is primarily responsible for kinase inhibition. Accordingly, the CDK binding region is preferably targeted for modification in the design of variant KRP CKI polypeptides. The CDK binding region of KRP proteins generally corresponds to amino acids 145-168 of *Brassica napus* Krp1 (BnKrp1) (SEQ ID NO:68). In certain embodiments, modification of the CDK binding region of a KRP family member comprises modification of at least one amino acid position, two amino acid positions, or more within the region corresponding to positions 145-168 of BnKrp1. (The corresponding region in *Arabidopsis thaliana* Krp1 comprises amino acids 167-190 (SEQ ID NO:2).) Particularly suitable amino acid positions for modification include those positions corresponding to amino acids 145, 148, 149, 151, 153, 155, 163, 164, 165, and/or 167 of *Brassica napus* Krp1 (BnKrp1). The corresponding amino acid residues in other CKI polypeptide are easily determined by sequence alignment using known methods and as further described herein.

In each case, the amino acids mentioned above are conserved in mammalian p27 and all contact the CDK in the crystal structure of p27 complexed with Cyclin A and CDK2. In one embodiment, modification of the KRP CDK binding region comprises modification of amino acids corresponding to amino acid positions 151 and 153 of BnKrp1 (e.g., an amino acid substitution, such as, for example, to alanine or an oppositely charged amino acid, at each of these sites). In other exemplary variations, in addition to modification of amino acids corresponding to positions 151 and 153 of BnKrp1, modification of the KRP CDK binding region further includes modification(s) at position(s) corresponding to amino acid(s) 149, 164, and/or 165 of BnKrp1 (e.g., an additional amino acid substitution at a position corresponding to amino acid 149 of BnKrp1; or two additional amino acid substitutions at positions corresponding to both amino acid 164 and amino acid 165 of BnKrp1). Such modification(s) to the KRP CKI polypeptide modify binding affinity for a CDK protein, while substantially preserving the ability of the variant protein to bind a cyclin protein.

Modification of the Krp CDK binding region of particular interest include, but are not limited to, modifications corresponding to any of the following amino acid substitutions:
BnKrp1 F145A;Y149A (SEQ ID NO:88)
BnKrp1 F145A;Y149A;F151A (SEQ ID NO:89)
BnKrp1 F145A;Y149A;F151A;F153A (SEQ ID NO:90)
BnKrp1 Y149A;F151A (SEQ ID NO:91)
BnKrp1 Y149A;F153A (SEQ ID NO:92)
BnKrp1 F151A;F153A (SEQ ID NO:93)
BnKrp1 F151A;F153A;Y149A (SEQ ID NO:94)
BnKrp1 F151A;F153A;E164A (SEQ ID NO:95)
BnKrp1 F151A;F153A;W165A (SEQ ID NO:96)
BnKrp1 F151A;F153A;E164A;W165A (SEQ ID NO:97)
BnKrp1 F151A;F153A;Y149A;E164A (SEQ ID NO:98)
BnKrp1 F151A;F153A;Y149A;W165A (SEQ ID NO:99)
BnKrp1 F151A;F153A;Y149A;E164A;W165A (SEQ ID NO:100)
BnKrp1 E164A;W165A (SEQ ID NO:101)

In certain embodiments, the CKI polypeptide modified as above is BnKrp1. In other variations, the CKI modified as above is not BnKrp1 (e.g., *Arabidopsis thaliana*), with the substituted amino acids corresponding to those set forth above.

Other modifications (e.g., substitutions, insertions, deletions) that affect CDK or cyclin binding, including additional modifications in KRP family members, can be identified using a variety of techniques, including structural alignment methods, sequence alignment methods, and the like. The mutant or variant proteins can be generated, for example, by using a PDA™ system previously described in U.S. Pat. Nos. 6,188,965; 6,296,312; and 6,403,312; alanine scanning (see U.S. Pat. No. 5,506,107), gene shuffling ((WO 01/25277), site saturation mutagenesis, mean field, sequence homology, or other methods known to those skill in the art that guide the selection of point mutation sites and types, as described further herein below.

The CKI polypeptide variants of the present invention can be constructed by mutating the DNA sequences that encode the corresponding wild-type CKI, or other corresponding CKI from which the variant is derived, such as by using techniques commonly referred to as site-directed mutagenesis. Nucleic acid molecules encoding the CKI proteins can be mutated by a variety of polymerase chain reaction (PCR) techniques well known to one of ordinary skill in the art. (See, e.g., *PCR Strategies* (M. A. Innis, D. H. Gelfand, and J. J. Sninsky eds., 1995, Academic Press, San Diego, Calif.) at Chapter 14); *PCR Protocols A Guide to Methods and Applications* (M. A. Innis, D. H. Gelfand, J. J. Sninsky, and T. J. White eds., Academic Press, NY, 1990). In addition, well known chemical and/or radiation mutagenesis methods are well known in the art can be used to induce mutations in the coding regions of KRP family member proteins. Screening can be carried out to locate those plants that might comprise a desired nucleotide sequence encoding a mutant or variant Krp of the present invention. Plants can be screened for changes in the amino acid sequence of the CKI, changes in kinase activity or the expected changes in phenotype followed by sequence analysis.

By way of non-limiting example, the two primer system utilized in the Transformer Site-Directed Mutagenesis kit from Clontech, may be employed for introducing site-directed mutants into a gene encoding a CKI protein. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (J. T. Baker) to confirm that no other alterations in the sequence have occurred (by band shift comparison to the unmutagenized control). Alternatively, the entire DNA region can be sequenced to confirm that no additional mutational events have occurred outside of the targeted region.

The verified mutant duplexes in the pET (or other) overexpression vector can be employed to transform *E. coli* such as strain *E. coli* BL21 (DE3) pLysS, for high level production of the mutant protein, and purification by standard protocols. The method of FAR-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by, for example, microbore HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

In the design of a particular site directed mutagenesis, it is generally desirable to first make a non-conservative substitution and determine (a) whether the targeted CDK- or cyclin-binding activity is impaired and (b) whether any non-targeted activity (e.g., cyclin binding if the CDK-binding region is targeted) is greatly impaired as a consequence. If the residue is by this means demonstrated to be important to a non-targeted biological activity, then conservative substitutions can be made.

Other site directed mutagenesis techniques can also be employed with CKI nucleotide sequences. For example, restriction endonuclease digestion of DNA followed by ligation may be used to generate deletion variants of CKIs, as described generally in section 15.3 of Sambrook et al., *Molecular Cloning: A Laboratory Manual* (2nd Ed., 1989 Cold Spring Harbor Laboratory Press, New York, N.Y.). A similar strategy may be used to construct insertion variants, as described in section 15.3 of Sambrook et al., supra. More recently Zhu et al. (*Proc. Natl. Acad. Sci. USA* 96:8768-8773, 1999) have devised a method of targeting mutations to plant genes in vivo using chimeric RNA/DNA oligonucleotides.

Mutant polypeptides with more than one amino acid substituted can be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type CKI DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

One particularly suitable technique for guiding identification of suitable modifications includes aligning CKI proteins by sequence alignmnet. There are a number of sequence alignmnent methodologies discussed above that may be used. Sequence-based alignment programs include, for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise. (See, e.g., Altschul et al., *J. Mol. Biol.* 215:403-410, 1990; Altschul et al., *Nucleic Acids Res.* 25:3389-3402, 1997, both incorporated by reference).

Figure 1A:
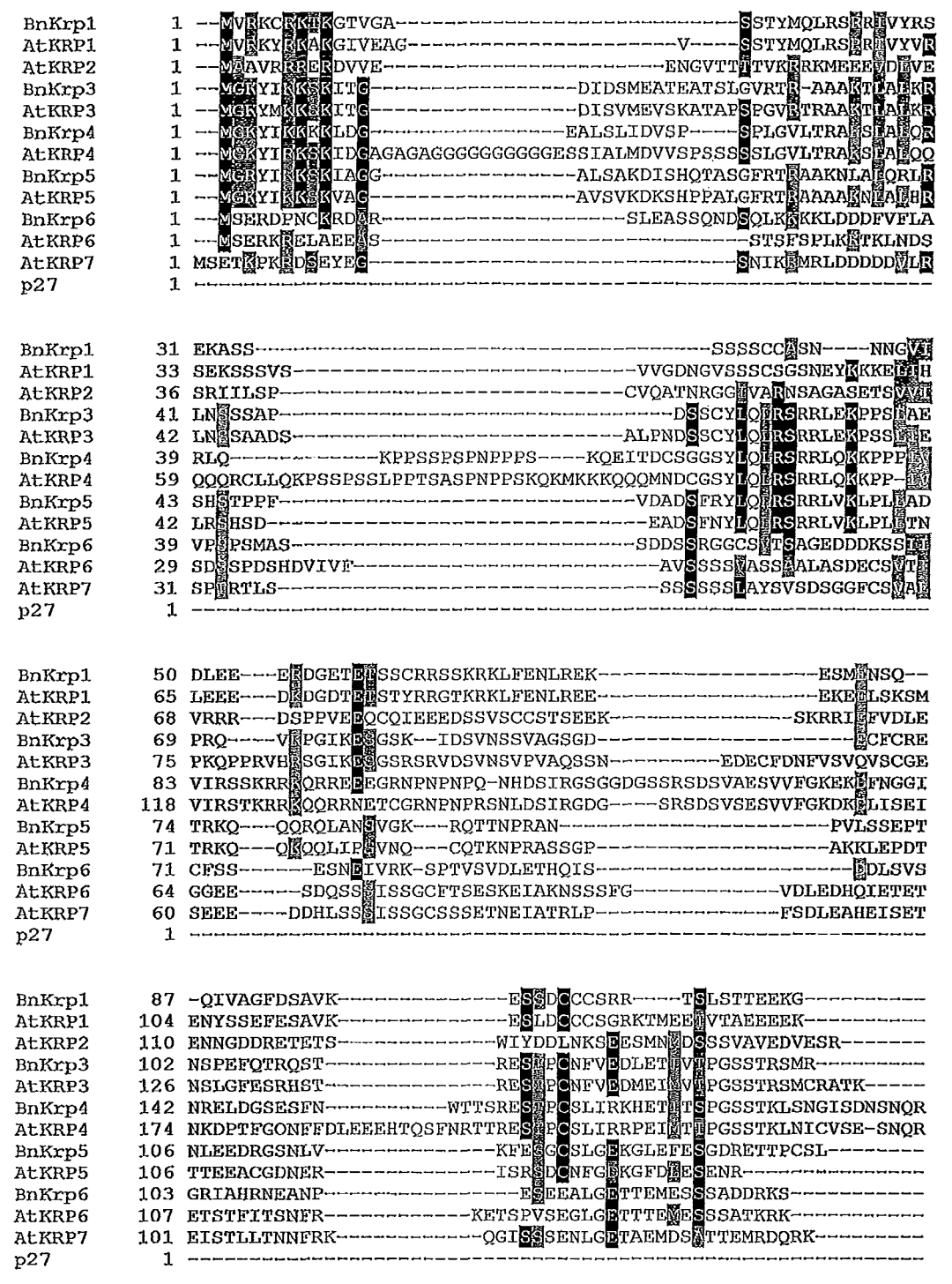

The amino acid sequences of related CKI polypeptides can be aligned, for example, into a multiple sequence alignment (MSA). (See, e.g., FIG. 1A and FIG. 1B.) The MSA can also be used to extend structural information known for one or more CKI polypeptides to additional CKI polypeptides (typically to CKI polypeptides sharing substantial sequence identity) that may not yet have been identified. Due to the high extent of structural homology between different CKI polypeptides, the MSA can be used as a reliable predictor of the effects of modifications at various positions within the alignment. Accordingly, in the case of KRP family members, for example, the CKI sequence and numbering shown in FIG. 1A and FIG. 1B can be used as an MSA reference point for any other KRP family member protein sequence. As noted previously, particularly suitable amino acid positions for modification include those corresponding to amino acid positions 145, 148, 149, 151, 153, 155, 163, 164, 165 and/or 167 of *Brassica napus* KRP1 (BnKrp1). Using the alignment depicted in FIG. 1A and FIG. 1B, and/or using alignment programs known in the art such as those described herein, one can use as a reference point the numbering system of the alignment program and may correlate the relevant positions of the CKI polypeptide with equivalent positions in other recognized members of CKIs or structural homologues and families. Similar methods can be used for alignment of the amino acid sequence(s) of CKI polypeptide that have yet to be sequenced.

In certain cases, the amino acids in the CKI polypeptide that interact with a CDK or cyclin protein can be identified directly from a three-dimensional structure of a CKI/CDK or CKI/cyclin complex. Equivalent information can be derived by analysis of the CKI/CDK or CKI/cyclin complex of a related CKI polypeptide. Thus, structural alignments can be used to generate the variant CKI polypeptides of the invention. There are a wide variety of structural alignment programs known in the art. See, e.g., VAST from the NCBI website; SSAP (Orengo and Taylor, *Methods Enzymol.* 266: 617-635, 1996); SARF2 (Alexandrov, *Protein Eng.* 9:727-732, 1996) CE (Shinydyalov and Bourne, *Protein Eng.* 11:739-747, 1998); (Orengo et al., *Structure* 5:1093-108, 1997; Dali (Holm et al., *Nucl. Acid Res.* 26:316-9, 1998, all of which are incorporated by reference).

Accordingly, useful modifications at CKI/CDK or CKI/cyclin interfaces may be selected using protein design or modeling algorithms such as PDA™ technology (see U.S. Pat. Nos. 6,188,965; 6,269,312; and 6,403,312, hereby incorporated by reference). Algorithms in this class generally use atomic-level or amino acid level scoring functions to evaluate the compatibility of amino acid sequences with the overall tertiary and quaternary structure of a protein. Thus, algorithms of this class can be used to select CDK- or cyclin-binding modifications and/or disruptions that do not substantially perturb the ability of variant CKI proteins to properly fold and interact with naturally occurring targets corresponding to non-modified regions of the protein. These technologies typically use high-resolution structural information of the target protein as input. In one embodiment, an experimentally determined structure of the appropriate CKI protein is used as input. In alternative embodiments, a MSA can be used to guide the construction of atomic-level homology models for CKI members based on the subset of the family whose three-dimensional structures have been determined using crystallographic or related methods. In yet another embodiment, the structural model of mammalian p27/cyclin interface can be used to predict the contact amino acid residue for plant CKI.

Mutant CKI polypeptides having modified, for example, reduced binding for a CDK or cyclin protein can also be identified by a large variety of other methods, including, for example, directed evolution (e.g., error prone PCR, DNA shuffling, and the like), single-site saturation mutagenesis, and alanine-scanning mutagenesis. In the case of KRP CKIs, for example, the use of these and/or other methods can allow the identification of additional modifications that reduce CDK binding activity and that lie outside of the CDK binding region described herein.

Also, molecular dynamics calculations can be used to computationally screen sequences by individually calculating mutant sequence scores and compiling a list. Also, residue pair potentials can be used to score sequences (Miyazawa et al., *Macromolecules* 18: 534-552, 1985, incorporated by reference herein) during computational screening.

Alternatively, libraries of variant CKI proteins can be made for testing. For example, a library of variant CKI amino acid sequences may be used to design nucleic acids encoding the variant CKI sequences and which may then be cloned into host cells, expressed, and assayed. The choice of codons, suitable expression vectors, and suitable host cells will typically vary depending on a number of factors, and can be easily optimized as needed.

In one particularly suitable method for screening libraries of mutants testing for dominant negative antagonist activity and/or other desired activities as outlined herein, multiple PCR reactions with pooled oligonucleotides are performed. Overlapping oligonucleotides are synthesized that correspond to the full-length gene. These oligonucleotides may represent all of the different amino acids at each variant position or subsets. These oligonucleotides may be pooled in equal proportions and multiple PCR reactions performed to create full-length sequences containing the combinations of mutations defined by the library. In addition, this may be done using error-prone PCR methods.

Typically, each overlapping oligonucleotide comprises only one position to be varied. Alternatively, the variant positions are too close together to allow this and multiple variants per oligonucleotide are used to allow complete recombination of all the possibilities (i.e., each oligo may contain the codon for a single position being mutated, or for more than one position being mutated). The multiple positions being mutated are preferably close in sequence to prevent the oligo nucleotide length from being impractical. For mutating multiple positions on an oligonucleotide, particular combinations of mutations may be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster." When the clusters are comprised of residues close together, and thus can reside on one oligonucleotide primer, the clusters can be set to the "good" correlations, and eliminate the bad combinations that may decrease the effectiveness of the library. However, if the residues of the cluster are far apart in sequence, and thus will reside on different oligonucleotides for synthesis, it may be desirable to either set the residues to the "good" correlation, or eliminate them as variable residues entirely. Alternatively, the library may be generated in several steps, so that the cluster mutations only appear together. This procedure, i.e., the procedure of identifying mutation clusters and either placing them on the same oligonucleotides or eliminating them from the library or library generation in several steps preserving clusters, can considerably enrich the library with properly folded protein. Identification of clusters may be carried out by a number of ways, e.g., by using known pattern recognition methods, comparisons of frequencies of occurrence of mutations or by using energy analysis of the sequences to be experimentally generated (for example, if the energy of interaction is high, the positions are correlated). These correlations may be positional correlations (e.g., variable positions 1 and 2 always change together or never change together) or sequence correlations (e.g., if there is residue A at position 1, there is always residue B at position 2). (See *Pattern Discovery in Biomolecular Data: Tools, Techniques, and Applications*; (Jason T. L. Wang, Bruce A. Shapiro, Dennis Shasha eds., New York, Oxford University, 1999); Andrews, *Introduction to Mathematical Techniques in Pattern Recognition* (New York, Wiley-Interscience, 1972); *Applications of Pattern Recognition* (K. S. Fu ed., Boca Raton, Fla., CRC Press, 1982); *Genetic Algorithms for Pattern Recognition* (Sankar K. Pal and Paul P. Wang eds., Boca Raton, Fla., CRC Press, 1996); Pandya, *Pattern Recognition with Neural Networks in C++* (Boca Raton, Fla., CRC Press, 1996; *Handbook of Pattern Recognition & Computer Vision* (C. H. Chen, L. F. Pau, and P. S. P. Wang. eds., 2nd ed. Singapore; River Edge, N.J., World Scientific, c1999); Friedman, *Introduction to Pattern Recognition: Statistical, Structural, Neural, and Fuzzy Logic Approaches* (River Edge, N.J., World Scientific, 1999, Series title: Series in machine perception and artificial intelligence; vol. 32); all of which are expressly incorporated by reference. In addition, programs used to search for consensus motifs can be used as well.

Oligonucleotides with insertions or deletions of codons can be used to create a library expressing different length proteins. In particular, computational sequence screening for insertions or deletions may result in secondary libraries defining different length proteins, which can be expressed by a library of pooled oligonucleotide of different lengths.

In another embodiment, mutant CKI polypeptides of the invention are created by shuffling a family (e.g., a set of mutants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are incorporated by reference herein. This set of sequences may also be an artificial set; for example, from a probability table (for example generated using SCMF) or a Monte Carlo set. Similarly, the "family" can be the top 10 and the bottom 10 sequences, the top 100 sequence, and the like. This may also be done using error-prone PCR.

Thus, in silico shuffling can be performed using the computational methods described herein (e.g., starting with two libraries or two sequences, random recombinations of the sequences may be generated and evaluated).

Error-prone PCR can be performed to generate a library of variant CKI polypeptides. See U.S. Pat. Nos. 5,605,793, 5,811,238, and 5,830,721, which are hereby incorporated by reference. This can be done on the optimal sequence or on top members of the library, or some other artificial set or family. In this method, the gene for the optimal sequence found in the computational screen of the primary library can be synthesized. Error-prone PCR is then performed on the optimal sequence gene in the presence of oligonucleotides that code for the mutations at the variant positions of the library (bias oligonucleotides). The addition of the oligonucleotides will create a bias favoring the incorporation of the mutations in the library. Alternatively, only oligonucleotides for certain mutations can be used to bias the library.

Gene shuffling can be performed with error-prone PCR on the gene for the optimal sequence, in the presence of bias oligonucleotides, to create a DNA sequence library that reflects the proportion of the mutations found in the CKI library. The choice of the bias oligonucleotides can be done in a variety of ways; they can be chosen on the basis of their frequency, e.g, oligonucleotides encoding high mutational frequency positions can be used; alternatively, oligonucleotides containing the most variable positions can be used, such that the diversity is increased; if the secondary library is ranked, some number of top scoring positions can be used to generate bias oligonucleotides; random positions may be chosen; a few top scoring and a few low scoring ones may be chosen; and the like. What is important is to generate new sequences based on preferred variable positions and sequences.

In another variation, PCR using a wild-type gene or other gene can be used. In this embodiment, a starting gene is used (e.g., the wild-type gene, the gene encoding the global optimized sequence, or a consensus sequence obtained, e.g., from aligning homologous sequences from different organisms). In this embodiment, oligonucleotides are used that correspond to the variant positions and contain the different amino acids of the library. PCR is done using PCR primers at the termini. This provides two benefits. First, this generally requires fewer oligonucleotides and may result in fewer errors. Second, it has experimental advantages in that if the wild-type gene is used, it need not be synthesized.

The mutant CKI polypeptides can be from any number of organisms, with CKI polypeptides from plants being particularly preferred. Suitable plants include, e.g., the class of higher plants amenable to transformation techniques, including both monocotyledonous and dicotyledonous plants, as well as certain lower plants such as algae. It includes plants of a variety of ploidy levels, including polyploid, diploid and haploid. In specific embodiments, the plant is *Brassica napus, Arabidopsis thaliana, Glycine max*, maize, rice, wheat, alfalfa, cotton, poplar, and the like.

As described above, the mutant CKI polypeptides of the invention are dominant negative antagonists of wild-type CKI polypeptides. In certain embodiments, the mutant CKI polypeptide physically interacts with only one or both of its corresponding cyclin or CDK proteins (i.e., the endogeneous, naturally occurring CDK or cyclin protein from the species from which the CKI mutant was derived) such that a CDK/cyclin complex comprising the mutant CKI is protected from CDK/cyclin kinase inhibition by the wild-type CKI protein.

In an alternative, non-mutually exclusive embodiment, the mutant CKI polypeptide physically interacts with only one or both of a heterologous CDK or cyclin proteins (i.e., a naturally occurring CDK or cyclin protein from a species that is different from the species from which the CKI mutant was derived), such that a complex of the heterologous CDK/cyclin comprising the mutant CKI is protected from CDK/cyclin kinase inhibition by a wild-type CKI protein that corresponds to the CDK and cyclin proteins within the complex (i.e., by a wild-type CKI protein endogenous to the CDK and cyclin proteins).

In some embodiments, the mutant CKI polypeptides of the invention are highly specific antagonists for the corresponding wild-type CKI protein. In alternative embodiments, the mutant CKI polypeptides of the invention are specific antagonists for more than one wild-type CKI polypeptide. For example, a mutant *Arabidopsis* CKI polypeptide may be a specific antagonist of a wild-type *Arabidopsis* CKI polypeptide only, or specific for wild-type *Arabidopsis, Brassica napus, Glycine max*, maize, rice, cotton, and/or poplar CKI polypeptides. Also, a mutant *Brassica* CKI polypeptide may be a specific antagonist of a wild-type *Brassica* CKI polypeptide only, or is a specific antagonist for wild-type *Arabidopsis, Brassica napus, Glycine max*, maize, rice, wheat, alfalfa, cotton, and/or poplar.

Mutant CKI polypeptides exhibit substantially decreased biological activity as compared to wild-type CKI polypeptides, including, e.g., modified binding to one of a CDK or cyclin protein and decreased inhibition of CDK/cyclin kinase complexes. Such decreased biological activity can be tested and validated using in vivo and/or in vitro assays. Suitable assays include, but are not limited to, CDK/cyclin kinase activity assays; CDK or cyclin binding assays; and cellular proliferation assays. A substantial decrease in biological activity as compared to wild-type CKI polypeptides means that the biological activity of the variant CKI polypeptide is less than 80% or less than 70%, typically less than 60% or less than 50%, more typically less than 40% or less than 30%, and preferably less than 20% or less than 10% that of a corresponding wild-type CKI polypeptide.

In some embodiments, the mutant CKI polypeptide includes a modification, as compared to a wild-type CKI polypeptide, in addition to those outlined herein (i.e., the mutant CKI proteins may contain additional modifications as compared to a corresponding wild-type CKI protein other than those used to generate dominant negative proteins). Examples include, but are not limited to, amino acid substitutions introduced to enable soluble expression in *E. coli* and amino acid substitutions introduced to optimize solution behavior. In addition, as outlined herein, any of the mutations depicted herein can be combined in any way to form additional variant CKI polypeptides. In addition, mutant CKI polypeptides can be made that are longer than the corresponding wild-type protein, for example, by the addition of epitope or purification tags, the addition of other fusion sequences, and the like or they may be shorter.

Mutant CKI polypeptides can also be identified as being encoded by mutant CKI nucleic acids. In the case of the nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence, with lower sequence identity being typical.

As will be appreciated by those in the art, due to the degeneracy of the genetic code, an extremely large number of nucleic acids may be made, all of which encode the mutant CKI polypeptides of the present invention. Thus, having identified a particular amino acid sequence, any number of different nucleic acids encoding the mutant protein can be made by simply modifying the sequence of one or more codons in a way which does not change the amino acid sequence of the mutant CKI polypeptide.

The mutant CKI polypeptides and nucleic acids of the present invention are preferably recombinant (unless made synthetically). As noted supra, mutants are typically prepared by site-specific mutagenesis of nucleotides in the DNA encoding a corresponding CKI protein, using cassette or PCR mutagenesis or another technique well known in the art, to produce DNA encoding the mutant, and thereafter expressing the DNA in recombinant cell culture. Amino acid sequence mutants are characterized by the predetermined nature of the mutation, a feature that sets them apart from naturally occurring allelic or interspecies variation of the mutant CKI protein amino acid sequence. As outlined above, the variants typically exhibit similar binding of either a CDK or cyclin protein (accordingly, as compared to a corresponding wild-type CKI protein, the mutant exhibits a substantial decrease in its inhibitory activity; although variants can also be selected that have additional variant characteristics.

While the site or region for introducing an amino acid sequence variation is predetermined, the mutation per se need not be predetermined. For example, in order to optimize the performance of a mutation at a given site, random mutagenesis may be conducted at the target codon or region and the expressed variant CKI proteins screened for the optimal combination of desired activity. Techniques for making substitution mutations at predetermined sites in DNA having a known sequence are well-known, for example, M13 primer mutagenesis and PCR mutagenesis. Screening of the mutants is done using assays of mutant CKI protein activities for optimum characteristics.

In some embodiments, amino acid substitutions are of single residues. In other embodiments, multiple amino acid residues are substituted (e.g., 2, 3, 4, or more amino acids can be substituted). Insertions are typically on the order of from about 1 to 20 about amino acids, although considerably larger insertions may be tolerated. Deletions range from about 1 to about 20 residues, or from about 1 to about 30 residues, although in some cases deletions may be much larger. In certain embodiments, mutant CKI polypeptides are chimeras derived from two or more wild-type CKI proteins, with at least one modification in the CDK or cyclin binding region as outlined herein.

Substitutions, deletions, insertions, or any combination thereof, are used to arrive at a final mutant. Generally, the modification(s) are done with respect to relatively few amino acids to minimize the alteration of the molecule. However, larger changes may be tolerated in certain circumstances.

Using a nucleic acid of the present invention encoding a mutant CKI polypeptide, a variety of vectors can be made. Any vector containing replicon and control sequences that are derived from a species compatible with the host cell can be used in the practice of the invention. The vectors can be either self-replicating extrachromosomal vectors or vectors which integrate into a host genome. Generally, expression vectors include transcriptional and translational regulatory nucleic acid regions operably linked to the nucleic acid encoding the mutant CKI polypeptide. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. The transcriptional and translational regulatory nucleic acid regions will generally be appropriate to the host cell used to express the polypeptide.

In certain embodiments, CKI nucleic acids are modified for enhance gene expression in a host cell using codon optimization, which involves replacing a codon sequence with a translation codon (corresponding to the same amino acid) that is highly used in the species of cell in which the DNA molecule is to be expressed. Examples of BnKrp1 mutant coding sequences (BnKrp1 F151A;F153A and Y149A;F151A;F153A) that have been optimized for expression in Maize are shown in FIG. 3. Codon optimization procedures are generally well-known in the art and can be used by those skilled in the art to obtain other codon optimized mutant Krp1 sequences in accordance with the present invention.

Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. The construction of suitable vectors containing DNA encoding replication sequences, regulatory sequences, phenotypic selection genes, and the variant CKI DNA of interest are prepared using standard recombinant DNA procedures. Isolated plasmids, viral vectors and DNA fragments are cleaved, tailored, and ligated together in a specific order to generate the desired vectors, as is well-known in the art (see, e.g., Maniatis, supra, and Sambrook et al., supra).

Promoter sequences encode either constitutive or inducible promoters. The promoters can be either naturally occurring promoters or hybrid promoters. Hybrid promoters, which combine elements of more than one promoter, are also known in the art, and are useful in the present invention. In a typical embodiment, the promoters are strong promoters, allowing high expression in cells, particularly plant cells. Promoters particularly suitable for use in accordance with the present invention are described further infra.

In addition, the expression vector can comprise additional elements. For example, the expression vector may have two replication systems, thus allowing it to be maintained in two organisms, for example in plant or insect cells for expression and in a prokaryotic host for cloning and amplification. Further, for integrating expression vectors, the expression vector contains at least one sequence homologous to the host cell genome, and preferably two homologous sequences which flank the expression construct. The integrating vector can be directed to a specific locus in the host cell by selecting the appropriate homologous sequence for inclusion in the vector. Constructs for integrating vectors are well known in the art.

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a mutant CKI nucleic acid is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include $CaPO_4$ precipitation, liposome fusion, Lipofectin®, electroporation, viral infection, and the like. Methods particularly suitable for introduction into plant cells are known in the art and are also described infra (see Section II, "Transgenic Plants"). Such methods include, for example, bombardment of cells with DNA laden microprojectiles. The mutant CKI nucleic acids may stably integrate into the genome of the host cell, or may exist either transiently or stably in the cytoplasm (e.g., through the use of traditional plasmids, utilizing standard regulatory sequences, selection markers, and the like).

Prokaryotes can be used as host cells for the initial cloning steps of the present invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include E. coli 102 strain 94 (ATCC No. 31,446), E. coli strain W3110 (ATCC No. 27,325) E. coli X1776 (ATCC No. 31,537), and E. coli B; however many other strains of E. coli, such as HB101, JM101, NM522, NM538, NM539, and many other species and genera of prokaryotes including bacilli such as Bacillus subtilis, other enterobacteriaceae such as Salmonella typhimurium or Serratia marcesans, and various Pseudomonas species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in for example Dower, in Genetic Engineering, Principles and Methods 12:275-296 (Plenum Publishing Corp., 1990); Hanahan et al., Meth. Enymol., 204:63, 1991. Plasmids typically used for transformation of E. coli include pBR322, pUCI8, pUCI9, pUCI18, pUC119, and Bluescript M13, all of which are described in sections 1.12-1.20 of Sambrook et al., supra. However, many other suitable vectors are available as well.

The mutant CKI polypeptides of the present invention are typically produced by culturing a host cell transformed with an expression vector containing a nucleic acid encoding the mutant CKI polypeptide, under the appropriate conditions to induce or cause expression of the mutant CKI polypeptide. For modulation of cell division, the CKI protein is expressed in its normal intracellular form. For applications of the present invention that include harvest or isolation of a mutant CKI polypeptide, the CKI mutant can be expressed as an intracellular protein or, alternatively, in a form that is secreted from the host cell. Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence can be obtained as a restriction fragment from any gene encoding a protein with a signal sequence. Thus, prokaryotic, yeast, and eukaryotic signal sequences can be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, Biochemistry (W.H. Freeman and Company, New York, N.Y., 1988, p. 769)), and can be used as signal sequences in appropriate eukaryotic host cells. Yeast signal sequences, such as, for example, acid phosphatase (Arima et al., Nuc. Acids Res. 11:1657, 1983), α-factor, alkaline phosphatase and invertase may be used to direct secretion from yeast host cells. Prokaryotic signal sequences from genes encoding, for example, LamB or OmpF (Wong et al., Gene 68:193, 1988), MalE, PhoA, or beta-lactamase, as well as other genes, may be used to target proteins expressed in prokaryotic cells into the culture medium.

The conditions appropriate for mutant CKI polypeptide expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be important for product yield.

The promoters most commonly used in prokaryotic vectors include the p-lactamase (penicillinase) and lactose promoter systems (Chang et al., Nature 375:615, 1978; Itakura et al., Science 198:1056, 1977; Goeddel et al., Nature 281:544, 1979) and a tryptophan (trp) promoter system (Goeddel et al., Nucl. Acids Res. 8:4057, 1980; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., Cell 20:269, 1980).

An illustrative example of a responsive promoter system that can be used in the practice of this invention is the glutathione-S-transferase (GST) system in maize. GSTs are a family of enzymes that can detoxify a number of hydrophobic electrophilic compounds that often are used as preemergent herbicides (Weigand et al., Plant Molecular Biology 7:235-243, 1986). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a mutant CKI coding sequence. If the mutant CKI gene is derived from a genomic DNA source than it is necessary to remove the native promoter during construction of the chimeric gene. This engineered gene is the combination of a promoter that responds to an external chemical stimulus and a gene responsible for successful production of a mutant CKI protein.

An inducible promoter is a promoter that is capable of directly or indirectly activating transcription of one or more DNA sequences or genes in response to an inducer. In the absence of an inducer the DNA sequences or genes will not be transcribed. Typically, the protein factor, that binds specifically to an inducible promoter to activate transcription, is present in an inactive form which is then directly or indirectly converted to the active form by the inducer. The inducer can be a chemical agent such as a protein, metabolite, a growth regulator, herbicide or a phenolic compound or a physiological stress imposed directly by heat, cold, salt, or toxic elements or indirectly through the action of a pathogen or disease agent such as a virus. A plant cell containing an inducible promoter can be exposed to an inducer by externally applying the inducer to the cell or plant such as by spraying, watering, heating or similar methods. If it is desirable to activate the expression of the target gene to a particular time during plant development, the inducer can be so applied at that time.

Examples of such inducible promoters include heat shock promoters, such as the inducible 70 KD heat shock promoter of Drosphilia melanogaster (Freeling et al., Ann. Rev. of Genetics 19:297-323); a cold inducible promoter, such as the cold inducible promoter from B. napus (White et al., Plant Physiol. 106, 1994); and the alcohol dehydrogenase promoter which is induced by ethanol (Nagao et al., Surveys of Plant Molecular and Cell Biology Vol. 3, p 384-438 (B. J. Miflin ed., Oxford University Press, Oxford, 1986).

A constitutive promoter is a promoter that is capable of directly or indirectly activating the transcription of one or more DNA sequences or genes in all tissues of a transgenic plant. Typically, a constitutive promoter such as the 35 S promoter of CaMV (Odell, Nature 313:810-812, 1985) is used. Other examples of constitutive promoters useful in plants include the rice actin promoter (McElroy et al., Plant Cell 2:163-171, 1990), maize HE histone (Lepetit et al., Mol. Gen. Genet. 231:276-285, 1992) and the like.

The CKI transgenes of the present invention can be expressed using a promoter such as is the BCEA (B. campestris embryo) promoter which has been shown to direct high levels of expression in very early seed development (i.e., is transcribed before the napin promoter). This is a period prior to storage product accumulation but of rapid pigment biosynthesis in the Brassica seed (derived from Johnson-Flanagan et al., J. Plant Physiol. 136:180, 1989; Johnson-Flanagan et al., Physiol. Plant 81:301, 1991). Seed storage protein promoters have also been shown to direct a high level of expression in a seed-specific manner (Voelker et al., Plant Cell 1:95, 1989; Altenbach et al., Plant Mol. Biol. 13:513, 1989; Lee et al., Proc. Natl. Acad. Sci. USA 99:6181, 1991; Russell et al., Transgenic Res. 6:157-68, 1997). The napin promoter has been shown to direct oleosin gene expression in transgenic Brassica, such that oleosin accumulates to approximately 1% of the total seed protein (Lee et al., Proc. Natl. Acad. Sci. USA 99:6181, 1991). In choosing a promoter, it may be desirable to use a tissue-specific or developmentally regulated promoter that allows suppression or overexpression in certain tissues without affecting expression in other tissues. "Tissue specific promoters" refer to coding regions that direct gene expression primarily in specific tissues such as, e.g., roots, leaves, stems, pistils, anthers, flower petals, seed coat, seed nucellus, or epidermal layers. Transcription stimulators, enhancers or activators can be integrated into tissue specific promoters to create a promoter with a high level of activity that retains tissue specificity. For instance, promoters utilized in overexpression will preferably be tissue-specific. Overexpression in the wrong tissue such as leaves, when attempting to overexpress in seed storage areas, could be deleterious. Particularly suitable promoters are those that allow for example seed-specific, root specific, leaf specific, fruit specific expression, and the like. This can be especially useful since seeds, roots, leaves and fruit are of particular interest. Some promoters specific for different tissue types are already available or can be isolated by well-established techniques (see, e.g., U.S. Pat. Nos. 5,792,925; 5,783,393; 5,859,336; 5,866,793; 5,898,096; and 5,929,302) and as further described below. Table 1 lists other embryo specific promoters that can be used to practice the present invention.

TABLE 1

Embryo Specific Promoters

| Promoter | Embryo | Endosperm | Timing | Reference |
| --- | --- | --- | --- | --- |
| oleosin from Arabidopsis | strong, uniform | none | traces at heart, higher early- to late-cotyledonary stage | Al et al., Plant Mol. Biol. 25: 193-205, 1994. |
| USP from Vicia faba | strong, uniform | none | early not known, strong in late cot. | Baumlein et al., Mol. Gen. Genet. 225: 459-467, 1991. |

TABLE 1-continued

Embryo Specific Promoters

| Promoter | Embryo | Endosperm | Timing | Reference |
|---|---|---|---|---|
| Legumin from *Vicia faba* | strong, preferential in cotyledons | aleurone layer (late) | early not known, strong in late cot. | Baumlein et al., supra 1991. |
| Napin from *Brassica* | ? | | late | Kohno-Murase, Plant Mol. Biol. 26: 1115-1124, 1994 |
| Albumin S1 from *Arabidopsis* | in axis only | none | early- to late-cotyledonary stage | Guerche et al., Plant Cell 2: 469-478, 1990 |
| Albumin S2 | in axis and cotyledons | none | early- to late-cotyledonary stage | Guerche et al., supra, 1990. |

In particular, embodiments to the present invention, a seed specific promoter that is particularily active during the development of the embryonic plant of an immature seed is of interest. Expression of a dominant negative mutant of the present invention early in seed development can be desirable so as to increase cell divisions early in seed development. More cell divisions at this stage can lead to larger embryos. Embryo composition is approximately 33% oil therefore a larger embryo will lead to increases in oil content. A promoter suitable for expression of the current invention in embryo and lower or no expression in other plant tissues is of interest to increase seed oil content. Of particular interest are those promoter sequences that initiate expression in early phase-specific embryo development. An early phase-specific promoter is a promoter that initiates expression of a protein prior to day 7 after pollination (walking stick) in *Arabidopsis* or an equivalent stage in another plant species. Examples of promoter sequences of particular interest include a promoter for the amino acid permease gene (AAP1) (e.g., the AAP1 promoter from *Arabidopsis thaliana*), a promoter for the oleate 12-hydroxylase:desaturase gene (e.g., the promoter designated LFAH12 from *Lesquerella fendleri*), a promoter for the 2S2 albumin gene (e.g., the 2S2 promoter from *Arabidopsis thaliana*), a fatty acid elongase gene promoter (FAE1) (e.g., the FAE1 promoter from *Arabidopsis thaliana*), and the leafy cotyledon gene promoter (LEC2) (e.g., the LEC2 promoter from *Arabidopsis thaliana*). The AAP1, LFAH12, 2S2, and FAE1 promoters are inactive in the earliest stage of embryo development. They become transcriptionally active at progressively later stages in development starting with AAP1 followed by LFAH12, 2S2, and then FAE. All four promoters then remain active through later embryonic development stages. The LEC2 promoter has an inverse expression profile. It is active in very early embryo development and then its activity declines gradually through later stages. Other embryo-specific promoters of interest include the promoters from the following genes: Seedstick (Pinvopich et al., *Nature* 424:85-88, 2003), Fbp7 and Fbp11 (Petunia Seedstick) (Colombo et al., *Plant Cell.* 9:703-715, 1997), Banyuls (Devic, *Plant J.,* 19:387-398, 1999), ABI3 (Ng et al., *Plant. Mol. Biol.* 54:25-38, 2004), agl-15, Agl18 (Lehti-Shiu et al., *Plant Mol. Biol.* 58:89-107, 2005), Phel (Kohler, *Genes Develop.* 17:1540-1553, 2003), emb175 (Cushing et al., *Planta.* 221:424-436, 2005), Ll1 (Kwong et al., *Plant Cell* 15:5-18, 2003), Lec1 (Lotan, *Cell* 93:1195-1205, 1998), Fusca3 (Kroj et al., *Development* 130:6065-6073, 2003), TT12 (Debeaujon et al., *Plant Cell* 13:853-871, 2001), TT16 (Nesi et al., *Plant Cell* 14:2463-2479, 2002), A-RZf (Zou and Taylor, *Gene* 196:291-295, 1997), TTG1 (Walker et al., *Plant Cell* 11:1337-1350, 1999), TT1 (Sagasser et al., *Genes Dev.* 16:138-149, 2002), TT8 (Nesi et al., *Plant Cell* 12:1863-1878, 2000), and Gea-8 (carrot) (Lin et al., *J. Exp. Botany* 50:1139-1147, 1999) promoters. Embryo specific promoters from monocots include Globulin, Knox (rice) (Postma-Haarsma, *Plant Mol. Biol.* 39:257-271, 1999), Oleosin (Plant, *Plant Mol. Biol.* 25:193-205, 1994), Keddie, *Plant Mol. Biol.* 24:327-340, 1994), Peroxiredoxin (Per1) (Haslekas et al., *Plant Mol. Biol.* 36:833-845, 1998), Haslekas et al., *Plant Mol. Biol.* 53:313-326, 2003), HvGAMYB (Diaz et al., *Plant J.* 29:453-464, 2002) and SAD1 (Isabel-LaMoneda et al., *Plant J.* 33:329-340, 1999) from Barley, and *Zea Maize* Hybrid proline rich protein promoters (Jose-Estanyol et al., *Plant Cell* 4:413-423, 1992; Jose-Estanyol et al., *Gene* 356:146-152, 2005).

Promoters of seed storage proteins are also of particular interest as seed storage proteins can represent up to 90% of total seed protein in many plants. The seed storage proteins are strictly regulated, being expressed almost exclusively in seeds in a highly tissue-specific and stage-specific manner (Higgins et al., *Ann. Rev. Plant Physiol.* 35:191-221, 1984; Goldberg et al., *Cell* 56:149-160, 1989). Moreover, different seed storage proteins may be expressed at different stages of seed development. Expression of seed-specific genes has been studied in great detail (see reviews by Goldberg et al., supra, and Higgins et al., supra). Examples of seed-specific promoters include LFAH12 of *Arabidopsis* and other plants, and the 5' regulatory regions of an *Arabidopsis* oleosin gene as described in U.S. Pat. No. 5,977,436 to Thomas et al. (incorporated in its entirety by reference), which when operably linked to either the coding sequence of a heterologous gene or sequence complementary to a native plant gene, direct expression of the heterologous gene or complementary sequence in a plant seed.

Suitable seed storage protein promoters for dicotyledonous plants include, for example, bean β-phaseolin, lectin, and phytohemagglutinin promoters (Sengupta-Gopalan, et al., *Proc. Natl. Acad Sci. U.S.A.* 82:3320-3324, 1985; Hoffman et al., *Plant Mol. Biol.* 11:717-729, 1988; Voelker et al., *EMBO J.* 6:3571-3577, 1987); rapeseed (Canola) napin promoter (Radke et al., *Theor. Appl. Genet.* 75:685-694, 1988); soybean glycinin and conglycinin promoters (Chen et al., *EMBO J.* 7:297-302, 1988; Nielson et al., *Plant Cell* 1:313-328, 1989, Harada et al., *Plant Cell* 1:415-425, 1989; Beachy et al., *EMBO J.* 4:3047-3053, 1985); soybean lectin promoter (Okamuro et al., *Proc. Natl. Acad. Sci. USA* 83:8240-8244, 1986); soybean Kunitz trypsin inhibitor promoter (Perez-Grau et al., *Plant Cell* 1:1095-1109, 1989; Jofuku et al., *Plant Cell* 1:1079-1093, 1989); potato patatin promoter (Rocha-Sosa et al., *EMBO J.* 8:23-29, 1989); pea convicilin, vicilin, and legumin promoters (Rerie et al., *Mol. Gen. Genet.* 259:148-157, 1991; Newbigin et al., *Planta* 180:461-470, 1990; Higgins et al., *Plant Mol. Biol.* 11:683-695, 1988; Shirsat et al., *Mol. Gen. Genetics* 215:326-331, 1989); and sweet potato sporamin promoter (Hattori et al., *Plant Mol. Biol.* 14:595-604, 1990).

For monocotyledonous plants, seed storage protein promoters useful in the practice of the invention include, e.g., maize zein promoters (Schernthaner et al., *EMBO J.* 7:1249-1255, 1988; Hoffman et al., *EMBO J.* 6:3213-3221, 1987 (maize 15 kD zein)); maize 18 kD oleosin promoter (Lee et al., *Proc. Natl. Acad. Sci. USA* 888:6181-6185, 1991); waxy promoter; shrunken-1 promoter; globulin 1 promoter; shrunken-2 promoter; rice glutelin promoter; barley hordein promoter (Marris et al., *Plant Mol. Biol.* 10:359-366, 1988); RP5 (Su et al., *J. Plant Physiol.* 158:247-254, 2001); EBE1 and 2 maize promoters (Magnard et al., *Plant Mol. Biol.* 53:821-836, 2003) and wheat glutenin and gliadin promoters (U.S. Pat. No. 5,650,558; Colot et al., *EMBO J.* 6:3559-3564, 1987).

Also suitable for practice of the present invention are promoters of genes for *B. napus* isocitratelyase and malate synthase (Comai et al., *Plant Cell* 1:293-300, 1989); delta-9 desaturase from safflower (Thompson et al., *Proc. Natl. Acad. Sci. USA* 88:2578-2582, 1991) and castor (Shanklin et al., *Proc. Natl. Acad. Sci. USA* 88:2510-2514, 1991); acyl carrier protein (ACP) from *Arabidopsis* (Post-Beittenmiller et al., *Nucl. Acids Res.* 17:1777, 1989), *B. napus* (Safford et al., *Eur. J. Biochem.* 174:287-295, 1988), and *B. campestris* (Rose et al., *Nucl. Acids Res.* 15:7197, 1987); β-ketoacyl-ACP synthetase from barley (Siggaard-Andersen et al., *Proc. Natl. Acad. Sci. USA* 88:4114-4118, 1991); and oleosin from *Zea mays* (Lee et al., *Proc. Natl. Acad Sci. USA* 88:6181-6185, 1991), soybean (Genbank Accession No. X60773) and *B. napus* (Lee et al., *Plant Physiol.* 96:1395-1397, 1991).

Other promoters useful in the practice of the invention are known to those of skill in the art. Moreover, known methods can be used to isolate additional promoters suitable for use in accordance with the present invention. For example, differential screening techniques can be used to isolate promoters expressed at specific (developmental) times, such as during fruit development.

Promoters of seed specific genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in *Arabidopsis* and *B. napus* seeds (Vandekerckhove et al., *Bio/Technology* 7:929-932, 1989), bean lectin and bean β-phaseolin promoters to express luciferase (Riggs et al., *Plant Sci.* 63:47-57, 1989), and wheat glutenin promoters to express chloramphenicol acetyl transferase (Colot et al., supra).

Attaining the proper level of expression of the nucleic acid fragments of the invention may require the use of different chimeric genes utilizing different promoters. Such chimeric genes can be transferred into host plants either together in a single expression vector or sequentially using more than one vector.

In addition, enhancers are often required or helpful to increase expression of the gene of the invention. It is necessary that these elements be operably linked to the sequence that encodes the desired proteins and that the regulatory elements are operable. Enhancers or enhancer-like elements may be either the native or chimeric nucleic acid fragments. This would include viral enhancers such as that found in the 35S promoter (Odell et al., *Plant Mol. Biol.* 10:263-272, 1988), enhancers from the opine genes (Fromm et al., *Plant Cell* 1:977-984, 1989), or enhancers from any other source that result in increased transcription when placed into a promoter operably linked to the nucleic acid fragment of the invention. For example, a construct may include the CaMV 35S promoter with dual transcriptional enhancer linked to the Tobacco Etch Virus (TEV) 5' non-translated leader. The TEV leader acts as a translational enhancer to increase the amount of protein made.

Suitable promoter elements, such as those described herein, can be fused to the mutant CKI nucleic acid sequences and a suitable terminator (polyadenylation region) according to well established procedure.

Transgenic Plants

In another aspect of the present invention, transgenic plants comprising a mutant CKI transgene are provided. Transgenic plants expressing a mutant CKI polypeptide can be obtained, for example, by transferring a transgenic vector (e.g., a plasmid or viral vector) encoding the mutant polypeptide into a plant. Typically, when the vector is a plasmid, the vector also includes a selectable marker gene such as, e.g., the neomycin phosphotransferase II (nptII) gene encoding resistance to kanamycin. The most common method of plant transformation is performed by cloning a target transgene into a plant transformation vector that is then transformed into *Agrobacterium tumifaciens* containing a helper Ti-plasmid as described in Hoeckema et al. (*Nature* 303: 179-181, 1983). The *Agrobacterium* cells containing the transgene vector are incubated with leaf slices of the plant to be transformed as described by An et al. (*Plant Physiology* 81:301-305, 1986). (See also Hooykaas, *Plant Mol. Biol.* 13:327-336, 1989). Transformation of cultured plant host cells is normally accomplished through *Agrobacterium tumifaciens*, as described above. Cultures of host cells that do not have rigid cell membrane barriers are usually transformed using the calcium phosphate method as originally described by Graham et al. (*Virology* 52:546, 1978) and modified as described in sections 16.32-16.37 of Sambrook et al., supra. However, other methods for introducing DNA into cells such as Polybrene (Kawai et al., *Mol. Cell. Biol* 4:1172, 1984), protoplast fusion (Schaffner, *Proc. Natl. Acad. Sci. USA* 77:2163, 1980), electroporation (Neumann et al., 1982 *EMBO J.* 1:841, 1982), and direct microinjection into nuclei (Capecchi, *Cell* 22:479, 1980) can also be used. Transformed plant calli can be selected through the selectable marker by growing the cells on a medium containing, e.g., kanamycin and appropriate amounts of a phytohormone such as naphthalene acetic acid and benzyladenine for callus and shoot induction. The plant cells can then be regenerated and the resulting plants transferred to soil using techniques well known to those skilled in the art.

In addition to the methods described above, a large number of methods are known in the art for transferring cloned DNA into a wide variety of plant species, including gymnosperms, angiosperms, monocots and dicots (see, e.g., *Methods in Plant Molecular Biology* (Glick and Thompson eds., CRC Press, Boca Raton, Fla., 1993); Vasil, *Plant Mol. Biol.* 25:925-937, 1994; and Komari et al., *Current Opinions Plant Biol.* 1:161-165, 1998 (general reviews); Loopstra et al., *Plant Mol. Biol.* 15:1-9, 1990; and Brasileiro et al., *Plant Mol. Biol.* 17:441-452, 1991 (transformation of trees); Eimert et al., *Plant Mol. Biol.* 19:485-490, 1992 (transformation of *Brassica*); Hiei et al., *Plant J.* 6:271-282, 1994; Hiei et al., *Plant Mol. Biol.* 35:205-218, 1997; Chan et al., *Plant Mol. Biol.* 22:491-506, 1993; U.S. Pat. Nos. 5,516,668 and 5,824,857 (rice transformation); and U.S. Pat. No. 5,955,362 (wheat transformation); U.S. Pat. No. 5,969,213 (monocot transformation); U.S. Pat. No. 5,780,798 (corn transformation); U.S. Pat. No. 5,959,179 and U.S. Pat. No. 5,914,451 (soybean transformation). Representative examples include electroporation-facilitated DNA uptake by protoplasts (Rhodes et al., *Science* 240:204-207, 1988; Bates, *Methods Mol. Biol.* 111:359-366, 1999; D'Halluin et al., *Methods Mol. Biol.* 111:367-373, 1999; U.S. Pat. No. 5,914,451); treatment of protoplasts with polyethylene glycol (Lyznik et al., *Plant Molecular Biology* 13:151-161, 1989; Datta et al., *Methods Mol. Biol.,* 111:335-334, 1999); and bombardment of cells with DNA laden microprojectiles (Klein et al., *Plant Physiol.* 91:440-444, 1989; Boynton et al., *Science* 240:1534-1538, 1988; Register et al., *Plant Mol. Biol.* 25:951-961, 1994; Barcelo et al., *Plant J.* 5:583-592, 1994; Vasil et al., *Methods Mol. Biol.* 111:349-358, 1999; Christou, *Plant Mol. Biol.* 35:197-203, 1997; Finer et al., *Curr. Top. Microbiol. Immunol.* 240:59-80, 1999). Additionally, plant transformation strategies and techniques are reviewed in Birch, *Ann Rev Plant Phys Plant Mol Biol.* 48:297, 1997; Forester et al., *Exp. Agric.* 33:15-33, 1997. Minor variations make these technologies applicable to a broad range of plant species.

In the case of monocot transformation, particle bombardment is typically the method of choice. However, monocots such as maize can also be transformed by using *Agrobacterium* transformation methods as described in U.S. Pat. No. 5,591,616 to Hiei et al. Another method to effect monocot transformation, e.g., corn, mixes cells from embryogenic suspension cultures with a suspension of fibers (5% w/v, Silar SC-9 whiskers) and plasmid DNA (1 µg/ul) and which is then placed either upright in a multiple sample head on a Vortex Genie II vortex mixer (Scientific Industries, Inc., Bohemia, N.Y., USA) or horizontally in the holder of a Mixomat dental amalgam mixer (Degussa Canada Ltd., Burlington, Ontario, Canada). Transformation is then carried out by mixing at full speed for 60 seconds (for example with a Vortex Genie II) or shaking at fixed speed for 1 second (Mixomat). This process results in the production of cell populations out of which stable transformants can be selected. Plants are regenerated from the stably transformed calluses and these plants and their progeny can be shown by Southern hybridization analysis to be transgenic. The principal advantages of the approach are its simplicity and low cost. Unlike particle bombardment, expensive equipment and supplies are not required. The use of whiskers for the transformation of plant cells, particularly maize, is described in, for example, U.S. Pat. No. 5,464,765 to Coffee et al.

U.S. Pat. No. 5,968,830 to Dan et al. describes methods of transforming and regenerating soybean. U.S. Pat. No. 5,969,215 to Hall et al., describes transformation techniques for producing transformed *Beta vulgaris* plants, such as the sugar beet.

Each of the above transformation techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest.

Traditional *Agrobacterium* transformation with antibiotic resistance selectable markers is problematical because of public opposition that such plants pose an undue risk-of spreading antibiotic tolerance to animals and humans. Such antibiotic markers can be eliminated from plants by transforming plants using the *Agrobacterium* techniques similar to those described in U.S. Pat. No. 5,731,179 to Komari et al. Antibiotic resistance issues can also be effectively avoided by the use of bar or pat coding sequences, such as is described in U.S. Pat. No. 5,712,135. These preferred marker DNAs encode second proteins or polypeptides inhibiting or neutralizing the action of glutamine synthetase inhibitor herbicides phosphinothricin (glufosinate) and glufosinate ammonium salt (Basta, Ignite).

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

There are numerous factors that influence the success of transformation. The design and construction of the exogenous gene construct and its regulatory elements influence the integration of the exogenous sequence into the chromosomal DNA of the plant nucleus and the ability of the transgene to be expressed by the cell. A suitable method for introducing the exogenous gene construct into the plant cell nucleus in a non-lethal manner is essential. Importantly, the type of cell into which the construct is introduced must, if whole plants are to be recovered, be of a type which is amenable to regeneration, given an appropriate regeneration protocol.

Methods of Use

In accordance with another aspect of the present invention, cell division in a plant cell is modulated, e.g., increased. Plant cells amenable to modulation, such as an increase of cell division using the methods described herein, are plant cells that express a wild-type CKI polypeptide having separate cyclin and CDK binding regions. Generally, the methods include expressing within the plant cell a mutant CKI polypeptide as described herein, and allowing the mutant CKI polypeptide to inhibit wild-type CKI biological activity within the plant cell. The mutant CKI polypeptide is expressed from a recombinant nucleic acid encoding the mutant protein. Further, in certain embodiments, the method further includes introducing into the plant cell the recombinant nucleic acid encoding the mutant CKI polypeptide. Recombinant nucleic acids encoding mutant CKI polypeptides, including construction of such recombinant molecules and their introduction into plant cells, are described generally supra, and are further exemplified in the Examples, infra. Modulation of cell division can be carried out in a plant cell either in vivo, such as described herein above with respect to transgenic plants. Alternatively, the method can be performed in a plant cell in vitro.

As described herein above, the mutant CKI polypeptide includes a CKI amino acid sequence having at least one modification relative to a reference CKI polypeptide. With respect to the method for modulation of cell division, the reference CKI polypeptide can be either the wild-type plant CKI polypeptide expressed within the plant cell in which modulation of cell division is to be carried out (typically the endogenous wild-type CKI). Alternatively, because use of a mutant CKI protein as described herein can allow for dominant negative antagonist activity against structural homologues or family members of the wild-type CKI from which the mutant is derived, the reference CKI polypeptide can be a wild-type CKI polypeptide heterologous to the wild-type CKI polypeptide expressed with the plant cell and which is capable of providing substantially equivalent wild-type function. Thus, in some cases, a mutant CKI protein, not derived from the endogenous CKI protein, is expressed within a plant cell to inhibit endogenous wild-type CKI function (e.g., a mutant CKI polypeptide derived from an *Arabidopsis thaliana* wild-type KRP protein can be used to inhibit wild-type KRP function in non-heterologous plant cells such as, for example, *Brassica napus, Glycine max,* Maize cells and the like). Other heterologous mutant CKI polypeptides derived from other plants, such as *Brassica napus,* and the like, can also be used.

Further, in certain embodiments of the method, a plurality of related CKIs are simultaneously inhibited within a plant cell using a mutant CKI of the present invention. For example, in some embodiments, all endogenous CKIs within a family (e.g., KRP family members) are simultaneously inhibited. As noted above, a mutant CKI protein as described herein allows for dominant negative antagonist activity within structural homologues or family members of the wild-type CKI from which the variant is derived, thereby allowing for such simultaneous inhibition of multiple homologues or family members. Thus, in typical embodiments, a plurality of (and preferably all) CKIs having substantial sequence identity or similarity within the targeted CDK or cyclin binding region are inhibited within a plant cell. For example, in certain embodiments, as KRP family members share substantial sequence identity within the CDK binding region, which is primarily responsible for inhibition of cyclin-CDK kinase activity, a plurality of, and preferably all, endogenous KRP family members within a plant cell are inhibited via expression of a mutant KRP CKI so as to modulate cell division.

As described above, by effectively blocking endogenous CKI proteins from inhibiting cyclin/CDK activities, cell division within a plant cell is modulated. Such modulation includes acceleration of progression through the cell cycle and, ultimately, increased cellular proliferation. Accordingly, using the methods set forth herein in vivo (e.g., transgenic plants, see supra), an increase in crop yields and/or seed size, increased plant vigor, increased root mass, increased fruit size, and the like can be achieved.

Increased crop yield can manifest itself in a variety of forms depending on the specific plant tissue and plant species in which the plant cell cycle has been modulated by blocking endogenous CKI proteins from inhibiting cyclin/CDK activities.

In seed crops such as corn, rice, wheat, barley, soybean, canola, increased yield can take the form of increased total seed number, increased seed size, or both increased seed number and seed size. In one embodiment, increased yield is obtained in transgenic varieties of any of the seed crops by expressing a transgene encoding a mutant CKI protein resulting in increased cell division and increased total seed number, larger seeds, or both increased seed number and seed size. In one embodiment, expression of the mutant CKI protein transgene is controlled by a constitutive promoter. In another exemplary embodiment, expression of the mutant CKI protein transgene is controlled by a seed-specific promoter targeting the effect of the mutant CKI protein to the seed which is the agronomically important component of a seed crop.

For oilseed crops such as soybean, canola, camelina, flax, corn, safflower, or sunflower, and the like, where the desired product is oil, increased yield takes the form of greater oil yield per plant. Oil is derived from the embryo in the seed. In one embodiment, increased oil yield is obtained in transgenic varieties of any of the oilseed crops by expressing a transgene encoding a mutant CKI protein causing increased cell division leading to increased total seed number, increased embryo size, or both increased seed number and embryo size. Increased total seed number per plant results in increased total oil yield per plant. Increased embryo size results in greater oil content per seed and increased total oil yield per plant. In a preferred embodiment; expression of the mutant CKI protein transgene is controlled by an embryo-specific promoter giving increased cell division in early embryo development resulting in a larger embryo, an increased oil quantity per seed, and a corresponding increase in total oil yield per plant.

Non-seed biomass production is the main yield component of crops such as alfalfa, lettuce, tobacco, eucalyptus, and poplar. Increased yield in such crops would be seen in increased overall growth of the plant resulting in enhanced accumulation of biomass. In one embodiment, increased biomass is obtained in transgenic varieties of any of the biomass crops by expressing a transgene encoding a mutant CKI protein causing increased cell division leading to increased growth and biomass. In one embodiment, expression of the mutant CKI protein transgene is controlled by a promoter giving constitutive expression of the mutant CKI protein encoding transgene in most or all the tissues of the plant. In a preferred embodiment, expression of the mutant CKI protein transgene is controlled by a tissue-specific promoter targeting expression of the transgene to the agronomically important component of the plant such as the leaf in lettuce or tobacco or the trunk in eucalyptus or poplar to increase biomass accumulation in the target tissue.

Sugar or cellulose is the primary yield component of crops grown for production of ethanol including sugarcane, sugar beet, corn, and switchgrass. In one embodiment, increased sugar is obtained in transgenic varieties of any of the sugar producing crops such as sugarcane or sugar beet by expressing a transgene encoding a mutant CKI protein causing increased cell division, increased growth of the sugar accumulating tissue of the plant, and increased total sugar content per plant. In one embodiment, expression of the mutant CKI protein transgene in sugar producing crops is controlled by a promoter giving constitutive expression of the mutant CKI protein encoding transgene in most or all the tissues of the plant. In a preferred embodiment, expression of the mutant CKI protein transgene is controlled by a tissue-specific promoter targeting expression of the transgene to the sugar accumulating tissue of the plant such as the cane in sugarcane or the root in sugar beet thereby increasing cell proliferation and growth of the sugar storage and accumulation tissue of the plant resulting in increased total sugar content. In another embodiment, increased cellulose is obtained in transgenic varieties of any of the cellulose producing crops such as corn or switchgrass by expressing a transgene encoding a mutant CKI protein causing increased cell division and cell wall synthesis thereby increasing the content of cellulose which is a component of the cell wall. In one embodiment, expression of the mutant CKI protein transgene is controlled by a promoter giving constitutive expression of the mutant CKI protein encoding transgene in most or all the tissues of the plant. The consequent general increase in cell proliferation results in increased cell wall deposition and therefore increased total cellulose content of the plant.

EXAMPLES

The following examples are offered to illustrate, but not to limit, the claimed invention.

Example 1

Production/Purification of an Active Cyclin:CDK Complex and the Production/Purification of Krp Molecules Insect Cells and Media The baculovirus expression system is a versatile eukaryotic system for heterologous gene expression. This system provides correct protein folding, disulfide bond formation and other important post-translational modifications. All methods were taken from the *Baculovirus expression vector system*: Procedures and methods manual. (BD Biosciences, Pharmingen, San Diego, Calif. 6th ed.). Sf9 insect cells were grown at 27° C. in TNM-FH insect cell media (BD Biosciences) for the reported studies. It should be noted that alternative media are well known to the skilled artisan and are also useful. Similarly, alternative insect cell lines such as Sf21 and High Five TM cells will also work for virus production and protein production.

Western Blot and Immunoprecipitations.

The recombinant protein expressed in insect cells was monitored by Western blot. Protein extracts (35 μg) were boiled in the presence of Laemmli buffer, run on 10% or 12% SDS-PAGE gels and transferred to a PVDF membrane using a submerged transfer apparatus (BioRad). Following the transfer, the membrane was blocked in TBS-T (25 mM Tris pH 7.5; 75 mM NaCl; 0.05% Tween) containing 5% non-fat dry milk powder. Primary antibody was used at 1:1000 dilution overnight in TBS-T blocking buffer. Blots were washed three times 15 minutes at room temperature. An appropriate secondary antibody conjugated to horse radish peroxidase (HRP) was used at 1:10,000 dilution in TBS-T blocking buffer. Blots were incubated in secondary antibody for 1 hour and then washed three times in TBS-T, 15 min. each. Blots were then processed as described in the ECL system protocol (Amersham Biosciences). Antibodies commonly used were: anti-flag M2 monoclonal antibody (Sigma), anti-HA monoclonal or polyclonal antibody (Babco), anti-PSTAIR antibody (Sigma-Aldrich), anti-myc monoclonal or polyclonal (A-14) (Santa Cruz Biotechnology). Secondary antibodies used were anti-mouse IG-HRP, and anti-rabbit IG-HRP (GE Healthcare).

Immunoprecipitations were routinely performed to monitor complex formation between AtCyclinD2;1, AtCDKA and Krp molecules. Protein extracts (14 μg) were diluted in 0.5 ml binding buffer (100 mM Sodium Phosphate buffer pH 7.0, 150 mM NaCl, 1% Triton 100 plus protease inhibitors). Protein/antibody mixture was rocked gently at 4° C. for about two hours and then the appropriate antibody was added. (2 μg of anti-flag M2 antibody; 5 μl of anti-HA antibody; 5 μl of anti-myc polyclonal). Protein A sepharose was added to give a 10 μl bed volume. Immunoprecipitates were gently mixed for 1 hour at 4° C. and then washed 3 times with 1 ml of binding buffer. Protein complexes bound to the Protein-A sepharose beads were then boiled in the presence of Laemmli buffer. Protein complexes were resolved on either 10% or 12% SDS-PAGE gels and transferred to PVDF membrane. Membranes were blotted as described above.

Baculovirus Vector Construction

*Arabidopsis* cyclin D2;1 (AtcyclinD2;1) and *Arabidopsis* CDKA (AtCDKA) cDNA sequences were epitope tagged and cloned into a baculovirus transfer vector (BD Biosciences). Other transfer vector systems known to the artisan can also be used. AtCyclinD2;1 was tagged with the FLAG epitope (Sigma-Aldrich) on the N-terminus by adding Met Asp Tyr Lys Ala Phe Asp Asn Leu (MDYKAFDNL) amino acid sequence (SEQ ID No.:18) by PCR and then cloned into the pAcHLT transfer vector (BD Biosciences). Other Baculovirus transfer vector systems such as Baculodirect (Invitrogen), can also be used for this purpose. The hemagglutinin (HA) epitope amino acid sequence Tyr Pro Tyr Asp Val Pro Asp Tyr Ala (YPYDVPDYA; SEQ ID NO:19) was placed in frame with the 5' end of AtCDKA by PCR and then cloned into the pVL1393 transfer vector (AB Vector, CA). The cyclin and CDK were epitope tagged to enable identification by Western blot and for immunoprecipitation experiments. The cyclin and or the CDK can also be used lacking the tags. Other compatible transfer vector systems can also be used.

Recombinant Virus Production

The Baculovirus genome used is Baculogold Bright Baculovirus (BD Biosciences). Alternative Baculovirus genomes can also be used. The Flag tagged version of AtcyclinD2;1 was introduced into a nonessential region the baculovirus viral genome using homologous recombination. Homologous recombination occurred when the transfer vector containing cyclin D2;1 was co-transfected with the linearized BD Baculogold Bright Baculovirus DNA into Sf9 insect cells. Sf9 cells were seeded at 2×10$^6$ cells on 60 mm dish and transiently co-transfected with 2 μg cyclin D2;1 transfer vector (pAcHLT-cyclinD2;1) plus 0.5 μg linearized BD Baculogold Bright Baculovirus DNA using Fugene 6 transfection reagent according to manufacturer's protocol (Roche Diagnostics). After 4 hours of transfection the Fugene/DNA solution was removed and replaced with 3 ml of TNM-FH media. Four (4) days later, the supernatant was collected and subsequently used to infect more cells for amplification of the virus. This amplification was repeated until the virus titer was at least 10$^9$ virus particles/ml. The virus was amplified by infecting Sf9 cells at a multiplicity of infection (moi) of <1. The virus titer was monitored using light and fluorescence microscopy.

The HA tagged version of AtCDKA 1 was introduced into a nonessential region the baculovirus viral genome using homologous recombination. Homologous recombination occurred when the transfer vector containing cyclin D2;1 was cotransfected with the linearized BD Baculogold Bright Baculovirus DNA into Sf9 insect cells. Sf9 cells were seeded at 2×10$^6$ cells on 60 mm dish and transiently co-transfected with 2 μg AtCDKA transfer vector (pVL1393-AtCDKA) plus 0.5 μg linearized BD Baculogold Bright Baculovirus DNA using Fugene 6 transfection reagent according to the manufacturer's protocol (Roche Diagnostics). After 4 hours of transfection the Fugene/DNA solution was removed and replaced with 3 ml of TNM-FH media. Four (4) days later, the supernatant was collected and subsequently used to infect more cells for virus amplification. This amplification was repeated until the virus titer was at least 10$^9$ virus particles/ml. The virus was amplified by infecting Sf9 cells at a multiplicity of infection (MOI) of <1. The virus titer was monitored using light and fluorescence microscopy.

Recombinant Protein Production in Insect Cells.

Production of Flag tagged AtcyclinD2;1 protein: Tagged AtcyclinD2;1 was achieved by infecting *S. frugiperda* Sf9 cells with AtcyclinD2;1 baculovirus. To this end, Sf9 cells were grown in suspension at 2×10$^6$/ml were infected with recombinant baculovirus at an MOI>5 (but other higher or slightly lower MOIs will also work) for about 4 to 5 days and then harvested. Cells were collected and centrifuged at 3000 rpm at 4° C. The cell pellet was washed with fresh media and then centrifuged at 3000 rpm at 4° C. The pellet was frozen at −80° C. or immediately lysed. Lysis buffer consisted of 20 mM Hepes pH 7.5, 20 mM NaCl, 1 mM EDTA, 20% glycerol, 20 mM MgCl$_2$ plus protease inhibitors (Complete Mini, EDTA free, Boehringer Mannheim), 1 tablet per 10 ml lysis buffer. The cell lysate was sonicated on ice 2 times for 15 seconds. Protein lysate was then centrifuged at 40,000 rpm in a Beckman TLA 100.2 rotor for 2 hours. The supernatant containing the tagged AtCyclinD2;1 was aliquoted and frozen at −20° C. Expression was monitored by Western blot using anti-Flag M2 monoclonal antibody (Sigma-Aldrich).

Production of tagged AtCDKA was achieved by infection of *S. frugiperda* Sf9 cells with AtCDKA baculovirus and processed in the same manner as described above. Expression was monitored by Western blot using anti-HA monoclonal or polyclonal antibody (Babco). Expression can also be monitored by Western blot using anti-PSTAIR antibody (Sigma-Aldrich).

An active kinase complex of AtcyclinD2;1/AtCDKA was prepared by co-infecting of *S. frugiperda* Sf9 cells with AtcyclinD2;1 (MOI>5) plus AtCDKA (MOI>5) baculovirus. The active complex was purified as described above. Protein expression was monitored by Western blot of insect cell extacts using anti-Flag M2 antibody or anti-HA antibody. The interaction of AtcyclinD2;1 and AtCDKA was monitored by co-immunoprecipitation as described infra.

Kinase Assay

An in vitro assay was developed to test various KRP/ICK molecules ability to inhibit cyclin/CDK complexes.

Kinase activity in protein extracts from insect cells infected with individual baculovirus or a co-infection with the two baculovirus was monitored with a standard kinase assay. Histone HI (HHI) was the principle substrate used but recombinant tobacco retinoblastoma protein (Nt Rb) could also be used as the substrate (see Koroleva et al., *Plant Cell* 16, 2346-79, 2004). Kinase assays were performed as follows: 7 µg of insect cell protein extract was added to a kinase buffer cocktail (KAB: 50 mM Tris pH 8.0, 10 mM $MgCl_2$, 10 µM ATP plus 0.5 µCi/ml$^{32}$PγATP and 2 µg of HHI) to a final volume of 30 µl. The reactions were incubated at 27° C. for 30 minutes. The kinase reaction was stopped with an equal volume (30 µl) of 2× Laemmli buffer. [$^{32}$P] phosphate incorporation was monitored by autoradiography and/or Molecular Dynamics PhosphorImager following SDS-PAGE on 12% gels. Alternative buffer conditions for performing CDK kinase assays can also be used. (See, e.g., Wang and Fowke, *Nature* 386:451-452, 1997; Azzi et al., *Eur. J. Biochem.* 203:353-360, 1992; Firpo et al., *Mol. Cell. Biol.* 14:4889-4901, 1994.)

Results: Protein extract from insect cells infected with AtcyclinD2;1 alone or AtCDKA alone showed no kinase activity using HHI as the substrate. Insect cells co-infected with AtcyclinD2;1 virus and AtCDKA virus contained a robust kinase activity. Active CDK-like (cdc2-like) kinases can also be purified from plant protein tissue extracts or from plant tissue culture cell extracts by using p13suc1 agarose beads (See Wang and Fowke, *Nature* 386:451-452, 1997; Azzi et al., *Eur. J. Biochem.* 203:353-360, 1992) and used in a similar assay described above and in competition experiments described below in Examples 2 through 8.

Cloning of Krp cDNAs into Bacterial Expression Vector.

AtKrp1 Cloning

AtKrp1 cDNA was cloned from *Arabidopsis* cDNA by PCR using the following oligonucleotides:

```
(start)
                                        (SEQ ID NO: 20)
5' ATGGTGAGAAAATATAGAAAAGCT-3';

(end)
                                        (SEQ ID NO: 21)
5'-TCACTCTAACTTTACCCATTCGTA-3'.
```

The resulting PCR fragment was subcloned into pCRII-TOPO vector (Invitrogen). The resulting vector AtKrp1 #359 was sequenced to verify correct sequence to GenBank# U94772.

5' RACE of *Brassica napus* Krp1 Cloning

Blastn was used at the National Center for Biotechnology Information website to find *Brassica* sequences homologous to AtKRP1 cds. The search yielded two EST candidates, CD820320 and CD829052, which turned out to be identical sequences. CD820320 was taken through Jorja's blastx to verify that the translated nucleotide sequence of the EST significantly matched the At KRP1 protein sequence.

CD829052 is 646 bp and includes the last 106 amino acids of a *Brassica oleracea* KRP1 sequence and 321 bp of the 3' UTR. A 5' RACE primer (GSP1brasskrp1_5'RACE: 5'-CTCTGATAATTTAACCCACTCGTAGCGTCCT-TCTAATGGCTTCTC-3'; SEQ ID NO:22) was designed to retrieve a full-length Bn KRP1. The RACE primer contained the last 45 nucleotides of the coding sequence of CD820320.

5' RACE-ready cDNA was made from *Brassica napus* DH12075 leaf using the SMART RACE cDNA Amplification Kit (Clontech). 5' RACE was performed on this cDNA according to the kit instructions, except that pfu enzyme and buffer (Stratagene) were used instead of Klentaq. The PCR conditions were: an initial denaturation at 94° C. for 5 min, followed by 35 cycles of 94° C. for 5 sec, 68° C. for 10 sec, 72° C. for 3 min. The resulting PCR product was a very faint band of approximately 600 bp. 2.5 µl of this PCR product was then re-amplified using the above PCR conditions. The resulting PCR product was cloned into TOPO Blunt vector (Invitrogen) and transformed into alpha gold cells (Bioline). Plasmid DNA from two transformants were recovered and the inserts sequenced with M13 forward and reverse primers. The sequence of one candidate insert was identical to CD820320 and was designated Bn KRP1-II (no additional new sequences came from the RACE). The sequence of the other candidate insert, designated Bn KRP1-I, was 94% identical to Bn KRP1-II at the nucleotide level in the coding region, and 86% identical at the amino acid level for the last 106 residues. The RACE retrieved the full coding sequence of Bn KRP1-I with an additional 108 bp of 5' UTR in TOPO Blunt vector (pTG313). The BnKrp1 coding sequence (SEQ ID NO:23) is shown below:

```
  1 atggtgagaaaatgcagaaaaactaaagggacggtgggagctt   80
    cgtctacgtatatgcagcttcgcagccggagaatcgt 81 ttacagatcggaaaaagctagctcgtcgtcgtcttgttgcg  160
    cgagtaacaacaatggagttatagatcttgaggagg 161 aaagagatggtgagactgaaacgtcgtcgtgtcgacggagtag  240
    taagaggaagctatttgaaaaccttagagaaaaagaa 241 tctatggagaattcacagcaaatcgtagctggttttgattccgc  320
    cgtgaaagaatcatcggattgttgttgcagccgag 321 aacatctttgtcaacgacggaggagaaggggaaatcagcgacg  400
    gagcaaccaccaacggcagtggagattgaagattttt 401 tcgtggaagctgagaaacagctccatgataatttcaagaagaa  480
    gtataactttgatttcgaaaaggagaagccattagaa 481 ggacgctacgagtgggttaaattatcagagtaa            513
```

The pET16b bacterial expression vector contains the sequence encoding 6 Histidines (6×His, or (His)6 or hexa-His) in a row to enable protein purification by immobilized metal affinity chromatography (Novagen). This vector was modified in such a way to also include a poly-Myc epitope immediately downstream and in frame with the 6×His coding sequence (pET16b-5MYC). Full length AtKrp1 cDNA was amplified from pTG #359 TopoIIAtKrp1 cds using two oligonucleotides that flank the entire coding sequence. These oligonucleotides contained restriction enzyme sites that facilitate cloning into the pET16B-5MYC vector (5'AtKrp1 Bam HI/NdeI: ACGGATCCCATATGGT-GAGA AAATATAG (SEQ ID NO:24) and 3'AtKrp1XhoI: ATCGCTCGAGTCACTCTAACTTTAC (SEQ ID NO:25). The resulting PCR fragment was subcloned into the BamHI and XhoI site of pET16b-5myc. The resulting vector AtKrp #385 contained the AtKrp1 wild-type cDNA in frame with the 6×His and myc tags.

The following two oligonucleotides were used to amplify the BnKrp1 cDNA that adds a 5' BamHI/NdeI site and XhoI restriction site on the 3' end of BnKrp1 (5' BnKrp1 ACG-GATCCCATATGGTGAGAAAATGC (SEQ ID NO:26) and 3' BnKrp1 XhoI: ATCGCTCGAGTCACTCTGATAATT-TAAC (SEQ ID NO:27). The PCR fragment was amplified from pTG #313 (TopoII BnKrp1) and subcloned into the BamHI and XhoI site of pET16b-5myc and sequenced. The resulting vector BnKrp #461 contained the BnKrp1 wild-type cDNA in frame with the 6×His and myc tags.

Recombinant Krp Protein Expression in Bacteria and Purification.

All bacterial expression plasmids pET16b and pET16b-5MYC carrying inserts were transformed into BL21 Star (DE3) (Invitrogen). Bacterial colonies from this fresh transformation was used to inoculate 400 ml of LB containing 100 μg/ml of ampicillin and grown at 37° C. When the culture reached an $OD_{600}$ between 0.6 and 0.8 recombinant protein expression was induced with 0.5 mM isopropyl-D-thiogalactopyranoside (IPTG). Cells were then grown at 30° C. for three hours. Cells were collected by centrifugation in a JLA 10.500 Beckman rotor. Bacterial cell pellet was either stored at −80° C. or lysed immediately. Bacteria were lysed in 10 ml Phosphate lysis buffer (100 mM Phosphate buffer pH 7.0, 150 mM NaCl, 1% Triton X100] containing protease inhibitors and lacking EDTA. The resuspended bacterial culture was sonicated 4×20 seconds on wet ice at 40% power. Lysed cells were centrifuged at 14,000 rpm in Beckman JA20.1 rotor for 15 minutes at 4° C. Cell pellet was washed with 10 mls of Phosphate lysis buffer and the cell pellet was again collected by centrifugation. Tagged KRP molecules were mainly insoluble. Insoluble tagged KRP's were solubilized in Urea buffer (8M Urea, 100 mM Tris pH 7.5). The resuspended cell pellet was briefly sonicated 3×15 seconds on wet ice at 40% power. Urea-insoluble proteins were eliminated by centrifugation at 14,000 rpm in Beckman JA20.1 rotor for 15 minutes at 4° C. Tagged KRPs were purified in batch using BD Talon $Co^{2+}$ metal affinity resin equilibrated in Urea buffer. Batch purification was incubated at 4° C. 3 hrs to overnight under slow rotation. Slurry was loaded on a column and resin was washed with 36 bed volumes of Urea buffer followed by a 12 bed volumes of Urea buffer containing 5 mM Imidazole pH 7.5. Bound tagged KRP protein was eluted using Urea buffer containing 300 mM Imidazole pH 7.5. Fractions were monitored for tagged KRP by SDS-Page and/or by Bradford protein assay (BioRad). Refolding of the denatured tagged KRP1 was carried out using step-wise dilution dialysis. Fractions containing the majority of tagged KRP protein were combined and dialyzed in a 1M Urea, 100 mM Tris pH7.5, 150 mM NaCl and 5 mM β-mercaptoethanol plus 5 mM benzamidine for 20 hrs at 4° C. Dialysis buffer was then changed to 0.5 M Urea, 100 mM Tris pH 7.5, 150 mM NaCl and 5 mM β-mercaptoethanol plus 5 mM benzamidine and continued for an additional 12 hrs. Recombinant protein was collected, quantified by Bradford assay and stored at 4° C.

Mutagenesis of Krps.

The wild-type versions of AtKRP family members and BnKRP family members were subcloned into the basic pCRII-TOPO vector (Invitrogen) for sequencing and mutagenesis purposes.

The same AtKRP1 wild-type cDNA PCR fragment containing the engineered 5'-BamHI site and the 3' XhoI site (see "Cloning of Krp cDNAs into bacterial expression vector," supra) was subcloned into pCRII-TOPO vector (Invitrogen) for mutagenesis. The resulting vector Topo-AtKrp #385B contained the AtKRP1 wild-type cDNA and was verified for correct sequence using standard automated sequencing. The same BnKRP1 wild-type cDNA fragment from above was subcloned into pCRII-TOPO vector (Invitrogen) for mutagenesis. The resulting vector Topo-BnKrp #539 contained the BnKRP1 wild-type cDNA and was verified for correct sequence using standard automated sequencing analysis.

Site directed mutagenesis was performed according to the protocol for Stratagene's QuikChange site-directed mutagenesis kit.

To construct BnKrp1#462 with multiple amino acids substitutions in the putative cyclin binding region (E129A, E130A, I131A, D132A) the sense BnKrp1DbleMut#1 (GGA GCAACCACCAACGGCAGTGGCTGCTGCT-GCTTTTTTCGTG; SEQ ID NO:28) and anti-sense BnKrp1DbleMut#1b (CACGAAAAAAGCAGCAGCA-GCCACTGCCGTTGGTGGT TGCTCC; SEQ ID NO:29) were used for QuikChange site-directed mutagenesis with TopoBnKrp#539 as the template. The mutagenesis product was sequenced to verify presence of desired mutations. The mutant product was then subcloned into the BamHI/XhoI site of pET16b-5MYC to ultimately yield BnKrp1#462.

To construct BnKrp1#512 with two amino acids substitutions in the highly conserved residues of the CDK binding region (F151A, F153A) the sense BnKrp1DbleMut#2 oligonucleotide (CCTTCTAATGGCTTCTCCTTTTCAG-CATCAGCGTTATACTTCTTCT TGAA; SEQ ID NO:30) and anti-sense BnKrp1DbleMut#2b oligonucleotide (TTCAAGAAG AAGTATAACGCTGATGCT-GAAAAGGAGAAGCCATTAGAAGG; SEQ ID NO:31) were used for QuikChange site-directed mutagenesis with TopoBnKrp#539 as the template. The mutagenesis product was sequenced to verify presence of desired mutations and then subcloned into the BamHI/XhoI site of pET16b-5MYC. The same amino acid substitutions were also introduced into AtKRP1 using AtKrp1-Topo #385B as the template using the following oligonucleotides "QC ICK1 cds F173A, F175A-coding" 5'-TTCAAGAAGAAGTA CAAT-GCCGATGCCGAGAAGGAGAAGCCATTA-3'; (SEQ ID NO:32) and "QC ICK1cds F173A, F175A-noncod" 5'-TTATGGCTTCTCCTTCTGGGCATCGGCATTGTACT-TCTTC TTGAA-3' (SEQ ID NO:33).

For BnKrp1#463 with amino acids substitutions of the putative cyclin binding region and highly conserved residues in the CDK binding region (E129A, E130A, I131A, D132A,+F151A, F153A) the sense BnKrp1DbleMut#2 oligonucleotide ((CCTTCTAAT GGCTTCTCCTTTTCAG-CATCAGCGTTATACTTCTTCTTGAA; SEQ ID NO:30) anti-sense BnKrp1DbleMut#2b oligonucleotide (TTCAAGAAGAAGTATAACGCTGATGCTG AAAAGGAGAAGCCATTAGAAGG; SEQ ID NO:32) were used for QuikChange site-directed mutagenesis with BnKrp#462 as the template. The mutagenesis product was sequenced to verify presence of desired mutations and then subcloned into the BamHI/XhoI site of pET16b-5MYC.

To construct BnKrp1#586 with a single amino acids substitution in the CDK binding region (K148A) the sense BnKrp1K148A oligonucleotide (GATAATTTCAAGAAG GCGTATAACTTTGATTTC; SEQ ID NO:34) and anti-sense BnKrp1K148A oligonucleotide (GAAATCAAAGT-TATACGCCTTCTTGAAATTATC; SEQ ID NO:35) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#587 with a single amino acids substitution in the CDK binding region (Y149A) the sense BnKrp1Y149A oligonucleotide (AATTTCAAGAAGAAG GCTAACTTTGATTTCGAA; SEQ ID NO:36) and anti-sense BnKrp1Y149A oligonucleotide (TTCGAAAT-CAAAGTTAGCCTTCTTCTTGAAATT; SEQ ID NO:37) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#588 with a single amino acids substitution in the CDK binding region (N150A) the sense BnKrp1N150A oligonucleotide (TTCAAGAAGAAGTAT GCCTTTGATTTCGAAAAG; SEQ ID NO:38) and anti-sense BnKrp1N150A oligonucleotide (CTTTTCGAAAT-CAAAGGCATACTTCTTCTTGAA; SEQ ID NO:39) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#572 with a single amino acids substitution in the CDK binding region (F151A) the sense BnKrp1F151A oligonucleotide (AGAAGAAG-TATAACGCTGATTTCGGAAAGGA; SEQ ID NO:40) and anti-sense BnKrp1F151A oligonucleotide (TCCTTTTC-GAAATCAGCGTTATACTTCTTCT; SEQ ID NO:41) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#573 with a single amino acids substitution in the CDK binding region (F153A) the sense BnKrp1F153A oligonucleotide (AGTATAACTTTGATGC-CGAAAAGGAGAAGCC; SEQ ID NO:42) and anti-sense BnKrp1F153A oligonucleotide (GGCTTCTCCTTTTCG-GCATCAAAGTTATACT; SEQ ID NO:43) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#553 with two amino acids substitutions in the CDK binding region (K157A; P158A) the sense BnKrp1KP→AA oligonucleotide (GATTTC-GAAAAGGA GGCGGCATTAGAAGGACGCT; SEQ ID NO:44) and anti-sense BnKrp1KP→AA oligonucleotide (AGCGTCCTTCTAATGCCGCCTCCTTTTCGAAATC) (SEQ ID NO:45) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#554 with two amino acids substitutions in the CDK binding region (R162A;Y163A) the sense BnKrp1RY→AA oligonucleotide (GCCATTA-GAAGGA GCCGCCGAGTGGGTTAAATT; SEQ ID NO:46) and anti-sense BnKrp1RY→AA oligonucleotide (AATTTAACCCACTCGGCGGCTCCTTCTAATGGC; SEQ ID NO:47) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#555 with two amino acids substitutions in the CDK binding region (E164A;W165A) the sense BnKrp1EW→AA oligonucleotide (AGAAGGACGC-TAC GCGGCGGTTAAATTATCAGA; SEQ ID NO: 48) and anti-sense BnKrp1EW→AA oligonucleotide (TCTGA-TAATTTAACCGCCGCGTAGCGTCCTTCT; SEQ ID NO: 49) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#556 with two amino acids substitutions in the CDK binding region K167A; L168A) the sense BnKrp1KL→AA oligonucleotide (CGCTAC-GAGTGGGT TGCAGCATCAGAGTGAGAGC; SEQ ID NO: 50) and anti-sense BnKrp1KL→AA oligonucleotide (GCTCTCACTCTGATGCTGCAACCCACTCGTAGCG; SEQ ID NO:51) were used for QuikChange site-directed mutagenesis with TopoBnKrp#539 as the template. The mutagenesis product was sequenced to verify presence of desired mutations and then subcloned into the BamHI/XhoI site of pET16b-5MYC.

To construct BnKrp1#574 with multiple amino acid substitutions in the CDK binding region (F151A;F153A; E164A;W165A) the BnKrp1F151A, F153A oligonucleotide (CCTTCTAATGGCTTCTCCTTTTCAGCATCAGCGT-TATACTTCTTCTTGAA; SEQ ID NO: 52) anti-sense F151A, F153A oligonucleotide (TTCAAGAAGAAG-TATAACGCTGATG CTGAAAAGGAGAAGCCATTA-GAAGG; SEQ ID NO:53) were used for QuikChange site-directed mutagenesis with BnKrp1#555 as the template. The mutagenesis product was sequenced to verify presence of desired mutations and then subcloned into the BamHI/XhoI site of pET16b-5MYC.

To construct BnKrp1#598 with multiple amino acids substitution in the CDK binding region (Y149A;F151A; F153A) the sense BnKrp1Y149A oligonucleotide (AATTTCAAGAAGAAGGCTAACGCTGATGCTGAA; SEQ ID NO:54) and anti-sense BnKrp1Y149A oligonucleotide (TTCAGCATCAGCGTTAGCCTTCTTCTT-GAAATT; SEQ ID NO:55) were used for QuikChange site-directed mutagenesis with TopoBnKrp#512 as the template. The mutagenesis product was sequenced to verify presence of desired mutations and then subcloned into the BamHI/XhoI site of pET16b-5MYC.

To construct BnKrp1#547, the following two oligonucleotides were used to amplify the BnKrp1 cDNA lacking the most C-terminal two amino acids, ie., Ser and Glu that add a 5' BamHI/NdeI site and XhoI restriction site on the 3' end of BnKrp1 (5' BnKrp1 BamHI/NdeI: ACGGATC-CCATATGGTGAGAAAATGC (SEQ ID NO:26) and 3' BnKrp1SE>stop XhoI: CTCGAGTCAAGCAGCTAATT-TAACCCACTCGTA (SEQ ID NO:56). The PCR fragment was amplified from pTG #313 (TopoII BnKrp1) and subcloned into the BamHI and XhoI site of pET16b-5myc and sequenced. The resulting vector BnKrp #547 contained the BnKrp1 cDNA in frame with the 6xHis and myc tags.

To construct BnKrp1#614, the following two oligonucleotides were used to amplify the BnKrp1 cDNA lacking the entire CDK binding domain. 5' BnKrp1 BamHI/NdeI: ACG-GATCCCATATGGTGAGAAAATGC (SEQ ID NO: 26) and the 3' BnKrp1Δcdk: CTCGAGTCACTTCTTGAAAT-TATC (SEQ ID NO: 57) which contains a XhoI site. The PCR fragment was amplified from pTG #420 (TopoII BnKrp1) and subcloned into TopoII (Invitrogen) and sequenced. The BamHI/XhoI fragment was then subcloned into pET16b-5myc. The resulting vector BnKrp #614 contained the BnKrp1 cDNA lacking the coding sequence for the CDK binding region in frame with the 6xHis and myc tags.

Example 2

Amino Acid Homology Between Mammalian p27$^{KIP1}$ and Plant KRPs

The CIP1/KIP1 family of CKIs utilizes two contact regions to bind and inhibit the kinase complex. Based on this mode of binding and inhibition, altering the binding capabilities of one of these two regions could potentially result in a dominant negative protein that can still interact with the complex (via the intact domain), no longer inhibit the kinase activity and interfere with the wild-type CKI from inhibiting an active cyclin/CDK complex. For example, if the cyclin binding region were rendered non-functional, the mutant protein would still interact through the CDK binding region with the kinase complex via the intact domain. Similarly, if the CDK binding region were rendered non-functional, the mutant protein would still interact through the cyclin binding region with the kinase complex.

The AtKrp family of CKI's share homology throughout the entire protein with the highest homology lying in the most C-terminal 40 to 45 amino acids (see Wang et al., Nature 386:451-452, 1997; Wang et al., Plant J. 15:501-510, 1998; Lui et al., Plant J. 21:379-385, 2000; De Veylder et al., Plant Cell 13:1653-1667, 2001; Jasinski et al., Plant Physiol. 130:1871-1882, 2002; Zhou et al., Plant Cell Rep. 20:967-975, 2002; Zhou et al., Plant J. 35:476-489, 2003). However, only the last approximately 23 amino acids of the Krp family show homology to the mammalian p27$^{Kip1}$ (see FIG. 1A and FIG. 1B).

In vitro binding experiments were performed to help elucidate the binding interactions between a representative KRP, namely BnKRP1, and the AtcyclinD2;1 and the AtCDKA. The binding interactions of other KRP family members can also be elucidated using the same in vitro binding experiments described below. In vitro binding experiments using mutant versions of BnKrp1 containing amino acid substitutions of highly conserved amino acids in the CDK binding region revealed that this region alone was necessary for the binding to the CDK, while binding to the Atcyclin was still intact. More importantly an intact CDK binding domain is absolutely required for inhibition of the AtCyclinD2/CDKA complex. Amino acids lying immediately upstream of the CDK binding region, in a region that the present inventors propose is the cyclin binding region, are conserved among KRP family members (see FIG. 1A and FIG. 1B) but not in p27$^{KIP1}$. Mutation of several conserved residues within this proposed cyclin binding domain abrogates the interaction with AtcyclinD2;1, while the interaction with AtCDKA remains intact. Interestingly, this putative cyclin binding region mutant still inhibits the AtcyclinD2/CDKA kinase complex yet not as effectively as the wild-type KRP1. The inhibitory concentration that reduces the kinase activity by 50% (IC$_{50}$) was 0.035 μg for the wild-type KRP1 (BnKrp#461) while the IC$_{50}$ for the cyclin binding mutant (BnKrp#462) was 1.25 μg.

Similar observations were seen with the mammalian p27$^{KIP1}$ counterpart (see Vlach et al., EMBO J. 16:5334-44, 1997). The IC$_{50}$ of the p27$^{KIP1}$ cyclin binding mutant was increased in comparison to the wild-type p27$^{KIP1}$. In contrast however, high concentrations of the p27$^{KIP1}$ CDK binding mutant were still capable of inhibiting the kinase complex. This is likely explained by the presence of the 310 helix in mammalian p27$^{KIP1}$ that is absent in the plant Krps (see example 3 for an explanation).

These data imply that two regions in KRPs exist which are similar to the mammalian p27$^{KIP1}$ counterpart responsible for the interaction with the active kinase complex. Interestingly, the cyclin domain mutant could still inhibit the kinase complex, suggesting that the CDK binding region was primarily responsible for cyclin/CDK kinase inhibition. Similarly the cyclin binding region of p27$^{KIP1}$ played an additive role in the inhibition of active CDK complexes. Yet these results illustrate that in contrast to p27$^{KIP1}$, the CDK binding region of KRP1 plays a more significant role in kinase inhibition.

Therefore focusing on the high homology between the KRP family and p27$^{KIP1}$ in the CDK binding region residues will be altered to ultimately create a dominant negative BnKrp1 molecule that can still bind the complex, interfere with wild-type BnKRP1 from inhibiting the kinase complex, yet not inhibit the complex itself.

Example 3

Protein Structure of Mammalian p27$^{KIP1}$ in Complex with Cyclin/CDK Used to Identify Keys Amino Acids that Contact CDK that are Conserved in Plant KRPs To facilitate the design of the dominant negative Krp molecules that would ultimately interfere with the wild-type KRP function the previously published structure of mammalian p27$^{KIP1}$ in complex with cyclin A-CDK2 kinase complex was used (see Russo et al., Nature 382:325-331, 1996). The structural information along with the alignment information were combined to identify key amino acids that when changed to alanine or other amino acid residues resulted in a protein with dominant negative characteristics. These dominant characteristics are as follows: 1) mutant Krp bind to cyclin/CDK complexes, 2) mutant protein do not substantially inhibit the formation of cyclin/CDK complex even at high concentrations and 3) mutant protein should compete substantially with the wild-type KRP molecule for binding to cyclin/CDK complexes. In vivo, mutant Krps that fulfill these characteristics would result in elevated cyclin/CDK kinase activity in the cell that would ultimately lead to increased cell proliferation and a higher mitotic index.

Mammalian cyclin A/CDK2 kinase activity can be completely shut down by the binding of p27$^{KIP1}$. The mechanism by which p27$^{KIP1}$ inhibits the cyclin A/CDK2 kinase complex has been shown to be a complex process (see Russo et al., supra). p27$^{KIP1}$ utilizes two means to inhibit the active kinase complex. The first component to the inhibition involves the p27$^{KIP1}$ 310 helix that is apparently not conserved in any of the plant KRP family of CKIs. The 310 helix inserts itself into the catalytic cleft of the kinase to mimic the ATP substrate. Occupation of this cleft region by the 310 helix effectively blocks ATP binding and kinase activity. However even in the absence of the 310 helix p27$^{KIP1}$ was still capable of inhibiting the kinase complex (see Polyak et al., Cell 78:59-66, 1994).

Comparison of the crystal structure of p27$^{KIP1}$ bound to cyclin A/CDK2 and the kinase complex alone illustrated that the N-terminal lobe of CDK2 undergoes significant conformational changes upon binding p27$^{KIP1}$ (see Russo et al., supra). In fact, specific β-sheets within the N-terminal lobe of the kinase that normally help coordinate the ATP in the active site are lost upon p27$^{KIP1}$ binding. Binding of p27$^{KIP1}$ induces a refolding that involves β-hairpin, β-strand residues and a 310 helix of p27$^{KIP1}$ and β-sheet amino acids of the N-terminal lobe of CDK2 that refold to form a intermolecular β-sandwich (see id.). This conformation change alone is capable of significantly inhibiting the kinase activity of cyclin A/CDK2. The residues within p27$^{KIP1}$ that form this β-sandwich are highly conserved in all mammalian p27$^{KIP1}$ family members and also well-conserved in all KRP family members. Based on the results set forth in Example 1, and the lack of a conserved 310 helix, the conserved CDK binding region in the KRP family members likely binds the active kinase complex and inhibits the kinase activity by inducing conformational changes in the N-terminal lobe of the AtCDKA kinase. However, another region of KRP can not be ruled out as actually mimicking ATP binding by inserting into the catalytic cleft just as the 310 helix does in mammalian p27$^{KIP1}$.

The most carboxy-terminal 23 amino acids of the KRP family show the greatest amino acid identity to the mammalian p27$^{Kip1}$ (see FIG. 1A and FIG. 1B). Several conserved residues in BnKRP1 were systemically changed based on sequence identity to mammalian p27$^{KIP1}$, play a role in forming the β-sandwich between the CKI and the kinase complex. Each mutant was compared to the wild-type BnKRP1 (BnKrp#461) for its ability to inhibit the kinase complex. In some cases the mutant BnKrp1 was also monitored for binding to AtcyclinD2;1 or the AtCDKA. Results for these experiments are summarized below in Table 2.

Mutations were introduced as described in detail in Example 4, "Mutant KRP CKI Polypeptides."

At the most N-terminal end of the CDK binding region resides the Lys Tyr Asn Phe Asp Phe (KYNFDF) motif (SEQ ID NO:58). This motif is highly conserved in KRP family members from both Arabidopsis and Brassica napus species. These residues are for the most part conserved in p27$^{KIP1}$. In p27$^{KIP1}$ they form a portion of a β-hairpin turn that ultimately forms the β-sandwich with CDK2 in the cyclin A-CDK2 complex. Each of these conserved residues were changed to alanine and tested for their ability to inhibit the kinase complex (see Table 2). Many single amino acid substitution mutations did not affect the ability to inhibit the kinase complex in vitro. However, BnKrp1 #587 and BnKrp1 #572, showed interesting results. In each case, kinase inhibition was attenuated compared to the wild-type protein suggesting that this region of KRP1 plays a role in kinase inhibition.

The side chains of both phenylalanines 62 and 64 in p27$^{KIP1}$ contact CDK2, play an integral role in forming the β-sandwich and are conserved in KRP1. (See FIG. 1A and FIG. 1B.) Since Krp1 F151A (BnKrp1 #572) inhibitory activity was partially compromised, both phenylalanines 151 and 153 were changed to alanine. This double mutant, BnKrp1 #512 no longer inhibited the kinase complex despite its ability to still bind the kinase complex via cyclinD2;1. There may still be some residual binding of this mutant to the CDK portion of the complex.

Tyrosine 149 of KRP1 is not conserved in p27$^{KIP1}$; however, it lies in the N-terminal position of the β-hairpin that contacts CDK2 and forms part of the β-sandwich. Tyrosine 149 is highly conserved in KRPs family members of Arabidopsis and Brassica. When Tyrosine 149 was changed to alanine (BnKrp1 #587), the inhibitory activity was partially compromised, suggesting that it plays an important role in the binding and/or inhibition of CDKA. Therefore, mutation of this position (Y149A) can be combined with the double mutant Krp1 F151A;F153A. This triple mutant was expected to retain its binding to the kinase complex while losing its ability to inhibit kinase activity.

The region C-terminal to the KYNFDF motif (SEQ ID NO:58) in KRP1 also contains several amino acids that are conserved in p27$^{KIP1}$. (See FIG. 1A and FIG. 1B.) Many of these residues are conserved in the β-strand of p27$^{KIP1}$ that forms a portion of the β-sandwich. Several of these conserved amino acids were changed in pairs to alanine (see Table 2 for summary). In all but one case, the inhibitory function was not significantly impaired. The exception was the Krp1 #545 (E164A;W165A) mutant that was a much weaker inhibitor than the wild-type KRP1. The tryptophan 165 extends its side chain within the β-sandwich. Phenylalanines 151, 153 and E164 and W165 were all changed to alanine (Krp1 #574). This compound mutant BnKrp1 also failed to inhibit the kinase complex even when used at high concentrations.

Truncation of the complete CDK binding region of KRP1 was also incapable of inhibiting the kinase complex. This was not surprising since the entire region responsible for binding the CDK was deleted. However we believe it likely that such a truncation will result in an unstable protein.

Example 4

Mutant KRP CKI Polypeptides

As an improvement over previous techniques used to silence gene expression at the post-transcriptional RNA level, suppression of KRP family members in plants has been accomplished at the protein level using a dominant-negative strategy. The basic principle of the dominant negative strategy is to engineer a gene to produce a mutant protein that prevents the normal copies of the same protein from performing their function. In this case, the normal KRP protein forms a multi-subunit complex with cyclin/CDK complex to inactive the kinase activity. Therefore, expressing a mutant version of wild-type KRP1 will interfere with the normal copies of KRP1 from inhibiting cyclin/CDK kinase activity. Furthermore, given the high degree of homology between the 7 KRP family members of Brassica, the mutant Krp1 will behave as a dominant negative towards other family members or possibly all family members. Finally, the cyclin and CDK binding regions of KRPs are well-conserved in other plant species. Therefore, this dominant negative Krp1 will protect cyclin/CDK kinase complexes from inhibition by endogenous KRPs in other plants such as, e.g., corn, wheat, Canola, soy, rice, cotton, poplar and the like.

Previously, dominant negative mutants have been used to help elucidate various signal transduction pathways. In particular, dominant negative Ras, a GTPase is the most commonly used dominant negative protein to date and has played a major role in the strategy used to study other GTPases (Feig and Cooper, Mol. Cell. Biol. 8:3235-3243, 1988). Similarly, dominant negative versions of CDKs were used to identify roles for CDKs in cell cycle control (van den Heuvel and Harlow, Science 262:2050-2054, 1993).

The KIP/CIP family of CKIs differs from the INK family of inhibitors in the mechanism they use to inhibit the kinase complex. While the INK family only binds to the CDK, the CIP/KIP family has two conserved regions that independently bind the cyclin and CDK. The fact that the CIP1/KIP1 family of CKIs and the KRP family of CKIs utilize two contact regions to bind the complex makes them an ideal candidate for the dominant negative strategy. This is so because the CDK binding region can be targeted for mutants that abolish the interaction with the CDK while keeping the region of KRP1 that binds the cyclin intact.

In the present invention, the Canola, *Brassica napus* (Bn), KRPs and mouse ear cress *Arabidopsis thaliana* (At) KRP molecules have been cloned and their ability to inhibit cyclin/CDK activity confirmed. To this end, an in vitro assay was developed to test various KRP's ability to inhibit cyclin/CDK complexes. *Arabidopsis* cyclin D2;1 (AtcyclinD2;1) and *Arabidopsis* CDKA (AtCDKA) were epitope tagged and cloned into a baculovirus expression vector system (BD Biosciences). AtCyclinD2;1 was tagged with the FLAG epitope (Sigma-Aldrich) on the N-terminus. The hemagglutinin (HA) epitope was placed in frame with the 5' end of AtCDKA. Production of AtcyclinD2;1 protein was achieved by infecting *S. frugiperda* Sf9 cells with AtcyclinD2;1 baculovirus. Production of AtCDKA was achieved by infection of *S. frugiperda* Sf9 cells with CDKA baculovirus. An active complex of cyclin D2;1/CDKA was accomplished by co-infecting of *S. frugiperda* Sf9 with AtcyclinD2;1 plus AtCDKA baculovirus. The cyclin, CDK and the active complex were purified and assayed for kinase activity. Kinase activity was monitored using a standard kinase assay with Histone HI (HHI) as the substrate or by using recombinant NtRb (Nakagami et al., *Plant Cell* 14:1847-1857, 2002). AtCyclin D2;1 infected insect cells produced no active complex. Similarly AtCDKA infected cells produced no active kinase. When cells were infected with both the Atcyclin D2;1 and AtCDKA, kinase activity was easily detected. Active cyclin CDK complexes can also be purified from plant protein tissue extracts or from plant tissue culture cell extracts by using p13suc1 agarose beads (Wang et. al., *Plant J.* 15:501-510, 1998).

Krps were designed to contain a N-terminal poly-histidine epitope tag (HIS tag) by subcloning the Krp cDNA inframe with the coding sequence for HIS tag in the pET16b vector (Novagen). Wild-type and mutant Krp protein expression was induced in bacteria and subsequently purified as a HIS tag fusion protein using Ni-agarose.

All wild-type *Brassica napus* (Bn)Krps tested (BnKRP1, BnKRP4, BnKRP5) were extremely effective at inhibiting the Atcyclin D2;1/CDKA complex. In all cases inhibition was also dose responsive. Several other *Arabidopsis* AtKrps (AtKRP1, AtKRP2) were also effective inhibitors.

CIP1/KIP1 family of CKIs utilize two contact regions to bind and inhibit the kinase complex. Based on this mode of binding and inhibition, altering the binding capabilities of one of these two regions could potentially result in a mutant protein with dominant negative characteristics. For example, if the cyclin binding region is rendered non-functional, the mutant protein would still interact through the CDK binding region with the kinase complex via the intact domain. Similarly, if the CDK binding region is rendered non-functional, the mutant protein would still interact through the cyclin binding region with the kinase complex.

ICK/KRP family members have limited amino acid identity to the mammalian $p27^{KIP1}$ family. This identity is limited to the most C-terminal 24 to 30 amino acids. In fact the location of the cyclin/CDK binding domain of mammalian $p27^{KIP1}$ is located at the N-terminus of the protein while the homologous region in the plant Krps is found at the most C-terminal portion of the protein. (See FIG. 1A and FIG. 1B, showing alignment of $p27^{KIP1}$ and various Krp family members.) The cyclin binding region within mammalian $p27^{KIP1}$ is not conserved in plant KRPs. Yet the region immediately upstream of the putative CDK binding region is conserved in all plant KRPs. This conserved region although not homologous to $p27^{KIP1}$ could be responsible for the interaction with the cyclin. Amino acid substitutions of several residues in this proposed cyclin binding region of BnKRP1 (amino acids 125-138) abolishes binding to the cyclin but does not affect binding to the CDK. These data suggest that two regions exist in KRPs similar to the mammalian $p27^{KIP1}$ counterpart that mediate the interaction with the active kinase complex. Interestingly, mutating the cyclin binding region did not completely abolish inhibition of the kinase complex, suggesting that the CDK binding region is primarily responsible for cyclin/CDK kinase inhibition.

Given the high degree of homology between the CDK binding regions of plant and mammalian CKIs, the crystal structure of $p27^{KIP1}$ bound to the cyclin A/CDK2 complex was used to help identify contact residues of $p27^{KIP1}$ that bind the cyclin and CDK (Russo et al., *Nature* 382:325-331, 1996). Contact residues were compared to various KRP sequences to determine whether or not they are conserved in the region that carries the highest homology to $p27^{KIP1}$. At the most N-terminal end of the CDK binding region lies the LysTyrAsnPheAspPhe (KYNFDF) (SEQ ID NO:58) motif. These residues are for the most part conserved in p27. They form a β-sheet that contacts CDK2 in the cyclin A-CDK2 complex.

Each of these conserved residues were changed to alanine and tested for their ability to inhibit the kinase complex. Interestingly, many of these single amino acid substitution mutations did not affect the ability to inhibit the kinase complex in vitro. However Krp1 F151A and Krp1 Y149A mutants did reduce the CKI activity without affecting binding to the kinase complex.

Since the side chains of both phenylalanines 151 and 153 contact the CDK and Krp1 F151A inhibitory activity was partially compromised, both phenylalanines 151 and 153 were replaced by alanine. This double mutant BnKrp 1 (BnKrp1 F151A;F153A) no longer inhibits the kinase complex despite its ability to bind the kinase complex via cyclinD2;1. It cannot be ruled out that there may still be some residual binding of this mutant to the CDK portion of the complex.

Tyrosine 149 in Krp1 is not conserved in $p27^{KIP1}$, however in the structural model of mammalian p27 a similar amino acid residue lies in the position of the β-sheet that contacts CDK2. When changed to alanine (Krp1Y149A) the inhibitory activity was partially compromised, suggesting that this amino acid residue plays an important role in the binding and/or inhibition of CDKA. Therefore, mutation of this position (Y149A) combined with the double mutant Krp1 F151A;F153A produced a variant protein that no longer inhibited the kinase complext. It is expected that this triple mutant (BnKrp1 Y149A;F151A;F153A) still retains binding to the kinase complex while unable to inhibit kinase activity.

As above, the single amino acid substitutions of Y149A and F151A both individually reduced the ability of the mutant BnKrp1 polypeptide from inhibiting the kinase complex. The double mutant of BnKrp1 Y149A;F151A is expected to produce a mutant protein that no longer inhibits the kinase complex.

The region C-terminal to the KYNFDF motif (SEQ ID NO:58) in KRP1 also contains several amino acids that are conserved in p27$^{KIP1}$. These conserved amino acids were changed, in pairs to alanine. In all but one case, the inhibitory function was not significantly impaired. The exception was Krp1 E164A;W165A mutant that was a much weaker inhibitor than the wild-type KRP1. In a separate derivative protein, Phenylalanines 151, 153 and E164 and W165 were all replaced by alanine. This multiple mutant of BnKrp1 also failed to inhibit the kinase complex.

Truncation of the complete CDK binding region of KRP1 was also incapable of inhibiting the kinase complex. This was not surprising since the entire region responsible for binding the CDK was deleted.

Results of the evaluation of various BnKrp1 mutants for biological activity are summarized in Table 2.

TABLE 2

Biological Activity of BnKrp1 Mutants

| Construct Number | Krp Mutation | Cyclin binding | CDK binding | Inhibition of Kinase Activity | Dominant Negative?[1] |
|---|---|---|---|---|---|
| 461 | BnKRP1 wild type | +++ | +++ | +++ | N/A[2] |
| 586 | BnKrp1 K148A | ND[3] | ND | +++ | N/A |
| 587 | BnKrp1 Y149A | ND | ND | ++ | − |
| 588 | BnKrp1 N150A | ND | ND | +++ | N/A |
| 572 | BnKrp1 F151A | +++ | +/− | ++ | − |
| tbd | BnKrp1 D152A | ND | ND | ND | N/A |
| 573 | BnKrp1 F153A | ND | ND | +++ | N/A |
| 512 | BnKrp1 F151A; F153A | +++ | − | −[4] | ++++ |
| 598 | BnKrp1 Y149A; F151A; F153A | ND | ND | −[4] | +++++ |
| 553 | BnKrp1 K157A; P158A | ND | ND | +++ | N/A |
| 554 | BnKrp1 R162A; Y163A | ND | ND | ++ | − |
| 555 | BnKrp1 E164A; W165A | ND | ND | −[4] | ++ |
| 574 | BnKrp1 F151A; F153A; E164A; W165A | ++ | − | −[4] | ++ |
| 556 | BnKrp1 KL-AA | ND | ND | ND | ND |
| 547 | BnKrp1 SE-stop | ND | ND | +++ | N/A |

[1]Protection of kinase complex from inhibition by wild-type BnKrp1.
[2]N/A means not applicable.
[3]ND means not determined.
[4]candidate did not inhibit the kinase activity even when used up to 10 times the minimum amount of wild-type inhibitor needed to abolish kinase activity.

As mentioned previously, disrupting the cyclin binding domain resulted in a mutant Krp1 protein that still retained some inhibitory activity. Nevertheless, there likely exists other amino acids within the putative cyclin binding region (amino acids 125-138) that can be altered to create a mutant protein that fulfills the optional dominant negative characteristics. In addition, while alanine was used in all substitutions in these particular studies, it is expected that replacing the identified amino acid residues with another non-alanine amino acid residue that differs significantly in one or more physical properties (other non-conservative substitutions) will also yield a dominant negative protein. In particular, it is expected that replacing a particular amino acid residue with an oppositely charged amino acid or with an amino acid residue with a substantially different defining characteristic, such as a hydrophilic residue with a hydrophobid residue and vice versa, and the like, will yield an even better dominant negative candidate.

The ideal dominant negative candidate will not inhibit the kinase activity even when used up to 10 times the minimum amount of wild-type inhibitor needed to abolish kinase activity. Several mutants fulfilled this requirement (see Table 2). The importance of this feature lies in the fact that when expressed in vivo, the levels of the mutant protein may be in excess levels compared to the wild-type protein.

The dominant negative BnKrp1 molecules identified in this study effectively protect the AtcyclinD2;1/CDKA complex from wild-type BnKRP1 inhibition. The same dominant negative derivative Krp1 molecule also protects the kinase complex from inhibition by KRP molecules from other species such as Maize, Soy, rice, cotton, poplar and alfalfa (see Example 7).

Example 5

Mutant BnKrp1 Proteins Competitively Block the Wild-Type CKI Protein from Inhibiting the Kinase Complex Dominant negative candidates that are particularly useful will not inhibit the kinase activity even when used up to 10 times the minimum amount of wild-type inhibitor needed to abolish kinase activity. Several mutants fulfilled this requirement (see Table 2, FIG. 1A and FIG. 1B, and Example 2). The importance of this feature lies in the fact that when expressed in vivo, the levels of the mutant protein may be in excess levels compared to the wild-type protein, and it is important that the mutant protein does not substantially inhibit the kinase complex at virtually any concentration.

Several dominant negative candidates were tested for their ability to protect the AtcyclinD2;1/CDKA complex from wild-type BnKRP1. The competition experiments were performed as follows. Active cyclinD2;1/CDKA kinase complex (7 µg) was pre-incubated with candidate dominant negative BnKrp1 mutants (5 µg or 10 µg) for 20 minutes in 1× kinase buffer. The complex was then tested for its kinase activity in the absence or after the addition of wild-type BnKrp1 (0.5 µg, 1.0 µg or 2 µg) using HHI as the substrate. The kinase reactions were then resolved by SDS PAGE as described in Example 1, "Kinase assay." Results were quantified by phosphorImager (Molecular Dynamics).

BnKrp1 F151A;F153A (BnKrp1 #512) was capable of protecting the kinase complex from inhibition by the wild-type BnKRP1. 5 µg of BnKrp1 F151A;F153A restored up to 40% of the kinase activity in the presence of 0.6 µg wild-type KRP1. This dominant negative effect was dose dependent, up to 60% of the kinase activity was restored when 10 µg of BnKrp1 F151A;F153A was used.

The mutant BnKrp1 #555 (E164A;W165A) is a promising dominant negative candidate because it also failed to inhibit the kinase activity even when used at 10 µg per reaction. In competitive experiments, this mutant protected the active kinase complex from inhibition by wild-type KRP1 but only restored activity by 14% when 5 µg was used and by 15% when 10 µg was used. The mutations from BnKrp1 #512 and BnKrp1 #555 were combined into one mutant protein called BnKrp1 #574 (F151A, F153A, E164A, W165A). This compound mutant failed to inhibit the kinase activity on its own at 5 µg and 10 µg quantities. This compound mutant was capable of protecting the kinase complex from inhibition by wild-type BnKRP1 but could only restore activity by as much as 35%. The mutant BnKrp1 #598(Y149A;F151A;F153A) was capable of protecting the kinase complex from inhibition by the wild-type BnKRP1. 5 µg of BnKrp1 F151A;F153A restored up to 55% of the kinase activity in the presence of 0.6 µg wild-type KRP1. This dominant negative effect was dose dependent, up to 80% of the kinase activity was restored when 10 μg of BnKrp1 Y149A;F151A;F153A was used.

These data suggest that the optimal region to target for a dominant negative is the β-hairpin region. However not just any residue can be altered. Several single amino acid substitutions failed to create a dominant negative Krp (see Example 3) but in fact, changing too many of the conserved residues also resulted in a mutant that fulfills most of the requirements of the dominant negative except it ultimately failed to behave as a dominant negative. AtKrp2 is the most closely related to BnKrp1 and AtKrp1. The mutant AtKrp2 where the KYNFDF motif (SEQ ID NO:58) was changed to KAAAAA (SEQ ID NO:59) had promising characteristics of a dominant negative Krp molecule. At high concentrations, this BnKrp2 mutant failed to inhibit the kinase complex as expected. Interestingly, this mutant failed to protect the kinase from inhibition by wild-type BnKRP1.

In summary: BnKrp1 F151A;F153A blocked the wild-type KRP from inhibiting the kinase, BnKrp1 E164A; W165A was not as good at blocking the wild-type KRP while BnKrp1 (Y149A;F151A;F153A) was the best dominant negative candidate in the vitro competition assways. The double mutant BnKrp1(Y149A;F151A) is also likely to be capable of protecting the kinase complex from inhibition.

As mentioned earlier, disrupting the cyclin binding domain resulted in a mutant Krp1 protein that retained some inhibitory activity. Nevertheless there likely exists other amino acids that can be altered to create a mutant protein that fulfills all of the dominant negative characteristics. Furthermore, alanine was the amino acid of choice for all substitutions. In many of the mutants presented, replacing the residue with an non-conservative amino acid could yield an even better dominant negative candidate.

Example 6

BnKrp1 F151A;F153A and BnKrp1 Y149A;F151A;F153A Behave as a Dominant Negative Towards Other *Brassica napus* KRP Family Members One of the overall objectives of the dominant negative strategy was to introduce a mutation into a single member of the KRP family that behaves as a dominant negative not only towards its wild-type counter part but also towards all of its family members. The alignment of the KRP family of CKIs in *Brassica napus* and in *Arabidopsis* illustrates the high sequence identity that lies in the extreme C-terminus of the protein. Data has been presented above demonstrating that the conserved region just N-terminal to the CDK binding domain is responsible for binding cyclins. Furthermore, several groups have presented 2-hybrid screening data illustrating that several KRP molecules have overlapping specificity for cyclin binding.

BnKRP4 differs from BnKRP1 in the β-hairpin. Phe 151 is conserved between BnKRP1 and BnKRP4, however, BnKRP1, F153 is a proline in BnKRP4. This is not necessarily a conservative amino acid substitution and suggests that BnKRP4 may interact with the cyclin/CDKA complex differently than BnKRP1. However it has already been shown that this position within the CDK binding domain does not appear play a significant role in cyclin/CDKA inhibition(mutant BnKrp1 #573, see Example 1).

BnKRP4 was cloned using the following two oligonucleotides to amplify the BnKrp4 cDNA adding a 5' BamHI/NdeI site and XhoI restriction site on the 3' end of BnKrp4-1 (5' BnKrp4-1 BamHI/NdeI: GGATCCCATATGGGA AAATACATAAAG (SEQ ID NO:60) and 3' BnKrp4-1 XhoI: CTCGAGCTAATCATCTACCTTCTT (SEQ ID NO:61). The PCR fragment was amplified from pTG #315 (TopoII BnKrp4-1) and subcloned into the BamHI and XhoI site of pET16b-5myc and sequenced. The resulting vector BnKrp #605 contained the BnKRP4 wild-type cDNA in frame with the 6×His and myc tags. The protein was expressed and purified as described in example 1.

BnKrp4 is a potent inhibitor of the AtcyclinD2;1/AtCDKA kinase complex with an $IC_{50}$ very similar to that of wild-type BnKRP1. Competition experiments were performed as described in Example 4. In this case, BnKrp1 #512 (F151A;F153A) and BnKrp1 #598 (Y149A;F151A;F153A) were both capable of protecting the kinase complex from inhibition by wild-type BnKRP4. Based on this observation, it is expected that BnKrp1 #512 and BnKrp1 #598 would behave as a dominant negative towards most, if not all, BnKRP family members.

Example 7

BnKrp1 F151A;F153A and BnKrp1 Y149A;F151A;F153A Behave as Dominant Negative Towards Krps of Other Plant Species The overall objective of the dominant negative strategy was to introduce one or more mutations into a single member of the KRP family that not only behaves as a dominant negative towards its wild-type family members but also against KRP family members across different plant species. Crop plants of interest in the present invention include, but are not limited to, soybean, canola, corn, wheat, alfalfa, rice, vegetable crops such as tomato, and even trees, such as poplar.

The nucleotide sequence of AtKRP1 (GenBank# U94772) was used to perform a tBLASTn search for KRP sequences of maize, soy, poplar, tobacco and rice. Several short ESTs showed high homology limited to the cyclin/CDK binding domains. Several of these short sequences were aligned and illustrate the conservation of this region across various plant species. (See FIG. 2)

In maize, one particular entry, Genbank accession # AY986792 contained an open reading frame of 573 bp, encoding a full length protein with high identity to several Bn KRP family members. This protein was called ZmKRP4 but it isn't necessarily the maize homologue of BnKRP4 or AtKRP4. Like BnKRP4, ZmKRP4 differs from BnKRP1 in the β-hairpin. Phe 151 was conserved between BnKRP1 and BnKRP4 and ZmKRP4. However, BnKRP1 F153 was a proline in both BnKRP4 and ZmKRP4. ZmKRP4 was amplified from cDNA made from total RNA isolated from mature corn tassels. The sequence of the oligonucleotide was gathered from the Genbank accession # AY986792. ZmKRP4 5' BamHI/NdeI: GGATCCCATATGGGCAAG-TACATGCGC (SEQ ID NO:62) and ZmKRP4 3'BamHI: GGATCCTCAGTCTAGCTTCACCCA (SEQ ID NO:63). The PCR product was subcloned into TOPOII (Invitrogen) and sequenced. For protein product of ZmKRP4, the 573 bp BamHI fragment was cloned into the BamHI site of pET16b-5Myc vector and insert orientation was determined by restriction enzyme mapping. Recombinant protein was produced as described in Example 4.

Similarly in soy, one particular entry, Genbank accession # AY439104 contained an open reading frame of 499 bp, encoding a full length protein with high identity to several Bn KRP family members. This protein called GmKRP2-2 is virtually identical to BnKRP1 within the β-hairpin. GmKRP2-2 was amplified from cDNA made from total RNA isolated from young developing soy plantlets. Oligonucleotide were designed from the sequence of Genbank accession # AY439104: GmKRP2-2 5'XhoI/NdeI: ctcgaggacatatggagatggctcaggttaaggca (SEQ ID NO:64) and GmKRP2-1 3' XhoI: ctcgagtcaactgaacccactcgtatcgtcc (SEQ ID NO:65). The PCR product was subcloned into TOPOII (Invitrogen) and sequenced. For GmKRP2-2 protein expression, the 499 bp XhoI fragment was cloned into the XhoI site of pET16b-5Myc vector and insert orientation was determined by restriction enzyme mapping. Recombinant protein was produced as described in Example 4.

Both ZmKRP4 and Gm Krp2-2 were tested for their ability to inhibit recombinant AtcyclinD2;1/CDKA kinase complex. ZmKRP4 was a potent inhibitor of the kinase complex with an $IC_{50}$ very similar to that of wild-type BnKRP1, 0.035 µg. Similarly, GmKrp2-2 was also a potent inhibitor of the kinase complex. Both dominant negative BnKrp1 (BnKrp1 #512 and #598) were capable of blocking ZmKRP4 and GmKrp2-2 from inhibiting the kinase complex. In each case, the protection was comparable to the protection that BnKrp1 #512 gave towards BnKRP1 inhibition. This result illustrates the cross species effect of the dominant negative Krp of the present invention.

The experiments also suggest that BnKrp #512 and BnKrp #598 will have a similar effect on other cross-species KRP family members such as those from rice, wheat, sorgum, sugar cane, sugar beets, and the like. KRP molecules from these plant species, along with others, can be cloned, expressed as recombinant proteins, and evaluated in similar studies to demonstrate that BnKrp1 #512 and BnKrp1 #598 has a similar effect on these family members.

Example 8

Parallel Mutation in Other Plant Species KRP Molecules Results in Dominant Negative Molecules The residues changed in BnKRP1 to produce the dominant negative effect are conserved in several family members of KRPs in Canola, corn, soy, rice, alfalfa, poplar, tobacco, and the like. The substitution of conserved phenylalanines to alanine residues can be performed in several KRPs of these crop plants and tested for their ability to behave as dominant negative molecules.

F151 and F153 are conserved in some but not all KRPs in Canola, soy, corn. Mutation of these conserved residues in soy and corn KRPs will result in a similar dominant negative Krp molecule.

Example 9

Transgenic Canola Plants Expressing Transgene Constructs Designed to Confer Embryo-Specific and Constitutive Expression of Krp1 (F151A;F153A)

Based on the in vitro results present in the above examples, expression of the invention in cultured plant cells or in transgenic plants is predicted to increase endogenous CDK kinase activity. This increase in CDK kinase activity will have a positive driving incluence on the cell cycle. The invention was cloned into a plant expression vector. A plant expression vector contains a native or nonnative promoter linked to the above described invention. Promoters can range from strong, weak, inducible, tissue-specific, organ specific and developmental specific.

The equivalent of BnKrp1 (F151A;F153A) mutations were introduced into AtKRP1 using the following oligonucleotides: "QC AtKrp1 cds F173A;F175A-coding" 5'-TTCAAGAAGAAGTACAATGCCGATGCCGA-GAAGGAGAAGCCATTA-3' (SEQ ID NO:66) and "QC AtKrp1cds F173A;F175A-noncod" 5'-TTATGGCTTCTC-CTTCTGGGCA TCGGCATTGTACTTCTTCTTGAA-3' (SEQ ID NO:67). AtKrp1 #359 was used as the template using a Stratagene Quikchange Site Directed Mutagenesis Kit. AtKrp1 F173A; F175A (pTG356) was confirmed by sequencing. The LFAH12 promoter was inserted on the 5' end of the mutant AtKrp1 (F173A;F175A) in pTG 356 in two steps. First, the SalI and PstI LFAH12 promoter from pCAMBIA 2381Z (pTG 254) was subcloned into pBluescript II (Stratagene) in the SalI and PstI sites, resulting in pTG 357. The LFAH12 promoter was then cut from pTG 357 using PstI and BamHI and inserted into pTG 356 resulting in pTG 361. Finally pTG 361 was digested with KpnI and NotI, pLAY112 was digested with NotI and BglII (mas3' utr component) and pCGN 1547 was digested with KpnI and BamHI and a 3-way ligation was performed. This resulted in a LFAH12-At Krp1 cds DN-mas 3' utr cassette (pTG 369).

The plant expression vector containing BnKrp1(F151A;F153A) under control of the constitutive promoter 35S was constructed in the following way. The BamHI/XhoI fragment containing BnKrp1 (F151A;F153A) cds was cloned into pTG 271 (35S/TOPO Blunt) using the same sites. The resulting construct (pTG529) was cut with KpnI and XbaI. pLAY112 was cut with XbaI and HindIII and pCGN1547 was cut with KpnI and HindIII and a 3-way ligation was performed. This resulted in a 35S-BnKrp1 (F151A;F153A)-mas3 utr cassette (pTG533).

Canola (*Brassica napus*) Transformation

The double haploid canola variety DH12075 was transformed with the LFAH-12 AtKrp1 (F173A;F175A) and 35-S BnKrp1 (F151A;F153A) transgene expression constructs (also referred to collectively in this Example as "mutant Krp1 transgene expression constructs") using an *Agrobacterium*-mediated transformation method based on that of Maloney et al. (Maloney et al., *Plant Cell Reports* 8:238, 1989).

Sterilized seeds were germinated on ½ MS (Murashige & Skoog) media with 1% sucrose in 15×60 mm Petri dishes for 5 days with approximately 40 to about 60 seeds per plate. A total of approximately 1500 seeds were germinated for each transformation construct. Seeds were not fully submerged in the germination medium. Germinated seedlings were grown in a tissue culture room at 25° C., on a 16 hour light/8 hour dark cycle.

Cotyledons were cut just above the apical meristem without obtaining any of the meristem tissue. This was done by gently gripping the two petioles with forceps immediately above the apical meristem region. Care was taken not to crush the petioles with the forceps. Using the tips of the forceps as a guide, petioles were cut using a scalpel with a sharp No. 12 blade. Cotyledons were released onto a 15 mm×100 mm plate of co-cultivation medium. Properly cut cotyledons separate easily. If they did not, there was a very good chance that meristematic tissue had been obtained and such cotyledons were not used. Each plate held approximately 20 cotyledons. Cotyledon explants were inoculated with *Agrobacterium* after every few plates that were prepared to avoid wilting which would have a negative impact on following stages of the protocol.

Mutant Krp1 transgene expression constructs were introduced into *Agrobacterium tumefaciens* electroporation.

Agrobacterium harboring the mutant Krp1 transgene expression constructs were grown in AB medium with appropriate antibiotics for two days shaking at 28° C. To inoculate cotyledon explants, a small volume of Agrobacterium culture was added to a 10 mm×35 mm Petri dish. The petiole of each explant was dipped into the Agrobacterium culture and the cut end placed into co-cultivation medium in a Petri dish. The plates were sealed and placed in a tissue culture room at 25° C., 16 hour light/8 hour dark for 3 days.

After 3 days, explants were transferred in sets of ten to fresh 25 mm×100 mm Petri dishes containing shoot induction medium. This medium contained a selection agent (20 mg/L Kanamycin) and hormone (4.5 mg/L BA). Only healthy-looking explants were transferred. Explants were kept on shoot induction medium for 14 to 21 days. At this time, green calli and possibly some shoot development and some non-transformed shoots may could be observed. Non-transformed shoots were easily recognized by their white and purple color. Kanamycin-sensitive shoots were removed by cutting them away and all healthy-looking calli were transferred to fresh plates of shoot induction medium. The explants were kept on these plates for another 14 to 21 days.

After 2 to 3 weeks, shoots that were dark green in color were transferred to plates containing shoot elongation medium. This medium contained a selection agent (20 mg/L Kanamycin) but did not contain any hormones. Five shoots were, transferred to each plate. The plates were sealed and returned to the tissue culture room. Transformed shoots that appeared vitrious were transferred to shoot elongation medium containing phloroglucinol (150 mg/L). Shoots that became healthy and green were returned to shoot elongation medium plates. Repeated transfers of vitrious shoots to fresh plates of the same medium were required in some cases to obtain normal looking shoots.

Shoots with normal morphology were transferred to 4 oz. baby food jars with rooting medium containing 0.5 mg/L indole butyric acid. Any excess callus was cut away when transferring shoots to the jars. Shoots could be maintained in jars indefinitely by transferring them to fresh jars containing 0.2 mg/L indole butyric acid approximately every 6 weeks.

Once a good root system had formed, the $T_0$ generation shoots were removed from jars, agar removed from the roots, and the plantlet transferred to potting soil. Each independent $T_0$ plantlet represents an independent occurrence of insertion of the transgene into the canola genome and is referred to as an event. A transparent cup was placed over the plantlet for a few days, allowing the plant to acclimatize to the new environment. Once the plant had hardened, the cup was removed. The $T_0$ transgenic events were then grown to maturity in the greenhouse and $T_1$ seeds collected.

$T_0$ Event Characterization

The number of transgene insertion site loci was determined in each event by Southern analysis. Mutant Krp1 transgene expression in the $T_0$ events was verified by Northern analysis or end-point RT-PCR. Mutant Krp1 transgene expression data were obtained for a single time point in embryo development, 19 days after pollination (DAP). From these data it was concluded that, at this developmental time point, the LFAH12 promoter was driving high levels of AtKrp1 (F173A;F175A) mRNA. The 35S BnKrp1 (F151A; F153A) transgene expression was monitored in leaf samples which had moderate to high level expression in many events. The expression data demonstrated that both promoters were functional in driving mutant Krp1 transgene expression in transgenic canola plants.

Kinase activity can also be measured to determine effect of mutant Krp1 protein expression on endogenous Cyclin-CDK kinase activity. Equivalent amounts of protein extracts from transgenic and non-transgenic plant tissue or cells are enriched for CDK using p13Suc1 resin (Upstate, Chicago, Ill.) and Histone kinase assays are performed as described in example 4 or by Wang et al., Plant J. 15:501-510, 1998. Kinase reactions are resolved by SDS-PAGE and HHI phosphorylation quantified by PhosphorImager.

$T_0$ plants were successfully generated for both mutant Krp1 transgene expression constructs. The tested constructs included (a) LFAH12/AtKrp1(F173A;F175A); (b) 35S BnKrp1(F151A;F153A).

Example 10

Expression In Vivo Accelerates Growth/Early Germination

Expression of the mutant proteins of the present invention in transgenic plants will exert their effects by elevating cyclin-CDK kinase activity. This will have a positive driving influence on the cell cycle that ultimately results in increased organ size. In plants, reducing Krp1 expression levels by suppressing expression of an endogenous Krp gene in the embryo using an inverted repeat approach results in increased seed size and crop yield. In addition to an effect on yield, increased seed size can result in increased vigor of the seed. Larger seeds contain a greater amount of stored protein and starch reserves to be utilized during germination and seedling growth. This can result in earlier germination and more rapid early growth. Early germination and early rapid growth are agronomically valuable traits since they lead to more rapid establishment of the crop. This increases the chances of a successful crop by reducing the window of vulnerability to harsh environmental conditions and the like that can damage or ruin a crop before establishment.

Increased growth and developmental pace were observed in greenhouse-germinated seedlings of transgenic canola plants transformed with the AtKrp1 (F173A;F175A) dominant negative expression construct (pTG369) described in Example 9. Twenty-four seeds from each of fifteen independent transformation events of the AtKrp1 (F173A; F175A) dominant negative expression construct were planted in Jiffy peat pellets in trays and germinated in a greenhouse. Twenty four seeds from each of fifteen independent events transformed with the wild type KRP1 gene, also under control of the LFAH12 promoter, were planted in parallel. Additionally, the untransformed parental DH12075 canola variety and a total of 135 transgenic events transformed with any of nine unrelated transgene constructs were planted at the same time.

After three weeks growth, all seedlings were transplanted to a field to be grown to seed. Each set of twenty four seedlings for each event was planted as an individual plot. At transplantation, there were readily observed differences in growth among the seedlings between plots. Across the entire seedling population for all transgene constructs, size varied from 1 inch tall to about 4 to 5 inches tall. Developmental progress also varied, ranging from a few seedlings having only cotyledons present to seedlings with several true leaves. The untransformed parental variety plots fell in the middle of this range. Differences in the transgenic plots were construct specific. Most of the plots in the field that contained seedlings at the top end of the size and development range were plots containing plants transformed with the AtKrp1 (F173A;F175A) dominant negative expression construct (pTG369). Other constructs did not show this characteristic with most plots showing growth and development comparable to or less than the untransformed parental variety. These results indicate that expression of a dominant negative mutant Krp transgene confers an increased early growth rate and accelerated developmental pace.

Further characteristics to be monitored include, for example, pre-emergence/germination duration, time of emergence of cotyledon, size of cotyledon, time of first true leaf exposed, and second true leaf exposure. Rosette diameter can also be monitored in transgenic and non-transgenic plants. Other characteristics can also be monitored between the transgenic and non-transgenic plants and include, for example, time of bud emergence and size of the bud bolt, final size of main raceme, time of the first flower to emerge, timing of first pod appearance, and the like.

Example 11

Expression In Vivo Gives Better Rooting

Canola seeds are very small, require relatively high moisture for germination and must be planted close to the soil surface to maximize seedling vigor. Small seeds and shallow planting make the crop vulnerable to abiotic stresses such as dry soil, and flooding. Ubiquitous expression or expression early in root development of the mutant polypeptides of the present invention under control of various promoters would give accelerated root growth and development. Increased cell division during root development will benefit seedling vigor by establishing a firm root base sooner and possibly a larger root base than non-transgenic plant control. The size of the transgenic plants root system can be compared to non-transgenic plant.

Example 12

Evaluation of the Effect of AtKrp1 (F173A;F175A) Transgene Expression During Embryo Development on Canola Yield in Replicated Field Trials In this example the transgenic canola plants comprising the *Arabidopsis* Krp1(F173A;F175A) transgene under the control of the LFAH12 embryo specific promoter (pTG369) was tested in field trials.
Advancement of Transgenic AtKrp1 (F173A;F175A) Events to Field Trials.

$T_0$ events were selected for advancement to field trials based on a combination of transgene expression and transgene insertion locus number. Events with verified transgene expression and a single transgene insertion locus were assigned the highest priority to be carried forward to field testing. In some instances, events with multiple insertion loci were selected if the presence of multiple genes gave a high overall transgene expression level due to gene dosage.

$T_1$ seeds from selected events were grown as segregating $T_1$ populations in field plots. Each event was planted as a two row, twenty four plant plot. For events with a single transgene insertion locus, segregation of the transgene among the twenty four $T_1$ plants would produce a distribution of approximately six null plants lacking the transgene, twelve heterozygous plants, and six homozygous plants. Each $T_1$ plant was individually bagged before flowering to prevent out-crossing. $T_2$ seeds from each of the twenty four $T_1$ plants were harvested separately.

The $T_2$ seed stocks were used to identify which of the twenty four parent $T_1$ plants were null, heterozygous, or homozygous. Approximately thirty $T_2$ seeds from each $T_1$ plant were germinated on filter paper in petri dishes with a solution containing the antibiotic G418, an analog of kanamycin. Since the plants were co-transformed with the nptII resistance gene as a selectable marker, only those seeds carrying the transgene would germinate and continue to grow. If all the seeds on a plate proved to be sensitive to G418, then the $T_1$ parent was identified as a null line. If all the seeds on a plate were resistant to G418, then the $T_1$ parent was identified as a homozygous line. If approximately one quarter of the seeds on a plate were sensitive and the rest resistant, the $T_1$ parent was identified as a heterozygous line. $T_2$ seeds from homozygous $T_1$ parents from the same transformation event were bulked to generate homozygous seed stocks for field trial testing. $T_2$ seeds from null $T_1$ parents from the same transformation event were bulked to generate null sibling seed stocks for field trial testing.
Field Trial Design The effect of the AtKrp1(F173A;F175A) transgene on yield traits in the transgenic canola lines was evaluated by comparing each transgenic line directly with its null sibling in the field in large scale replicated trials. Since the null sibling arises from segregation of the transgene in the $T_1$ generation, the null and homozygous siblings are nearly identical genetically. The only significant difference is the presence or absence of the AtKrp1(F173A;F175A) transgene. This near genetic identity makes the null sibling the optimal control for evaluation of the effect of the AtKrp1 (F173A;F175A) transgene. As the main objective of the trial was the comparison of the transgenic line from an event to its null segregant, a split plot design was chosen. This design gives a high level of evaluation to the interaction between the transgenic and non-transgenic subentries and the differences between transgenic subplots between events (the interaction of subplot and main plot) and a lower level of evaluation to the differences between overall events or the main plot.

Field trials were conducted at multiple locations across the prairie provinces to assess yield phenotypes under the range of environmental conditions in which canola is typically grown. At all locations, each transgenic event was physically paired with its null sibling in adjacent plots. Each plot pair of homozygous and null siblings was replicated four times at each trial location. The locations of the four replicate plot pairs in each trial were randomly distributed at each trial location. Plots were 1.6 m by 6 m and planted at a density of approximately 142 seeds per square meter. Plants were grown to maturity using standard agronomic practices typical to commercial production of canola.

Example 13

Increased Yield in Transgenic Canola Expressing AtKrp1(F173A;F175A) During Embryo Development Using Embryo-Specific Promoters All plots at each yield field trial location were individually harvested with a combine. Total seed yield data were collected as total seed weight adjusted for moisture content from each plot. For every transgenic event in each trial, the mean of the total yield from the four replicate plots of each homozygous line was compared to the mean of the total yield from the four replicate plots of the associated null sibling line. This comparison was used to evaluate the effect of the AtKrp1(F173A;F175A) transgene on total seed yield. Results from each of the multiple trial locations were combined to give an across trials analysis of the effect of the AtKrp1(F173A;F175A) transgene on total seed yield. Statistical analysis of variance at each trial location permitted the assignment of a threshold for significance (P=0.05) for differences in total seed yield between homozygous transgenic lines and their null siblings.

The transgenic AtKrp1(F173A;F175A) canola lines that showed a statistically significant increase in total seed yield are summarized in Table 3. These results demonstrate that over expression of AtKrp1(F173A;F175A) using an embryo-specific promoter (LFAH12) results in increased seed yield.

TABLE 3

Change in total seed yield in homozygous AtKrp1(F173A; F175A) plants relative to their null siblings. All values are statistically significant (P = 0.05)

| Event | Promoter | Transgene | % Yield Increase |
|---|---|---|---|
| TG39-2 | LFAH12 | AtKrp1(F173A; F175A) | 13.0 |
| TG39-26 | LFAH12 | AtKrp1(F173A; F175A) | 18.6 |
| TG39-32 | LFAH12 | AtKrp1(F173A; F175A) | 12.0 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

The invention claimed is:

1. A recombinant nucleic acid encoding a plant mutant CDK inhibitor (CKI) polypeptide, wherein the mutant plant CKI polypeptide comprises: a CKI amino acid sequence having at least two modifications relative to a wild-type plant CKI polypeptide, said wild-type CKI polypeptide comprising (a) a cyclin binding region conferring binding affinity for a cyclin and (b) a cyclin dependent kinase (CDK) binding region conferring binding affinity for a CDK;
   wherein the wild-type CKI polypeptide binds to a cyclin/CDK complex;
   wherein the at least two modifications are within the CDK binding region;
   wherein the mutant CKI polypeptide can compete with said wild-type CKI for binding to the cyclin/CDK complex;
   wherein said wild-type plant CKI polypeptide is a kinase inhibitor protein (KIP) related protein (KRP) family member and wherein said mutant plant CKI polypeptide does not inhibit kinase activity of the cyclin/CDK complex;
   wherein said wild-type plant CKI polypeptide is from Canola, soy or corn; and
   wherein said at least two modifications are within the region corresponding to amino acids 145-168 of Brassica KRP1 (BnKRP1) polypeptide encoded by the nucleotide sequence of SEQ ID NO: 23, wherein each of the at least two modifications is an amino acid substitution at:
   (a) a position corresponding to amino acid 151 of BnKRP1; and
   (b) a position corresponding to amino acid 153 of BnKRP1,
   wherein the position corresponding to amino acid 151 of BnKRP1 is phenylalanine,
   wherein the position corresponding to amino acid 153 of BnKRP1 is phenylalanine, and
   wherein each amino acid substitution is with alanine.

2. A vector comprising a replicon and the recombinant nucleic acid of claim 1.

3. The vector of claim 2, which is an expression vector further comprising a promoter region operably linked to the recombinant nucleic acid.

4. The expression vector of claim 3, wherein the promoter is a constitutive promoter, an inducible promoter, a tissue-specific promoter, developmentally regulated promoter or a stage-specific promoter.

5. The expression vector of claim 4, wherein the constitutive promoter is a CaMV 35S promoter, the tissue-specific promoter is a seed specific promoter, and the stage-specific promoter is an embryo specific promoter.

6. A host cell comprising the recombinant nucleic acid of claim 1.

7. A method of producing a mutant CKI polypeptide, said method comprising: culturing the host cell of claim 6 under conditions suitable for expression of the nucleic acid encoding the mutant CKI polypeptide.

8. A transgenic plant comprising the recombinant nucleic acid of claim 1, wherein the transgenic plant is Canola, soy or corn.

9. A method of producing the transgenic plant of claim 8, comprising:
   introducing into a plant a vector comprising the recombinant nucleic acid of claim 1.

10. A method of modulating cell division in a plant cell expressing a wild-type CKI polypeptide, said wild-type CKI polypeptide comprising (a) a cyclin binding region conferring binding affinity for a cyclin and (b) a CDK binding region conferring binding affinity for a CDK, the method comprising: expressing within the cell a mutant CKI polypeptide encoded by the recombinant nucleic acid of claim 1, wherein the plant cell is from Canola, soy or corn.

11. A method for increasing plant vigor, root mass, fruit size, plant seed size, plant seed number, plant yield, plant biomass, early germination, or cell division in a plant compared to a wild-type plant, comprising: expressing within the plant a mutant KRP polypeptide encoded by the recombinant nucleic acid of claim 1, wherein the plant is Canola, soy or corn.

12. A recombinant CKI polypeptide encoded by the recombinant nucleic acid of claim 1.

* * * * *

SEQUENCE LISTING

```
<160> NUMBER OF SEQ ID NOS: 101

<210> SEQ ID NO 1
<211> LENGTH: 7
<212> TYPE: PRT
<213> ORGANISM: Arabidopsis thaliana

<400> SEQUENCE: 1

Pro Ser Thr Ala Ile Arg Glu
1               5

<210> SEQ ID NO 2
<211> LENGTH: 191
<212> TYPE: PRT
<213> ORGANISM: Arabidopsis thaliana

<400> SEQUENCE: 2

Met Val Arg Lys Tyr Arg Lys Ala Lys Gly Ile Val Glu Ala Gly Val
1               5                   10                  15

Ser Ser Thr Tyr Met Gln Leu Arg Ser Arg Arg Ile Val Tyr Val Arg
                20                  25                  30

Ser Glu Lys Ser Ser Ser Val Ser Val Val Gly Asp Asn Gly Val Ser
            35                  40                  45

Ser Ser Cys Ser Gly Ser Asn Glu Tyr Lys Lys Lys Glu Leu Ile His
        50                  55                  60

Leu Glu Glu Glu Asp Lys Asp Gly Asp Thr Glu Thr Ser Thr Tyr Arg
65                  70                  75                  80

Arg Gly Thr Lys Arg Lys Leu Phe Glu Asn Leu Arg Glu Glu Glu Lys
                85                  90                  95

Glu Glu Leu Ser Lys Ser Met Glu Asn Tyr Ser Ser Glu Phe Glu Ser
            100                 105                 110

Ala Val Lys Glu Ser Leu Asp Cys Cys Cys Ser Gly Arg Lys Thr Met
        115                 120                 125

Glu Glu Thr Val Thr Ala Glu Glu Glu Lys Ala Lys Leu Met Thr
    130                 135                 140

Glu Met Pro Thr Glu Ser Glu Ile Glu Asp Phe Phe Val Glu Ala Glu
145                 150                 155                 160

Lys Gln Leu Lys Glu Lys Phe Lys Lys Lys Tyr Asn Phe Asp Phe Glu
                165                 170                 175

Lys Glu Lys Pro Leu Glu Gly Arg Tyr Glu Trp Val Lys Leu Glu
            180                 185                 190
```

<210> SEQ ID NO 3
<211> LENGTH: 209
<212> TYPE: PRT
<213> ORGANISM: Arabidopsis thaliana

<400> SEQUENCE: 3

Met Ala Ala Val Arg Arg Glu Arg Asp Val Val Glu Glu Asn Gly
1               5                   10                  15

Val Thr Thr Thr Thr Val Lys Arg Arg Lys Met Glu Glu Glu Val Asp
            20                  25                  30

Leu Val Glu Ser Arg Ile Ile Leu Ser Pro Cys Val Gln Ala Thr Asn
        35                  40                  45

Arg Gly Gly Ile Val Ala Arg Asn Ser Ala Gly Ala Ser Glu Thr Ser
    50                  55                  60

Val Val Ile Val Arg Arg Arg Asp Ser Pro Val Glu Glu Gln Cys
65                  70                  75                  80

Gln Ile Glu Glu Glu Asp Ser Ser Val Ser Cys Cys Ser Thr Ser Glu
                85                  90                  95

Glu Lys Ser Lys Arg Arg Ile Glu Phe Val Asp Leu Glu Glu Asn Asn
            100                 105                 110

Gly Asp Asp Arg Glu Thr Glu Thr Ser Trp Ile Tyr Asp Asp Leu Asn
        115                 120                 125

Lys Ser Glu Glu Ser Met Asn Met Asp Ser Ser Val Ala Val Glu
    130                 135                 140

Asp Val Glu Ser Arg Arg Arg Leu Arg Lys Ser Leu His Glu Thr Val
145                 150                 155                 160

Lys Glu Ala Glu Leu Glu Asp Phe Phe Gln Val Ala Glu Lys Asp Leu
                165                 170                 175

Arg Asn Lys Leu Leu Glu Cys Ser Met Lys Tyr Asn Phe Asp Phe Glu
            180                 185                 190

Lys Asp Glu Pro Leu Gly Gly Gly Arg Tyr Glu Trp Val Lys Leu Asn
        195                 200                 205

Pro

<210> SEQ ID NO 4
<211> LENGTH: 222
<212> TYPE: PRT
<213> ORGANISM: Arabidopsis thaliana

<400> SEQUENCE: 4

Met Gly Lys Tyr Met Lys Lys Ser Lys Ile Thr Gly Asp Ile Ser Val
1               5                   10                  15

Met Glu Val Ser Lys Ala Thr Ala Pro Ser Pro Gly Val Arg Thr Arg
            20                  25                  30

Ala Ala Lys Thr Leu Ala Leu Lys Arg Leu Asn Ser Ser Ala Ala Asp
        35                  40                  45

Ser Ala Leu Pro Asn Asp Ser Ser Cys Tyr Leu Gln Leu Arg Ser Arg
    50                  55                  60

Arg Leu Glu Lys Pro Ser Ser Leu Ile Glu Pro Lys Gln Pro Pro Arg
65                  70                  75                  80

Val His Arg Ser Gly Ile Lys Glu Ser Gly Ser Arg Ser Arg Val Asp
                85                  90                  95

Ser Val Asn Ser Val Pro Val Ala Gln Ser Ser Asn Glu Asp Glu Cys
            100                 105                 110

```
Phe Asp Asn Phe Val Ser Val Gln Val Ser Cys Gly Glu Asn Ser Leu
            115                 120                 125

Gly Phe Glu Ser Arg His Ser Thr Arg Glu Ser Thr Pro Cys Asn Phe
    130                 135                 140

Val Glu Asp Met Glu Ile Met Val Thr Pro Gly Ser Ser Thr Arg Ser
145                 150                 155                 160

Met Cys Arg Ala Thr Lys Glu Tyr Thr Arg Glu Gln Asp Asn Val Ile
                165                 170                 175

Pro Thr Thr Ser Glu Met Glu Glu Phe Phe Ala Tyr Ala Glu Gln Gln
            180                 185                 190

Gln Gln Arg Leu Phe Met Glu Lys Tyr Asn Phe Asp Ile Val Asn Asp
        195                 200                 205

Ile Pro Leu Ser Gly Arg Tyr Glu Trp Val Gln Val Lys Pro
    210                 215                 220
```

<210> SEQ ID NO 5
<211> LENGTH: 289
<212> TYPE: PRT
<213> ORGANISM: Arabidopsis thaliana

<400> SEQUENCE: 5

```
Met Gly Lys Tyr Ile Arg Lys Ser Lys Ile Asp Gly Ala Gly Ala Gly
1               5                   10                  15

Ala Gly Gly Gly Gly Gly Gly Gly Gly Glu Ser Ser Ile Ala
            20                  25                  30

Leu Met Asp Val Val Ser Pro Ser Ser Ser Ser Leu Gly Val Leu
            35                  40                  45

Thr Arg Ala Lys Ser Leu Ala Leu Gln Gln Gln Gln Arg Cys Leu
50                  55                  60

Leu Gln Lys Pro Ser Pro Ser Ser Leu Pro Pro Thr Ser Ala Ser
65                  70                  75                  80

Pro Asn Pro Pro Ser Lys Gln Lys Met Lys Lys Lys Gln Gln Met
                85                  90                  95

Asn Asp Cys Gly Ser Tyr Leu Gln Leu Arg Ser Arg Arg Leu Gln Lys
                100                 105                 110

Lys Pro Pro Ile Val Val Ile Arg Ser Thr Lys Arg Arg Lys Gln Gln
            115                 120                 125

Arg Arg Asn Glu Thr Cys Gly Arg Asn Pro Asn Pro Arg Ser Asn Leu
    130                 135                 140

Asp Ser Ile Arg Gly Asp Gly Ser Arg Ser Asp Ser Val Ser Glu Ser
145                 150                 155                 160

Val Val Phe Gly Lys Asp Lys Asp Leu Ile Ser Glu Ile Asn Lys Asp
                165                 170                 175

Pro Thr Phe Gly Gln Asn Phe Phe Asp Leu Glu Glu His Thr Gln
            180                 185                 190

Ser Phe Asn Arg Thr Thr Arg Glu Ser Thr Pro Cys Ser Leu Ile Arg
        195                 200                 205

Arg Pro Glu Ile Met Thr Thr Pro Gly Ser Ser Thr Lys Leu Asn Ile
    210                 215                 220

Cys Val Ser Glu Ser Asn Gln Arg Glu Asp Ser Leu Ser Arg Ser His
225                 230                 235                 240

Arg Arg Arg Pro Thr Thr Pro Glu Met Asp Glu Phe Phe Ser Gly Ala
                245                 250                 255

Glu Glu Glu Gln Gln Lys Gln Phe Ile Glu Lys Tyr Asn Phe Asp Pro
            260                 265                 270
```

Val Asn Glu Gln Pro Leu Pro Gly Arg Phe Glu Trp Thr Lys Val Asp
        275                 280                 285

Asp

<210> SEQ ID NO 6
<211> LENGTH: 189
<212> TYPE: PRT
<213> ORGANISM: Arabidopsis thaliana

<400> SEQUENCE: 6

Met Gly Lys Tyr Ile Lys Lys Ser Lys Val Ala Gly Ala Val Ser Val
1               5                   10                  15

Lys Asp Lys Ser His Pro Pro Ala Leu Gly Phe Arg Thr Arg Ala Ala
            20                  25                  30

Ala Ala Lys Asn Leu Ala Leu His Arg Leu Arg Ser His Ser Asp Glu
        35                  40                  45

Ala Asp Ser Phe Asn Tyr Leu Gln Leu Arg Ser Arg Arg Leu Val Lys
    50                  55                  60

Leu Pro Leu Leu Thr Asn Thr Arg Lys Gln Gln Lys Gln Gln Leu Ile
65                  70                  75                  80

Pro Ser Val Asn Gln Cys Gln Thr Lys Asn Pro Arg Ala Ser Ser Gly
                85                  90                  95

Pro Ala Lys Lys Leu Glu Pro Asp Thr Thr Thr Glu Gly Ala Cys Gly
            100                 105                 110

Asp Asn Glu Arg Ile Ser Arg Ser Asp Cys Asn Phe Gly Asp Lys Gly
        115                 120                 125

Phe Asp Leu Glu Ser Glu Asn Arg Ser Met Ile Ser Asp Ser Lys Ser
    130                 135                 140

Ile Gln Ser Glu Ile Glu Asp Phe Phe Ala Ser Ala Glu Gln Gln Gln
145                 150                 155                 160

Gln Arg Phe Phe Ile Gln Lys Tyr Asn Phe Asp Ile Val Ser Asp Asn
                165                 170                 175

Pro Leu Pro Gly Arg Tyr Glu Trp Val Lys Val Met Pro
            180                 185

<210> SEQ ID NO 7
<211> LENGTH: 196
<212> TYPE: PRT
<213> ORGANISM: Arabidopsis thaliana

<400> SEQUENCE: 7

Met Ser Glu Arg Lys Arg Glu Leu Ala Glu Ala Ser Ser Thr Ser
1               5                   10                  15

Phe Ser Pro Leu Lys Lys Thr Lys Leu Asn Asp Ser Ser Asp Ser Ser
            20                  25                  30

Pro Asp Ser His Asp Val Ile Val Phe Ala Val Ser Ser Ser Ser Val
        35                  40                  45

Ala Ser Ser Ala Ala Leu Ala Ser Asp Glu Cys Ser Val Thr Ile Gly
    50                  55                  60

Gly Glu Glu Ser Asp Gln Ser Ser Ile Ser Ser Gly Cys Phe Thr
65                  70                  75                  80

Ser Glu Ser Lys Glu Ile Ala Lys Asn Ser Ser Ser Phe Gly Val Asp
                85                  90                  95

Leu Glu Asp His Gln Ile Glu Thr Glu Thr Glu Thr Ser Thr Phe Ile
            100                 105                 110

```
Thr Ser Asn Phe Arg Lys Glu Thr Ser Pro Val Ser Glu Gly Leu Gly
            115                 120                 125

Glu Thr Thr Thr Glu Met Glu Ser Ser Ser Ala Thr Lys Arg Lys Gln
            130                 135                 140

Pro Gly Val Arg Lys Thr Pro Thr Ala Ala Glu Ile Glu Asp Leu Phe
145                 150                 155                 160

Ser Glu Leu Glu Ser Pro Asp Asp Lys Lys Lys Gln Phe Ile Glu Lys
                165                 170                 175

Tyr Asn Phe Asp Ile Val Asn Asp Glu Pro Leu Glu Gly Arg Tyr Lys
            180                 185                 190

Trp Asp Arg Leu
        195

<210> SEQ ID NO 8
<211> LENGTH: 195
<212> TYPE: PRT
<213> ORGANISM: Arabidopsis thaliana

<400> SEQUENCE: 8

Met Ser Glu Thr Lys Pro Lys Arg Asp Ser Glu Tyr Glu Gly Ser Asn
1               5                   10                  15

Ile Lys Arg Met Arg Leu Asp Asp Asp Asp Val Leu Arg Ser Pro
            20                  25                  30

Thr Arg Thr Leu Ser Ser Ser Ser Ser Ser Leu Ala Tyr Ser Val
            35                  40                  45

Ser Asp Ser Gly Gly Phe Cys Ser Val Ala Leu Ser Glu Glu Glu Asp
        50                  55                  60

Asp His Leu Ser Ser Ser Ile Ser Ser Gly Cys Ser Ser Ser Glu Thr
65                  70                  75                  80

Asn Glu Ile Ala Thr Arg Leu Pro Phe Ser Asp Leu Glu Ala His Glu
                85                  90                  95

Ile Ser Glu Thr Glu Ile Ser Thr Leu Leu Thr Asn Asn Phe Arg Lys
            100                 105                 110

Gln Gly Ile Ser Ser Ser Glu Asn Leu Gly Glu Thr Ala Glu Met Asp
            115                 120                 125

Ser Ala Thr Thr Glu Met Arg Asp Gln Arg Lys Thr Glu Lys Lys Lys
            130                 135                 140

Lys Met Glu Lys Ser Pro Thr Gln Ala Glu Leu Asp Asp Phe Ser
145                 150                 155                 160

Ala Ala Glu Arg Tyr Glu Gln Lys Arg Phe Thr Glu Lys Tyr Asn Tyr
                165                 170                 175

Asp Ile Val Asn Asp Thr Pro Leu Glu Gly Arg Tyr Gln Trp Val Ser
            180                 185                 190

Leu Lys Pro
        195

<210> SEQ ID NO 9
<211> LENGTH: 49
<212> TYPE: PRT
<213> ORGANISM: Zea mays

<400> SEQUENCE: 9

Val Pro Pro Ala Gln Glu Ile Gln Glu Phe Phe Ala Ala Ala Glu Ala
1               5                   10                  15

Ala His Ala Lys Arg Phe Ala Ser Lys Tyr Asn Phe Asp Phe Val Arg
            20                  25                  30
```

```
Gly Val Pro Leu Asp Ala Gly Arg Phe Glu Trp Thr Pro Gly Val Ser
            35                  40                  45

Ile

<210> SEQ ID NO 10
<211> LENGTH: 40
<212> TYPE: PRT
<213> ORGANISM: Gossypium hirsutum
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 10

Ile Pro Ser Xaa Ala Glu Ile Asp Glu Phe Phe Ser Val Ala Glu Lys
1               5                   10                  15

Tyr Glu Gln Xaa Arg Phe Ala Glu Lys Tyr Xaa Tyr Asp Ile Val Xaa
            20                  25                  30

Asp Val Pro Leu Asp Gly Arg Tyr
            35                  40

<210> SEQ ID NO 11
<211> LENGTH: 45
<212> TYPE: PRT
<213> ORGANISM: Glycine max

<400> SEQUENCE: 11

Val Pro Thr Glu Ser Glu Leu Glu Asp Phe Phe Ala Ala Ala Glu Lys
1               5                   10                  15

Asp Ile Gln Lys Arg Phe Thr Asp Lys Tyr Asn Tyr Asp Phe Val Lys
            20                  25                  30

Asp Met Pro Leu Glu Gly Arg Tyr Glu Trp Val Gln Leu
            35                  40                  45

<210> SEQ ID NO 12
<211> LENGTH: 45
<212> TYPE: PRT
<213> ORGANISM: Populus tremula

<400> SEQUENCE: 12

Ile Pro Thr Thr Cys Glu Met Asp Glu Phe Phe Ala Gly Val Glu Gln
1               5                   10                  15

Gln Gln Gln Arg Leu Phe Ile Glu Lys Tyr Asn Phe Asp Ile Val Asn
            20                  25                  30

Asp Leu Pro Leu Ser Gly Arg Tyr Glu Trp Val Arg Val
            35                  40                  45

<210> SEQ ID NO 13
<211> LENGTH: 47
<212> TYPE: PRT
<213> ORGANISM: Nicotiana tabacum

<400> SEQUENCE: 13
```

```
Met Pro Ser Glu Lys Glu Ile Glu Glu Phe Ala Ala Arg Gln Lys
1               5                   10                  15

Ala Ile Leu Lys Arg Phe Arg Lys Tyr Asn Phe Asp Glu Lys
            20                  25                  30

Glu Glu Pro Leu Glu Gly Arg Tyr Glu Trp Val Arg Ile Gly Ser
            35                  40                  45
```

<210> SEQ ID NO 14
<211> LENGTH: 47
<212> TYPE: PRT
<213> ORGANISM: Triticum aestivum

<400> SEQUENCE: 14

```
Ile Pro Cys Ser Ala Glu Met Asn Glu Phe Phe Ser Ala Ala Glu Gln
1               5                   10                  15

Pro Gln Gln Gln Ala Phe Ile Asp Lys Tyr Asn Phe Asp Pro Val Asn
            20                  25                  30

Asp Cys Pro Leu Pro Gly Arg Tyr Glu Trp Val Lys Leu Asp Glx
            35                  40                  45
```

<210> SEQ ID NO 15
<211> LENGTH: 47
<212> TYPE: PRT
<213> ORGANISM: Triticum aestivum

<400> SEQUENCE: 15

```
Val Pro Ser Ser Leu Glu Met Asp Glu Phe Phe Ala Ala Ala Glu Gln
1               5                   10                  15

Gln Gln His Gln Thr Phe Arg Glu Lys Tyr Asn Phe Cys Pro Ala Ser
            20                  25                  30

Glu Arg Pro Leu Pro Gly Arg Tyr Glu Trp Thr Val Leu Asp Cys
            35                  40                  45
```

<210> SEQ ID NO 16
<211> LENGTH: 45
<212> TYPE: PRT
<213> ORGANISM: Oryza sativa

<400> SEQUENCE: 16

```
Ile Pro Ala Ser Ala Glu Leu Glu Ala Phe Phe Ala Ala Glu Glu Gln
1               5                   10                  15

Arg Gln Arg Gln Ala Phe Ile Asp Lys Tyr Asn Phe Asp Pro Val Asn
            20                  25                  30

Asp Cys Pro Leu Pro Gly Arg Phe Glu Trp Val Lys Leu
            35                  40                  45
```

<210> SEQ ID NO 17
<211> LENGTH: 42
<212> TYPE: PRT
<213> ORGANISM: Solanum tuberosum

<400> SEQUENCE: 17

```
Ser Glu Ala Glu Leu Asp Glu Phe Phe Ala Ala Ala Glu Lys Asp Leu
1               5                   10                  15

His Lys His Phe Ala Glu Lys Tyr Asn Phe Asp Phe Ala Lys Glu Glu
            20                  25                  30

Pro Leu Glu Gly Arg Tyr Glu Trp Val Arg
            35                  40
```

```
<210> SEQ ID NO 18
<211> LENGTH: 9
<212> TYPE: PRT
<213> ORGANISM: FLAG epitope

<400> SEQUENCE: 18

Met Asp Tyr Lys Ala Phe Asp Asn Leu
1               5

<210> SEQ ID NO 19
<211> LENGTH: 9
<212> TYPE: PRT
<213> ORGANISM: hemegglutinin (HA) epitope

<400> SEQUENCE: 19

Tyr Pro Tyr Asp Val Pro Asp Tyr Ala
1               5

<210> SEQ ID NO 20
<211> LENGTH: 24
<212> TYPE: DNA
<213> ORGANISM: Artificial Sequence
<220> FEATURE:
<223> OTHER INFORMATION: PCR

<400> SEQUENCE: 20
atggtgagaa aatatagaaa agct                                            24

<210> SEQ ID NO 21
<211> LENGTH: 24
<212> TYPE: DNA
<213> ORGANISM: Artificial Sequence
<220> FEATURE:
<223> OTHER INFORMATION: PCR

<400> SEQUENCE: 21
tcactctaac tttacccatt cgta                                            24

<210> SEQ ID NO 22
<211> LENGTH: 45
<212> TYPE: DNA
<213> ORGANISM: Artificial Sequence
<220> FEATURE:
<223> OTHER INFORMATION: RACE primer

<400> SEQUENCE: 22
ctctgataat ttaacccact cgtagcgtcc ttctaatggc ttctc                     45

<210> SEQ ID NO 23
<211> LENGTH: 513
<212> TYPE: DNA
<213> ORGANISM: Brassica napus

<400> SEQUENCE: 23
atggtgagaa atgcagaaa aactaaaggg acggtgggag cttcgtctac gtatatgcag      60
cttcgcagcc ggagaatcgt ttacagatcg gaaaaagcta gctcgtcgtc gtcgtcttgt    120
tgcgcgagta acaacaatgg agttatagat cttgaggagg aaagagatgg tgagactgaa    180
acgtcgtcgt gtcgacggag tagtaagagg aagctatttg aaaaccttag agaaaaagaa    240
tctatggaga attcacagca aatcgtagct ggttttgatt ccgccgtgaa agaatcatcg    300
gattgttgtt gcagccggag aacatctttg tcaacgacgg aggagaaggg gaaatcagcg    360
acggagcaac caccaacggc agtggagatt gaagattttt tcgtggaagc tgagaaacag    420
```

```
ctccatgata atttcaagaa gaagtataac tttgatttcg aaaaggagaa gccattagaa      480
ggacgctacg agtgggttaa attatcagag taa                                   513
```

<210> SEQ ID NO 24
<211> LENGTH: 28
<212> TYPE: DNA
<213> ORGANISM: Artificial Sequence
<220> FEATURE:
<223> OTHER INFORMATION: PCR

<400> SEQUENCE: 24

```
acggatccca tatggtgaga aaatatag                                         28
```

<210> SEQ ID NO 25
<211> LENGTH: 25
<212> TYPE: DNA
<213> ORGANISM: Artificial Sequence
<220> FEATURE:
<223> OTHER INFORMATION: PCR

<400> SEQUENCE: 25

```
atcgctcgag tcactctaac tttac                                            25
```

<210> SEQ ID NO 26
<211> LENGTH: 26
<212> TYPE: DNA
<213> ORGANISM: Artificial Sequence
<220> FEATURE:
<223> OTHER INFORMATION: PCR

<400> SEQUENCE: 26

```
acggatccca tatggtgaga aaatgc                                           26
```

<210> SEQ ID NO 27
<211> LENGTH: 28
<212> TYPE: DNA
<213> ORGANISM: Artificial Sequence
<220> FEATURE:
<223> OTHER INFORMATION: PCR

<400> SEQUENCE: 27

```
atcgctcgag tcactctgat aatttaac                                         28
```

<210> SEQ ID NO 28
<211> LENGTH: 43
<212> TYPE: DNA
<213> ORGANISM: Artificial Sequence
<220> FEATURE:
<223> OTHER INFORMATION: site directed mutagenesis-sense

<400> SEQUENCE: 28

```
ggagcaacca ccaacggcag tggctgctgc tgcttttttc gtg                        43
```

<210> SEQ ID NO 29
<211> LENGTH: 43
<212> TYPE: DNA
<213> ORGANISM: Artificial Sequence
<220> FEATURE:
<223> OTHER INFORMATION: site directed mutagenesis anti-sense

<400> SEQUENCE: 29

```
cacgaaaaaa gcagcagcag ccactgccgt tggtggttgc tcc                        43
```

<210> SEQ ID NO 30
<211> LENGTH: 50

```
<212> TYPE: DNA
<213> ORGANISM: Artificial Sequence
<220> FEATURE:
<223> OTHER INFORMATION: site directed mutagenesis-sense

<400> SEQUENCE: 30
ccttctaatg gcttctcctt ttcagcatca gcgttatact tcttcttgaa              50

<210> SEQ ID NO 31
<211> LENGTH: 50
<212> TYPE: DNA
<213> ORGANISM: Artificial Sequence
<220> FEATURE:
<223> OTHER INFORMATION: site directed mutagenesis anti-sense

<400> SEQUENCE: 31
ttcaagaaga agtataacgc tgatgctgaa aaggagaagc cattagaagg              50

<210> SEQ ID NO 32
<211> LENGTH: 45
<212> TYPE: DNA
<213> ORGANISM: Artificial Sequence
<220> FEATURE:
<223> OTHER INFORMATION: site directed mutagenesis anti-sense

<400> SEQUENCE: 32
ttcaagaaga agtacaatgc cgatgccgag aaggagaagc catta                   45

<210> SEQ ID NO 33
<211> LENGTH: 45
<212> TYPE: DNA
<213> ORGANISM: Artificial Sequence
<220> FEATURE:
<223> OTHER INFORMATION: site directed mutagenesis

<400> SEQUENCE: 33
ttatggcttc tccttctggg catcggcatt gtacttcttc ttgaa                   45

<210> SEQ ID NO 34
<211> LENGTH: 33
<212> TYPE: DNA
<213> ORGANISM: Artificial Sequence
<220> FEATURE:
<223> OTHER INFORMATION: site directed mutagenesis-sense

<400> SEQUENCE: 34
gataatttca agaaggcgta aactttgat ttc                                 33

<210> SEQ ID NO 35
<211> LENGTH: 33
<212> TYPE: DNA
<213> ORGANISM: Artificial Sequence
<220> FEATURE:
<223> OTHER INFORMATION: site directed mutagenesis anti-sense

<400> SEQUENCE: 35
gaaatcaaag ttatacgcct tcttgaaatt atc                                33

<210> SEQ ID NO 36
<211> LENGTH: 33
<212> TYPE: DNA
<213> ORGANISM: Artificial Sequence
<220> FEATURE:
<223> OTHER INFORMATION: site directed mutagenesis-sense

<400> SEQUENCE: 36
```

```
aatttcaaga agaaggctaa ctttgatttc gaa                                33
```

<210> SEQ ID NO 37
<211> LENGTH: 33
<212> TYPE: DNA
<213> ORGANISM: Artificial Sequence
<220> FEATURE:
<223> OTHER INFORMATION: site directed mutagenesis anti-sense

<400> SEQUENCE: 37

```
ttcgaaatca aagttagcct tcttcttgaa att                                33
```

<210> SEQ ID NO 38
<211> LENGTH: 33
<212> TYPE: DNA
<213> ORGANISM: Artificial Sequence
<220> FEATURE:
<223> OTHER INFORMATION: site directed mutagenesis-sense

<400> SEQUENCE: 38

```
ttcaagaaga agtatgcctt tgatttcgaa aag                                33
```

<210> SEQ ID NO 39
<211> LENGTH: 33
<212> TYPE: DNA
<213> ORGANISM: Artificial Sequence
<220> FEATURE:
<223> OTHER INFORMATION: site directed mutagenesis anti-sense

<400> SEQUENCE: 39

```
cttttcgaaa tcaaaggcat acttcttctt gaa                                33
```

<210> SEQ ID NO 40
<211> LENGTH: 31
<212> TYPE: DNA
<213> ORGANISM: Artificial Sequence
<220> FEATURE:
<223> OTHER INFORMATION: site directed mutagenesis-sense

<400> SEQUENCE: 40

```
agaagaagta taacgctgat ttcggaaagg a                                  31
```

<210> SEQ ID NO 41
<211> LENGTH: 31
<212> TYPE: DNA
<213> ORGANISM: Artificial Sequence
<220> FEATURE:
<223> OTHER INFORMATION: site directed mutagenesis anti-sense

<400> SEQUENCE: 41

```
tcctttttcga aatcagcgtt atacttcttc t                                 31
```

<210> SEQ ID NO 42
<211> LENGTH: 31
<212> TYPE: DNA
<213> ORGANISM: Artificial Sequence
<220> FEATURE:
<223> OTHER INFORMATION: site directed mutagenesis-sense

<400> SEQUENCE: 42

```
agtataactt tgatgccgaa aaggagaagc c                                  31
```

<210> SEQ ID NO 43
<211> LENGTH: 31
<212> TYPE: DNA
<213> ORGANISM: Artificial Sequence

```
<220> FEATURE:
<223> OTHER INFORMATION: site directed mutagenesis anti-sense

<400> SEQUENCE: 43
ggcttctcct tttcggcatc aaagttatac t                              31

<210> SEQ ID NO 44
<211> LENGTH: 34
<212> TYPE: DNA
<213> ORGANISM: Artificial Sequence
<220> FEATURE:
<223> OTHER INFORMATION: site directed mutagenesis-sense

<400> SEQUENCE: 44
gatttcgaaa aggaggcggc attagaagga cgct                           34

<210> SEQ ID NO 45
<211> LENGTH: 34
<212> TYPE: DNA
<213> ORGANISM: Artificial Sequence
<220> FEATURE:
<223> OTHER INFORMATION: site directed mutagenesis anti-sense

<400> SEQUENCE: 45
agcgtccttc taatgccgcc tccttttcga aatc                           34

<210> SEQ ID NO 46
<211> LENGTH: 33
<212> TYPE: DNA
<213> ORGANISM: Artificial Sequence
<220> FEATURE:
<223> OTHER INFORMATION: site directed mutagenesis-sense

<400> SEQUENCE: 46
gccattagaa ggagccgccg agtgggttaa att                            33

<210> SEQ ID NO 47
<211> LENGTH: 33
<212> TYPE: DNA
<213> ORGANISM: Artificial Sequence
<220> FEATURE:
<223> OTHER INFORMATION: site directed mutagenesis anti-sense

<400> SEQUENCE: 47
aatttaaccc actcggcggc tccttctaat ggc                            33

<210> SEQ ID NO 48
<211> LENGTH: 33
<212> TYPE: DNA
<213> ORGANISM: Artificial Sequence
<220> FEATURE:
<223> OTHER INFORMATION: site directed mutagenesis-sense

<400> SEQUENCE: 48
agaaggacgc tacgcggcgg ttaaattatc aga                            33

<210> SEQ ID NO 49
<211> LENGTH: 33
<212> TYPE: DNA
<213> ORGANISM: Artificial Sequence
<220> FEATURE:
<223> OTHER INFORMATION: site directed mutagenesis anti-sense

<400> SEQUENCE: 49
tctgataatt taaccgccgc gtagcgtcct tct                            33
```

-continued

<210> SEQ ID NO 50
<211> LENGTH: 34
<212> TYPE: DNA
<213> ORGANISM: Artificial Sequence
<220> FEATURE:
<223> OTHER INFORMATION: site directed mutagenesis-sense

<400> SEQUENCE: 50
cgctacgagt gggttgcagc atcagagtga gagc                           34

<210> SEQ ID NO 51
<211> LENGTH: 34
<212> TYPE: DNA
<213> ORGANISM: Artificial Sequence
<220> FEATURE:
<223> OTHER INFORMATION: site directed mutagenesis anti-sense

<400> SEQUENCE: 51
gctctcactc tgatgctgca acccactcgt agcg                           34

<210> SEQ ID NO 52
<211> LENGTH: 50
<212> TYPE: DNA
<213> ORGANISM: Artificial Sequence
<220> FEATURE:
<223> OTHER INFORMATION: site directed mutagenesis anti-sense

<400> SEQUENCE: 52
ccttctaatg gcttctcctt ttcagcatca gcgttatact tcttcttgaa           50

<210> SEQ ID NO 53
<211> LENGTH: 50
<212> TYPE: DNA
<213> ORGANISM: Artificial Sequence
<220> FEATURE:
<223> OTHER INFORMATION: site directed mutagenesis anti-sense

<400> SEQUENCE: 53
ttcaagaaga agtataacgc tgatgctgaa aaggagaagc cattagaagg           50

<210> SEQ ID NO 54
<211> LENGTH: 33
<212> TYPE: DNA
<213> ORGANISM: Artificial Sequence
<220> FEATURE:
<223> OTHER INFORMATION: site directed mutagenesis-sense

<400> SEQUENCE: 54
aatttcaaga agaaggctaa cgctgatgct gaa                            33

<210> SEQ ID NO 55
<211> LENGTH: 33
<212> TYPE: DNA
<213> ORGANISM: Artificial Sequence
<220> FEATURE:
<223> OTHER INFORMATION: site directed mutagenesis anti-sense

<400> SEQUENCE: 55
ttcagcatca gcgttagcct tcttcttgaa att                            33

<210> SEQ ID NO 56
<211> LENGTH: 33
<212> TYPE: DNA
<213> ORGANISM: Artificial Sequence
<220> FEATURE:
<223> OTHER INFORMATION: PCR

<400> SEQUENCE: 56
ctcgagtcaa gcagctaatt taacccactc gta                          33

<210> SEQ ID NO 57
<211> LENGTH: 24
<212> TYPE: DNA
<213> ORGANISM: Artificial Sequence
<220> FEATURE:
<223> OTHER INFORMATION: PCR

<400> SEQUENCE: 57
ctcgagtcac ttcttgaaat tatc                                   24

<210> SEQ ID NO 58
<211> LENGTH: 6
<212> TYPE: PRT
<213> ORGANISM: Arabidopsis thaliana

<400> SEQUENCE: 58

Lys Tyr Asn Phe Asp Phe
1               5

<210> SEQ ID NO 59
<211> LENGTH: 6
<212> TYPE: PRT
<213> ORGANISM: Artificial Sequence
<220> FEATURE:
<223> OTHER INFORMATION: mutant AtKrp2

<400> SEQUENCE: 59

Lys Ala Ala Ala Ala Ala
1               5

<210> SEQ ID NO 60
<211> LENGTH: 27
<212> TYPE: DNA
<213> ORGANISM: Artificial Sequence
<220> FEATURE:
<223> OTHER INFORMATION: PCR

<400> SEQUENCE: 60
ggatcccata tgggaaaata cataaag                                27

<210> SEQ ID NO 61
<211> LENGTH: 24
<212> TYPE: DNA
<213> ORGANISM: Artificial Sequence
<220> FEATURE:
<223> OTHER INFORMATION: PCR

<400> SEQUENCE: 61
ctcgagctaa tcatctacct tctt                                   24

<210> SEQ ID NO 62
<211> LENGTH: 27
<212> TYPE: DNA
<213> ORGANISM: Artificial Sequence
<220> FEATURE:
<223> OTHER INFORMATION: PCR

<400> SEQUENCE: 62
ggatcccata tgggcaagta catgcgc                                27

<210> SEQ ID NO 63

<210> SEQ ID NO 63
<211> LENGTH: 24
<212> TYPE: DNA
<213> ORGANISM: Artificial Sequence
<220> FEATURE:
<223> OTHER INFORMATION: PCR

<400> SEQUENCE: 63
ggatcctcag tctagcttca ccca                                          24

<210> SEQ ID NO 64
<211> LENGTH: 35
<212> TYPE: DNA
<213> ORGANISM: Artificial Sequence
<220> FEATURE:
<223> OTHER INFORMATION: PCR

<400> SEQUENCE: 64
ctcgaggaca tatggagatg gctcaggtta aggca                              35

<210> SEQ ID NO 65
<211> LENGTH: 31
<212> TYPE: DNA
<213> ORGANISM: Artificial Sequence
<220> FEATURE:
<223> OTHER INFORMATION: PCR

<400> SEQUENCE: 65
ctcgagtcaa ctgaacccac tcgtatcgtc c                                  31

<210> SEQ ID NO 66
<211> LENGTH: 45
<212> TYPE: DNA
<213> ORGANISM: Artificial Sequence
<220> FEATURE:
<223> OTHER INFORMATION: site directed mutagenesis

<400> SEQUENCE: 66
ttcaagaaga agtacaatgc cgatgccgag aaggagaagc catta                   45

<210> SEQ ID NO 67
<211> LENGTH: 45
<212> TYPE: DNA
<213> ORGANISM: Artificial Sequence
<220> FEATURE:
<223> OTHER INFORMATION: site directed mutagenesis

<400> SEQUENCE: 67
ttatggcttc tccttctggg catcggcatt gtacttcttc ttgaa                   45

<210> SEQ ID NO 68
<211> LENGTH: 168
<212> TYPE: PRT
<213> ORGANISM: Brassica napus

<400> SEQUENCE: 68

Met Val Arg Lys Cys Arg Lys Thr Lys Gly Thr Val Gly Ala Ser Ser
1               5                   10                  15

Thr Tyr Met Gln Leu Arg Ser Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
50                  55                  60

Arg Arg Ser Ser Lys Arg Lys Leu Phe Glu Asn Leu Arg Glu Lys Glu

Ser Met Glu Asn Ser Gln Gln Ile Val Ala Gly Phe Asp Ser Ala Val
65                  70                  75                  80

Lys Glu Ser Ser Asp Cys Cys Ser Arg Arg Thr Ser Leu Ser Thr
            85                  90                  95

Thr Glu Glu Lys Gly Lys Ser Ala Thr Glu Gln Pro Thr Ala Val
        100                 105                 110

Glu Ile Glu Asp Phe Phe Val Glu Ala Glu Lys Gln Leu His Asp Asn
115                 120                 125

Phe Lys Lys Lys Tyr Asn Phe Asp Phe Glu Lys Glu Lys Pro Leu Glu
130                 135                 140

Gly Arg Tyr Glu Trp Val Lys Leu
145                 150                 155                 160

165

<210> SEQ ID NO 69
<211> LENGTH: 192
<212> TYPE: PRT
<213> ORGANISM: Brassica napus

<400> SEQUENCE: 69

Met Gly Lys Tyr Ile Lys Ser Lys Ile Thr Gly Asp Ile Asp Ser
1               5                   10                  15

Met Glu Ala Thr Glu Ala Thr Ser Leu Gly Val Arg Thr Arg Ala Ala
            20                  25                  30

Ala Lys Thr Leu Ala Leu Lys Arg Leu Asn Ser Ser Ala Pro Asp
        35                  40                  45

Ser Ser Cys Tyr Leu Gln Leu Arg Ser Arg Arg Leu Glu Lys Pro Pro
50                  55                  60

Ser Leu Ala Glu Pro Arg Gln Val Lys Pro Gly Ile Lys Glu Ser Gly
65                  70                  75                  80

Ser Lys Ile Asp Ser Val Asn Ser Ser Val Ala Gly Ser Gly Asp Glu
                85                  90                  95

Cys Phe Cys Arg Glu Asn Ser Pro Glu Phe Gln Thr Arg Gln Ser Thr
            100                 105                 110

Arg Glu Ser Thr Pro Cys Asn Phe Val Glu Asp Leu Glu Thr Ile Val
        115                 120                 125

Thr Pro Gly Ser Ser Thr Arg Ser Met Arg Thr Pro Ala Arg Asp Ser
130                 135                 140

Thr Val Pro Thr Ile Gly Glu Leu Glu Phe Phe Ala Tyr Ala Glu
145                 150                 155                 160

Gln Gln Gln Gln Arg Leu Phe Met Glu Lys Tyr Asn Phe Asp Ile Val
                165                 170                 175

Asn Asp Val Pro Leu Pro Gly Gly Tyr Glu Trp Val Gln Val Ser Pro
            180                 185                 190

<210> SEQ ID NO 70
<211> LENGTH: 248
<212> TYPE: PRT
<213> ORGANISM: Brassica napus

<400> SEQUENCE: 70

Met Gly Lys Tyr Ile Lys Lys Lys Leu Asp Gly Glu Ala Leu Ser
1               5                   10                  15

Leu Ile Asp Val Ser Pro Ser Pro Leu Gly Val Leu Thr Arg Ala Lys
            20                  25                  30

Ser Leu Ala Leu Gln Arg Arg Leu Gln Lys Pro Pro Ser Ser Pro Ser

```
                35                  40                  45
Pro Asn Pro Pro Pro Ser Lys Gln Glu Ile Thr Asp Cys Ser Gly Gly
 50                  55                  60
Ser Tyr Leu Gln Leu Arg Ser Arg Arg Leu Gln Lys Lys Pro Pro Pro
 65                  70                  75                  80
Ile Val Val Ile Arg Ser Ser Lys Arg Lys Gln Arg Arg Arg Glu Glu
                 85                  90                  95
Glu Gly Arg Asn Pro Asn Pro Asn Pro Gln Asn His Asp Ser Ile Arg
                100                 105                 110
Gly Ser Gly Gly Asp Gly Ser Ser Arg Ser Asp Ser Val Ala Glu Ser
                115                 120                 125
Val Val Phe Gly Lys Glu Lys Asp Phe Asn Gly Gly Ile Asn Arg Glu
                130                 135                 140
Leu Asp Gly Ser Glu Ser Phe Asn Trp Thr Thr Ser Arg Glu Ser Thr
145                 150                 155                 160
Pro Cys Ser Leu Ile Arg Lys His Glu Thr Ile Thr Ser Pro Gly Ser
                165                 170                 175
Ser Thr Lys Leu Ser Asn Gly Ile Ser Asp Asn Ser Asn Gln Arg Glu
                180                 185                 190
Asp Ser Phe Ser Gly Ser His Arg His Leu Pro Thr Thr Pro Glu Met
                195                 200                 205
Asp Glu Phe Phe Ser Ala Ala Glu Glu Glu Gln Lys Gln Phe Ile
                210                 215                 220
Glu Lys Tyr Asn Phe Asp Pro Val Asn Glu Gln Pro Leu Pro Gly Arg
225                 230                 235                 240
Phe Glu Trp Lys Lys Val Asp Asp
                245

<210> SEQ ID NO 71
<211> LENGTH: 199
<212> TYPE: PRT
<213> ORGANISM: Brassica napus

<400> SEQUENCE: 71

Met Gly Arg Tyr Ile Lys Lys Ser Lys Ile Ala Gly Gly Ala Leu Ser
  1                5                  10                  15
Ala Lys Asp Ile Ser His Gln Thr Ala Ser Gly Phe Arg Thr Arg Ala
                 20                  25                  30
Ala Lys Asn Leu Ala Leu Gln Arg Leu Arg Ser His Ser Thr Pro Pro
                 35                  40                  45
Phe Val Asp Ala Asp Ser Phe Arg Tyr Leu Gln Leu Arg Ser Arg Arg
 50                  55                  60
Leu Val Lys Leu Pro Leu Leu Ala Asp Thr Arg Lys Gln Gln Gln Arg
 65                  70                  75                  80
Gln Leu Ala Asn Ser Val Gly Lys Arg Gln Thr Thr Asn Pro Arg Ala
                 85                  90                  95
Asn Pro Val Leu Ser Ser Glu Pro Thr Asn Leu Glu Glu Asp Arg Gly
                100                 105                 110
Ser Asn Leu Val Lys Phe Glu Ser Gly Cys Ser Leu Gly Glu Lys Gly
                115                 120                 125
Leu Glu Phe Glu Ser Gly Asp Arg Glu Thr Thr Pro Cys Ser Leu Arg
                130                 135                 140
Arg Asp Ser Glu Glu Ala Thr Gln Ser Val Pro Ser His Glu Ile Glu
145                 150                 155                 160
```

```
Glu Phe Phe Ala Phe Ala Glu Gln Gln Gln Arg Phe Phe Thr Glu
                165                 170                 175

Lys Tyr Asn Phe Asp Ile Val Ser Glu Asn Pro Leu Pro Gly Arg Tyr
            180                 185                 190

Glu Trp Ile Lys Val Val Pro
        195

<210> SEQ ID NO 72
<211> LENGTH: 190
<212> TYPE: PRT
<213> ORGANISM: Brassica napus

<400> SEQUENCE: 72

Met Ser Glu Arg Asp Pro Asn Cys Lys Arg Asp Ala Arg Ser Leu Glu
1               5                   10                  15

Ala Ser Ser Gln Asn Asp Ser Gln Leu Lys Lys Lys Leu Asp Asp
            20                  25                  30

Asp Phe Val Phe Leu Ala Val Pro Ser Pro Ser Met Ala Ser Ser Asp
        35                  40                  45

Asp Ser Ser Arg Gly Gly Cys Ser Val Thr Ser Ala Gly Glu Asp Asp
    50                  55                  60

Asp Lys Ser Ser Ile Ile Cys Phe Ser Glu Ser Asn Glu Ile Val
65                  70                  75                  80

Arg Lys Ser Pro Thr Val Ser Val Asp Leu Glu Thr His Gln Ile Ser
                85                  90                  95

Asp Asp Leu Ser Val Ser Gly Arg Ile Ala His Arg Asn Glu Ala Asn
            100                 105                 110

Pro Glu Ser Glu Glu Ala Leu Gly Glu Thr Thr Glu Met Glu Ser Ser
        115                 120                 125

Ser Ala Asp Asp Arg Lys Ser Ser Pro Glu Val Ser Lys Ser Pro Thr
    130                 135                 140

Pro Gly Glu Ile Asp Glu Phe Leu Ser Glu Leu Glu Ser Lys Asp Gln
145                 150                 155                 160

Lys Arg Phe Met Asp Lys Tyr Asn Phe Asp Ile Val Asn Asp Lys Pro
                165                 170                 175

Leu Gln Gly Arg Tyr Lys Trp Asp Arg Val Lys Pro Leu Lys
            180                 185                 190

<210> SEQ ID NO 73
<211> LENGTH: 70
<212> TYPE: PRT
<213> ORGANISM: human

<400> SEQUENCE: 73

Asn Leu Phe Gly Pro Val Asp His Glu Glu Leu Thr Arg Asp Leu Glu
1               5                   10                  15

Lys His Cys Arg Asp Met Glu Glu Ala Ser Gln Arg Lys Trp Asn Phe
            20                  25                  30

Asp Phe Gln Asn His Lys Pro Leu Glu Gly Lys Tyr Glu Trp Gln Glu
        35                  40                  45

Val Glu Lys Gly Ser Leu Pro Glu Phe Tyr Tyr Arg Pro Pro Arg Pro
    50                  55                  60

Pro Lys Gly Ala Cys Lys
65                  70

<210> SEQ ID NO 74
<211> LENGTH: 513
```

```
<212> TYPE: DNA
<213> ORGANISM: Artificial Sequence
<220> FEATURE:
<223> OTHER INFORMATION: Krp1 F151A;F153A optimized for expression in
      maize

<400> SEQUENCE: 74
atggtccgga agtgccggaa gacgaaaggc accgtggggg ctagtagcac ctatatgcaa    60
cttaggtcaa gaaggatcgt ctaccgtagc gagaaggcta gttcctctag ttcgtcatgc   120
tgtgcttcaa ataacaacgg cgtgatcgac cttgaggagg agcgggatgg agagacagag   180
acctcttcgt gcaggcgctc cagcaaacgt aaactcttcg agaatcttag ggagaaggag   240
agtatggaaa attctcagca aatcgtagcc ggatttgatt cggcggtgaa agagtctagc   300
gactgctgct gttccagaag gacgagtctg tctactaccg aggagaaggg gaaaagcgcc   360
accgagcaac cgccgacggc tgtcgagatt gaggatttct tgtcgaggc ggagaaacag    420 ctccacgaca attttaagaa gaaatataac gctgacgctg aaaaggagaa gccactggag   480
ggcaggtacg agtgggttaa attgtccgag tga                                513

<210> SEQ ID NO 75
<211> LENGTH: 513
<212> TYPE: DNA
<213> ORGANISM: Artificial Sequence
<220> FEATURE:
<223> OTHER INFORMATION: Krp1 Y149A;F151A;F153A optimized for expression
      in maize

<400> SEQUENCE: 75
atggtccgga agtgccggaa gacgaaaggc accgtggggg ctagtagcac ctatatgcaa    60
cttaggtcaa gaaggatcgt ctaccgtagc gagaaggcta gttcctctag ttcgtcatgc   120
tgtgcttcaa ataacaacgg cgtgatcgac cttgaggagg agcgggatgg agagacagag   180
acctcttcgt gcaggcgctc cagcaaacgt aaactcttcg agaatcttag ggagaaggag   240
agtatggaaa attctcagca aatcgtagcc ggatttgatt cggcggtgaa agagtctagc   300
gactgctgct gttccagaag gacgagtctg tctactaccg aggagaaggg gaaaagcgcc   360
accgagcaac cgccgacggc tgtcgagatt gaggatttct tgtcgaggc ggagaaacag    420 ctccacgaca attttaagaa gaaagcgaac gctgacgctg aaaaggagaa gccactggag   480
ggcaggtacg agtgggttaa attgtccgag tga                                513

<210> SEQ ID NO 76
<211> LENGTH: 46
<212> TYPE: PRT
<213> ORGANISM: Zea mays

<400> SEQUENCE: 76

Ile Pro Ser Ser Thr Glu Met Asn Glu Tyr Phe Ala Ala Glu Gln Arg
1               5                  10                  15

Arg Gln Gln Gln Ala Phe Ile Asp Lys Tyr Asn Phe Asp Pro Val Asn
            20                  25                  30

Asp Cys Pro Leu Pro Gly Arg Phe Glu Trp Val Lys Leu Asp
        35                  40                  45

<210> SEQ ID NO 77
<211> LENGTH: 46
<212> TYPE: PRT
<213> ORGANISM: Zea mays

<400> SEQUENCE: 77
```

Val Pro Ser Ser Arg Glu Met Asn Glu Tyr Phe Ala Ala Glu Gln Arg
1               5                   10                  15

Arg Gln Gln Gln Asp Phe Ile Asp Lys Tyr Asn Phe Asp Pro Ala Asn
                20                  25                  30

Asp Cys Pro Leu Pro Gly Arg Phe Glu Trp Val Lys Leu Asp
            35                  40                  45

<210> SEQ ID NO 78
<211> LENGTH: 47
<212> TYPE: PRT
<213> ORGANISM: Zea mays

<400> SEQUENCE: 78

Ile Pro Ser Ser Leu Glu Met Glu Phe Phe Ser Ala Ala Glu Gln
1               5                   10                  15

Gln Glu Gln His Asn Phe Arg Glu Lys Tyr Asn Phe Cys Pro Val Asn
                20                  25                  30

Asp Cys Pro Leu Pro Gly Arg Tyr Glu Trp Ala Arg Leu Asp Cys
            35                  40                  45

<210> SEQ ID NO 79
<211> LENGTH: 47
<212> TYPE: PRT
<213> ORGANISM: Glycine max

<400> SEQUENCE: 79

Met Pro Thr Glu Leu Glu Leu Glu Glu Phe Phe Ala Ala Ser Glu Lys
1               5                   10                  15

Asp Ile Gln Lys Arg Phe Gln Asp Arg Tyr Asn Tyr Asp Ile Val Lys
                20                  25                  30

Asp Val Pro Leu Glu Gly Arg Tyr Glu Trp Val Gln Leu Lys Pro
            35                  40                  45

<210> SEQ ID NO 80
<211> LENGTH: 47
<212> TYPE: PRT
<213> ORGANISM: Glycine max
<220> FEATURE:
<221> NAME/KEY: misc_feature
<222> LOCATION: (7)..(7)
<223> OTHER INFORMATION: Xaa can be any naturally occurring amino acid

<400> SEQUENCE: 80

Met Pro Thr Glu Leu Glu Xaa Glu Glu Phe Phe Val Ala Ala Glu Lys
1               5                   10                  15

Asp Ile Gln Lys Arg Phe Gln Asp Lys Tyr Asn Tyr Asp Ile Val Lys
                20                  25                  30

Asp Val Pro Leu Glu Gly Arg Tyr Glu Trp Val Gln Leu Lys Pro
            35                  40                  45

<210> SEQ ID NO 81
<211> LENGTH: 45
<212> TYPE: PRT
<213> ORGANISM: Glycine max

<400> SEQUENCE: 81

Met Pro Thr Glu Leu Glu Leu Asp Glu Phe Phe Ala Ala Ala Glu Lys
1               5                   10                  15

Asp Ile Arg Lys Arg Phe Ser Asp Lys Tyr Asn Tyr Asp Ile Val Lys
                20                  25                  30

Gly Val Ser Leu Glu Gly Arg Tyr Glu Trp Val Lys Leu
            35                  40                  45

<210> SEQ ID NO 82
<211> LENGTH: 44
<212> TYPE: PRT
<213> ORGANISM: Glycine max

<400> SEQUENCE: 82

Pro Pro Lys Ala Glu Ile Glu Glu Phe Phe Ala Met Ala Glu Lys Tyr
1               5                   10                  15

Glu Gln Lys Lys Phe Thr Glu Lys Tyr Asn Phe Asp Ile Val Arg Asp
                20                  25                  30

Leu Pro Leu Glu Gly Arg Tyr Gln Trp Val Arg Leu
            35                  40

<210> SEQ ID NO 83
<211> LENGTH: 47
<212> TYPE: PRT
<213> ORGANISM: Glycine max

<400> SEQUENCE: 83

Ile Pro Thr Ser Arg Glu Met Asp Glu Phe Phe Ala Glu Ile Glu Glu
1               5                   10                  15

Ala Gln Gln Lys Lys Phe Ile Glu Lys Tyr Asn Phe Asp Pro Val Asn
                20                  25                  30

Glu Lys Pro Leu Ser Gly Arg Tyr Glu Trp Glu Lys Leu Lys Pro
            35                  40                  45

<210> SEQ ID NO 84
<211> LENGTH: 45
<212> TYPE: PRT
<213> ORGANISM: Populus tremula

<400> SEQUENCE: 84

Ile Pro Thr Thr Arg Glu Met Asp Glu Phe Phe Gly Pro Ala Glu Glu
1               5                   10                  15

Glu Gln Leu Arg Gln Phe Thr Glu Lys Tyr Asn Phe Asp Pro Val Ser
                20                  25                  30

Asp Lys Pro Leu Pro Gly Arg Tyr Glu Trp Glu Lys Leu
            35                  40                  45

<210> SEQ ID NO 85
<211> LENGTH: 43
<212> TYPE: PRT
<213> ORGANISM: Populus tremula

<400> SEQUENCE: 85

Thr Asp Glu Glu Ile Glu Lys Phe Phe Gly Ile Gln Asn Asn Ile
1               5                   10                  15

Pro Gln Cys Phe Lys Asp Lys Tyr Asn Phe Asp Phe Asp Lys Asp Glu
                20                  25                  30

Pro Leu Glu Gly Arg Tyr Glu Trp Ala Arg Leu
            35                  40

<210> SEQ ID NO 86
<211> LENGTH: 45
<212> TYPE: PRT
<213> ORGANISM: Oryza sativa

<400> SEQUENCE: 86

```
Val Pro Ser Ser Leu Glu Met Glu Glu Phe Ala Ala Ala Glu Gln
1               5                   10                  15

Gln Gln His Gln Ala Phe Arg Glu Arg Tyr Asn Phe Cys Pro Val Asn
            20                  25                  30

Asp Cys Pro Leu Pro Gly Arg Tyr Glu Trp Thr Arg Leu
        35                  40                  45

<210> SEQ ID NO 87
<211> LENGTH: 46
<212> TYPE: PRT
<213> ORGANISM: Oryza sativa

<400> SEQUENCE: 87

Pro Pro Glu Glu Glu Val Glu Ala Phe Leu Ala Ala Ala Glu Ser Ser
1               5                   10                  15

Val Ala Arg Arg Phe Ala Ala Lys Tyr Asn Tyr Asp Ile Val Lys Asp
                20                  25                  30

Ala Pro Met Asp Gly Arg Tyr Glu Trp Val Arg Val Arg Pro
            35                  40                  45

<210> SEQ ID NO 88
<211> LENGTH: 168
<212> TYPE: PRT
<213> ORGANISM: Artificial Sequence
<220> FEATURE:
<223> OTHER INFORMATION: BnKrp1 F145A;Y149A

<400> SEQUENCE: 88

Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
                20                  25                  30

Ala Ser Ser Ser Ser Ser Cys Cys Ala Ser Asn Asn Asn Gly Val
            35                  40                  45

Ile Asp Leu Glu Glu Glu Arg Asp Gly Glu Thr Glu Thr Ser Ser Cys
 50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Ser Arg Arg Thr Ser Leu Ser Thr
            100                 105                 110

Thr Glu Glu Lys Gly Lys Ser Ala Thr Glu Gln Pro Pro Thr Ala Val
            115                 120                 125

Glu Ile Glu Asp Phe Phe Val Glu Ala Glu Lys Gln Leu His Asp Asn
130                 135                 140

Ala Lys Lys Lys Ala Asn Phe Asp Phe Glu Lys Glu Lys Pro Leu Glu
145                 150                 155                 160

Gly Arg Tyr Glu Trp Val Lys Leu
                165

<210> SEQ ID NO 89
<211> LENGTH: 168
<212> TYPE: PRT
<213> ORGANISM: Artificial Sequence
<220> FEATURE:
<223> OTHER INFORMATION: BnKRP1 F145A;Y149A;F151A

<400> SEQUENCE: 89
```

```
Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
                100                 105                 110

Thr Glu Glu Lys Gly Lys Ser Ala Thr Glu Gln Pro Pro Thr Ala Val
            115                 120                 125

Glu Ile Glu Asp Phe Phe Val Glu Ala Glu Lys Gln Leu His Asp Asn
    130                 135                 140

Ala Lys Lys Lys Ala Asn Ala Asp Phe Glu Lys Glu Lys Pro Leu Glu
145                 150                 155                 160

Gly Arg Tyr Glu Trp Val Lys Leu
                165
```

<210> SEQ ID NO 90
<211> LENGTH: 168
<212> TYPE: PRT
<213> ORGANISM: Artificial Sequence
<220> FEATURE:
<223> OTHER INFORMATION: BnKrp1 F145A;Y149A;F151A

<400> SEQUENCE: 90

```
Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
                100                 105                 110

Thr Glu Glu Lys Gly Lys Ser Ala Thr Glu Gln Pro Pro Thr Ala Val
            115                 120                 125

Glu Ile Glu Asp Phe Phe Val Glu Ala Glu Lys Gln Leu His Asp Asn
    130                 135                 140

Ala Lys Lys Lys Ala Asn Ala Asp Ala Glu Lys Glu Lys Pro Leu Glu
145                 150                 155                 160

Gly Arg Tyr Glu Trp Val Lys Leu
                165
```

<210> SEQ ID NO 91
<211> LENGTH: 168

```
<212> TYPE: PRT
<213> ORGANISM: Artificial Sequence
<220> FEATURE:
<223> OTHER INFORMATION: BnKrp1 Y149A;F151A

<400> SEQUENCE: 91
```

Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
            100                 105                 110

Thr Glu Glu Lys Gly Lys Ser Ala Thr Glu Gln Pro Pro Thr Ala Val
            115                 120                 125

Glu Ile Glu Asp Phe Phe Val Glu Ala Glu Lys Gln Leu His Asp Asn
    130                 135                 140

Phe Lys Lys Lys Ala Asn Ala Asp Phe Glu Lys Glu Lys Pro Leu Glu
145                 150                 155                 160

Gly Arg Tyr Glu Trp Val Lys Leu
                165

```
<210> SEQ ID NO 92
<211> LENGTH: 168
<212> TYPE: PRT
<213> ORGANISM: Artificial Sequence
<220> FEATURE:
<223> OTHER INFORMATION: BnKrp1 Y149A;F153A

<400> SEQUENCE: 92
```

Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
            100                 105                 110

Thr Glu Glu Lys Gly Lys Ser Ala Thr Glu Gln Pro Pro Thr Ala Val
            115                 120                 125

Glu Ile Glu Asp Phe Phe Val Glu Ala Glu Lys Gln Leu His Asp Asn
    130                 135                 140

Phe Lys Lys Lys Ala Asn Phe Asp Ala Glu Lys Glu Lys Pro Leu Glu
145                 150                 155                 160

Gly Arg Tyr Glu Trp Val Lys Leu
            165

<210> SEQ ID NO 93
<211> LENGTH: 168
<212> TYPE: PRT
<213> ORGANISM: Artificial Sequence
<220> FEATURE:
<223> OTHER INFORMATION: BnKrp1 F151A;F153A

<400> SEQUENCE: 93

Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
            100                 105                 110

Thr Glu Glu Lys Gly Lys Ser Ala Thr Glu Gln Pro Pro Thr Ala Val
        115                 120                 125

Glu Ile Glu Asp Phe Phe Val Glu Ala Glu Lys Gln Leu His Asp Asn
    130                 135                 140

Phe Lys Lys Lys Tyr Asn Ala Asp Ala Glu Lys Glu Lys Pro Leu Glu
145                 150                 155                 160

Gly Arg Tyr Glu Trp Val Lys Leu
            165

<210> SEQ ID NO 94
<211> LENGTH: 168
<212> TYPE: PRT
<213> ORGANISM: Artificial Sequence
<220> FEATURE:
<223> OTHER INFORMATION: BnKrp1 F151A;F153A;Y149A

<400> SEQUENCE: 94

Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
            100                 105                 110

Thr Glu Glu Lys Gly Lys Ser Ala Thr Glu Gln Pro Pro Thr Ala Val

```
                    115                 120                 125
Glu Ile Glu Asp Phe Phe Val Glu Ala Glu Lys Gln Leu His Asp Asn
            130                 135                 140

Phe Lys Lys Lys Ala Asn Ala Asp Ala Glu Lys Glu Lys Pro Leu Glu
145                 150                 155                 160

Gly Arg Tyr Glu Trp Val Lys Leu
                165

<210> SEQ ID NO 95
<211> LENGTH: 168
<212> TYPE: PRT
<213> ORGANISM: Artificial Sequence
<220> FEATURE:
<223> OTHER INFORMATION: BnKrp1 F151A;F153A;E164A

<400> SEQUENCE: 95

Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
            100                 105                 110

Thr Glu Glu Lys Gly Lys Ser Ala Thr Glu Gln Pro Pro Thr Ala Val
            115                 120                 125

Glu Ile Glu Asp Phe Phe Val Glu Ala Glu Lys Gln Leu His Asp Asn
            130                 135                 140

Phe Lys Lys Lys Tyr Asn Ala Asp Ala Glu Lys Glu Lys Pro Leu Glu
145                 150                 155                 160

Gly Arg Tyr Ala Trp Val Lys Leu
                165

<210> SEQ ID NO 96
<211> LENGTH: 168
<212> TYPE: PRT
<213> ORGANISM: Artificial Sequence
<220> FEATURE:
<223> OTHER INFORMATION: BnKrp1 F151A;F153A;W165A

<400> SEQUENCE: 96

Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80
```

```
Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
            100                 105                 110

Thr Glu Glu Lys Gly Lys Ser Ala Thr Glu Gln Pro Pro Thr Ala Val
        115                 120                 125

Glu Ile Glu Asp Phe Phe Val Glu Ala Glu Lys Gln Leu His Asp Asn
    130                 135                 140

Phe Lys Lys Lys Tyr Asn Ala Asp Ala Glu Lys Glu Lys Pro Leu Glu
145                 150                 155                 160

Gly Arg Tyr Glu Ala Val Lys Leu
                165
```

<210> SEQ ID NO 97
<211> LENGTH: 168
<212> TYPE: PRT
<213> ORGANISM: Artificial Sequence
<220> FEATURE:
<223> OTHER INFORMATION: BnKrp1 F151A;F153A;E164A;W165A

<400> SEQUENCE: 97

```
Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45

Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
            100                 105                 110

Thr Glu Glu Lys Gly Lys Ser Ala Thr Glu Gln Pro Pro Thr Ala Val
        115                 120                 125

Glu Ile Glu Asp Phe Phe Val Glu Ala Glu Lys Gln Leu His Asp Asn
    130                 135                 140

Phe Lys Lys Lys Tyr Asn Ala Asp Ala Glu Lys Glu Lys Pro Leu Glu
145                 150                 155                 160

Gly Arg Tyr Ala Ala Val Lys Leu
                165
```

<210> SEQ ID NO 98
<211> LENGTH: 168
<212> TYPE: PRT
<213> ORGANISM: Artificial Sequence
<220> FEATURE:
<223> OTHER INFORMATION: BnKrp1 F151A;F153A;Y149A;E164A

<400> SEQUENCE: 98

```
Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Cys Cys Ala Ser Asn Asn Asn Gly Val
        35                  40                  45
```

Ile Asp Leu Glu Glu Glu Arg Asp Gly Glu Thr Thr Ser Ser Cys
 50                  55                  60

Arg Arg Ser Ser Lys Arg Lys Leu Phe Glu Asn Leu Arg Glu Lys Glu
 65                  70                  75                  80

Ser Met Glu Asn Ser Gln Gln Ile Val Ala Gly Phe Asp Ser Ala Val
                 85                  90                  95

Lys Glu Ser Ser Asp Cys Cys Cys Ser Arg Arg Thr Ser Leu Ser Thr
                100                 105                 110

Thr Glu Glu Lys Gly Lys Ser Ala Thr Glu Gln Pro Pro Thr Ala Val
                115                 120                 125

Glu Ile Glu Asp Phe Phe Val Glu Ala Glu Lys Gln Leu His Asp Asn
                130                 135                 140

Phe Lys Lys Lys Ala Asn Ala Asp Ala Glu Lys Glu Lys Pro Leu Glu
145                 150                 155                 160

Gly Arg Tyr Ala Trp Val Lys Leu
                165

<210> SEQ ID NO 99
<211> LENGTH: 168
<212> TYPE: PRT
<213> ORGANISM: Artificial Sequence
<220> FEATURE:
<223> OTHER INFORMATION: BnKrp1 F151A;F153A;Y149A;W165A

<400> SEQUENCE: 99

Met Val Arg Lys Cys Arg Lys Thr Lys Gly Thr Val Gly Ala Ser Ser
  1               5                  10                  15

Thr Tyr Met Gln Leu Arg Ser Arg Arg Ile Val Tyr Arg Ser Glu Lys
                 20                  25                  30

Ala Ser Ser Ser Ser Ser Cys Cys Ala Ser Asn Asn Asn Gly Val
                 35                  40                  45

Ile Asp Leu Glu Glu Glu Arg Asp Gly Glu Thr Glu Thr Ser Ser Cys
 50                  55                  60

Arg Arg Ser Ser Lys Arg Lys Leu Phe Glu Asn Leu Arg Glu Lys Glu
 65                  70                  75                  80

Ser Met Glu Asn Ser Gln Gln Ile Val Ala Gly Phe Asp Ser Ala Val
                 85                  90                  95

Lys Glu Ser Ser Asp Cys Cys Cys Ser Arg Arg Thr Ser Leu Ser Thr
                100                 105                 110

Thr Glu Glu Lys Gly Lys Ser Ala Thr Glu Gln Pro Pro Thr Ala Val
                115                 120                 125

Glu Ile Glu Asp Phe Phe Val Glu Ala Glu Lys Gln Leu His Asp Asn
                130                 135                 140

Phe Lys Lys Lys Ala Asn Ala Asp Ala Glu Lys Glu Lys Pro Leu Glu
145                 150                 155                 160

Gly Arg Tyr Glu Ala Val Lys Leu
                165

<210> SEQ ID NO 100
<211> LENGTH: 168
<212> TYPE: PRT
<213> ORGANISM: Artificial Sequence
<220> FEATURE:
<223> OTHER INFORMATION: BnKrp1 F151A;F153A;Y149A;E164A;W165A

<400> SEQUENCE: 100

Met Val Arg Lys Cys Arg Lys Thr Lys Gly Thr Val Gly Ala Ser Ser

```
               1               5                    10                      15
             Thr Tyr Met Gln Leu Arg Ser Arg Arg Ile Val Tyr Arg Ser Glu Lys
                              20                       25                       30

Ala Ser Ser Ser Ser Ser Cys Cys Ala Ser Asn Asn Asn Gly Val
                              35                       40                  45

Ile Asp Leu Glu Glu Glu Arg Asp Gly Glu Thr Glu Thr Ser Ser Cys
              50                          55                       60

Arg Arg Ser Ser Lys Arg Lys Leu Phe Glu Asn Leu Arg Glu Lys Glu
              65                       70                  75                  80

Ser Met Glu Asn Ser Gln Gln Ile Val Ala Gly Phe Asp Ser Ala Val
                                   85                       90                  95

Lys Glu Ser Ser Asp Cys Cys Cys Ser Arg Arg Thr Ser Leu Ser Thr
                                   100                      105                 110

Thr Glu Glu Lys Gly Lys Ser Ala Thr Glu Gln Pro Pro Thr Ala Val
                                   115                      120                 125

Glu Ile Glu Asp Phe Phe Val Glu Ala Glu Lys Gln Leu His Asp Asn
                              130                      135                 140

Phe Lys Lys Lys Ala Asn Ala Asp Ala Glu Lys Glu Lys Pro Leu Glu
             145                      150                      155                 160

Gly Arg Tyr Ala Ala Val Lys Leu
                                   165
```

<210> SEQ ID NO 101
<211> LENGTH: 168
<212> TYPE: PRT
<213> ORGANISM: Artificial Sequence
<220> FEATURE:
<223> OTHER INFORMATION: BnKrp1 E164A;W165A

<400> SEQUENCE: 101

```
             Met Val Arg Lys Cys Arg Lys Thr Lys Gly Thr Val Gly Ala Ser Ser
             1               5                    10                      15

Thr Tyr Met Gln Leu Arg Ser Arg Arg Ile Val Tyr Arg Ser Glu Lys
                              20                       25                       30

Ala Ser Ser Ser Ser Ser Cys Cys Ala Ser Asn Asn Asn Gly Val
                              35                       40                  45

Ile Asp Leu Glu Glu Glu Arg Asp Gly Glu Thr Glu Thr Ser Ser Cys
              50                          55                       60

Arg Arg Ser Ser Lys Arg Lys Leu Phe Glu Asn Leu Arg Glu Lys Glu
              65                       70                  75                  80

Ser Met Glu Asn Ser Gln Gln Ile Val Ala Gly Phe Asp Ser Ala Val
                                   85                       90                  95

Lys Glu Ser Ser Asp Cys Cys Cys Ser Arg Arg Thr Ser Leu Ser Thr
                                   100                      105                 110

Thr Glu Glu Lys Gly Lys Ser Ala Thr Glu Gln Pro Pro Thr Ala Val
                                   115                      120                 125

Glu Ile Glu Asp Phe Phe Val Glu Ala Glu Lys Gln Leu His Asp Asn
                              130                      135                 140

Phe Lys Lys Lys Tyr Asn Phe Asp Phe Glu Lys Glu Lys Pro Leu Glu
             145                      150                      155                 160

Gly Arg Tyr Ala Ala Val Lys Leu
                                   165
```